(12) United States Patent
Best et al.

(10) Patent No.: US 8,288,389 B2
(45) Date of Patent: Oct. 16, 2012

(54) PIPERAZINE DERIVATIVE HAVING AFFINITY FOR THE HISTAMINE H3 RECEPTOR

(75) Inventors: Desmond John Best, Essex (GB); Sing Yeung Mak, Singapore (SG); Barry Sidney Orlek, Essex (GB); Geracimos Rassias, Stevenage (GB); Pamela Joan Theobald, Essex (GB)

(73) Assignee: Glaxo Group Limited, Greenford, Middlesex (GB)

( * ) Notice: Subject to any disclaimer, the term of this patent is extended or adjusted under 35 U.S.C. 154(b) by 156 days.

(21) Appl. No.: 12/676,158

(22) PCT Filed: Sep. 4, 2008

(86) PCT No.: PCT/EP2008/061664
§ 371 (c)(1),
(2), (4) Date: Mar. 3, 2010

(87) PCT Pub. No.: WO2009/030716
PCT Pub. Date: Mar. 12, 2009

(65) Prior Publication Data
US 2010/0204242 A1    Aug. 12, 2010

(30) Foreign Application Priority Data

Sep. 6, 2007 (GB) .................................. 0717336.2
Aug. 15, 2008 (GB) .................................. 0814987.4

(51) Int. Cl.
*A61K 31/496* (2006.01)
*C07D 309/12* (2006.01)

(52) U.S. Cl. ..................................... 514/254.1; 544/374

(58) Field of Classification Search .................. None
See application file for complete search history.

(56) References Cited

U.S. PATENT DOCUMENTS

| | | | |
|---|---|---|---|
| 7,148,215 B2 | 12/2006 | Ratcliffe et al. | 514/221 |
| 7,449,464 B2 | 11/2008 | Martin et al. | 514/248 |
| 7,704,994 B2 | 4/2010 | Sehmi et al. | 514/217.01 |
| 7,846,922 B2 | 12/2010 | Bruton et al. | 514/218 |
| 2009/0131415 A1 | 5/2009 | Letavic et al. | |
| 2009/0170869 A1 | 7/2009 | Best et al. | 514/254.1 |
| 2010/0273778 A1* | 10/2010 | Cowart et al. | 514/217.01 |

FOREIGN PATENT DOCUMENTS

| | | |
|---|---|---|
| WO | WO98/37077 | 8/1998 |
| WO | WO99/42107 | 8/1999 |
| WO | WO02/08221 | 1/2002 |
| WO | WO02/12190 | 2/2002 |
| WO | WO 03/004480 A2 | 1/2003 |
| WO | WO03/024917 | 3/2003 |
| WO | WO03/066604 | 8/2003 |
| WO | WO2004/035556 | 4/2004 |
| WO | WO 2004/037800 A1 | 5/2004 |
| WO | WO 2004/037801 | 5/2004 |
| WO | WO 2004/101546 A1 | 11/2004 |
| WO | WO 2005/040144 | 5/2005 |
| WO | WO 2006/040192 A1 | 4/2006 |
| WO | WO 2007/053386 A2 | 5/2007 |
| WO | WO 2007/053427 A2 | 5/2007 |
| WO | WO 2008/076685 A2 | 6/2008 |
| WO | WO 2009/024823 A2 | 2/2009 |

OTHER PUBLICATIONS

Phillips et al. Annual Reports in medicinal Chemistry, vol. 33,p. 31-40 (1998).*
Passani et al. Neuroscience and Biobehavioral Reviews, vol. 24, p. 107-113 (2000).*
Office Action date Jul. 23, 2010 on related copending U.S. Appl. No. 12/203,946.
Giovannini et al., Effects of histamine H3 receptor agonists and antagonists on cognitive performance and scopolamine-induced amnesia, Behay. Brain Res. 104:147-155 (1999).
Leurs et al., Therapeutic potential of histamine H3 receptor agonists and antagonists, Trends Pharmacol Sci. 19(5):177-183 (1998).
Lovenberg et al., Cloning and Functional Expression of the Human Histamine H3 Receptor, Molecular Pharmacology, 55:1101-1107 (1999).

* cited by examiner

*Primary Examiner* — Emily Bernhardt
(74) *Attorney, Agent, or Firm* — Haiyan Chen; James C Kellerman; Carl Battle

(57) ABSTRACT

The present invention relates to 1-(1-methylethyl)-4-{[4-(tetrahydro-2H-pyran-4-yloxy)phenyl]carbonyl}piperazine

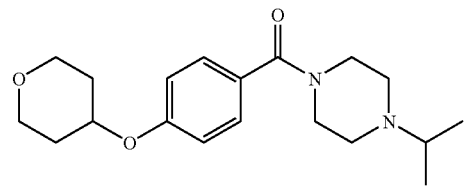

or a pharmaceutically acceptable salt thereof, in particular the hydrochloride salt thereof and crystalline forms of the hydrochloride salt; to processes for the preparation of the compound or its salt; to compositions containing it; and to its use in the treatment or prophylaxis of neurological or psychiatric diseases, such as cognitive impairment, fatigue or a sleep disorder, for example in a mammal such as a human.

The compound or a salt thereof has affinity for and is an antagonist and/or inverse agonist of the histamine H3 receptor.

4 Claims, 14 Drawing Sheets

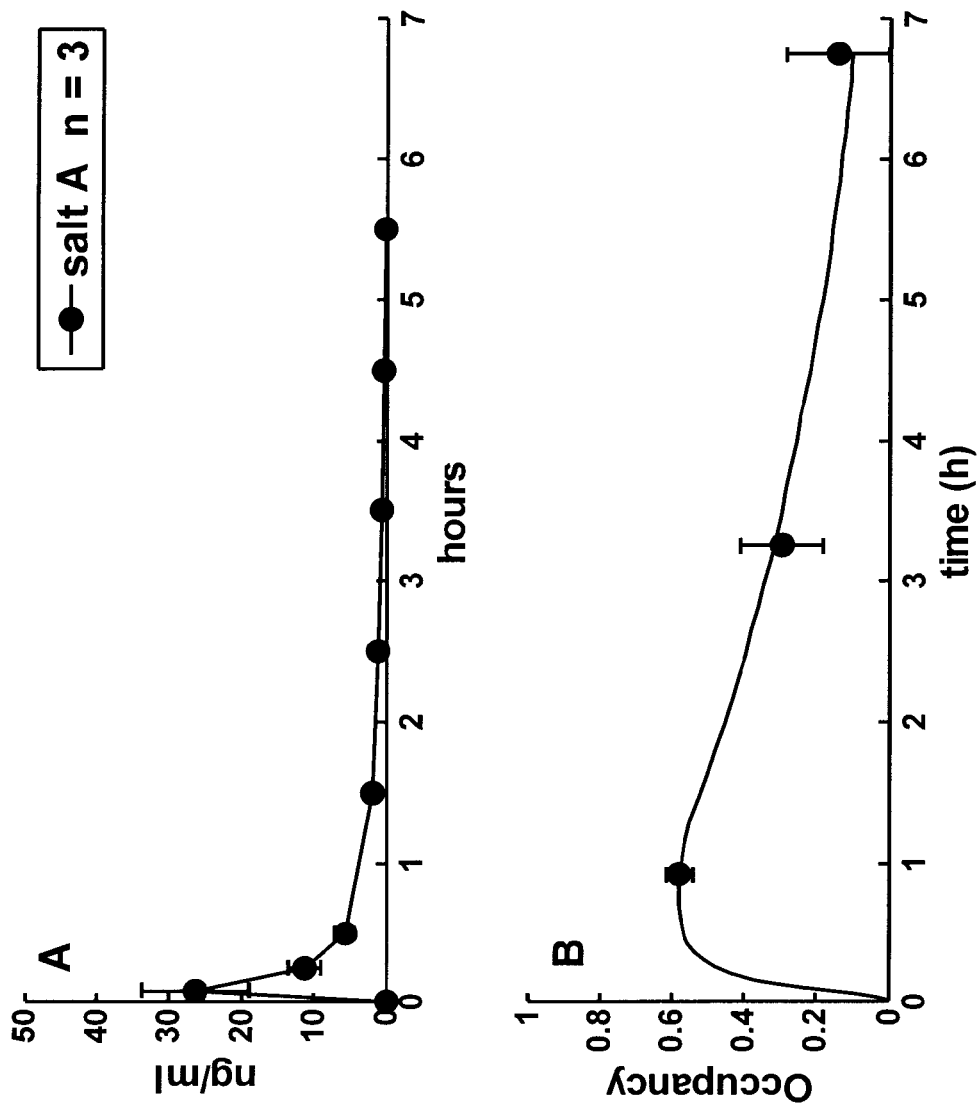
Figure 13, A and B

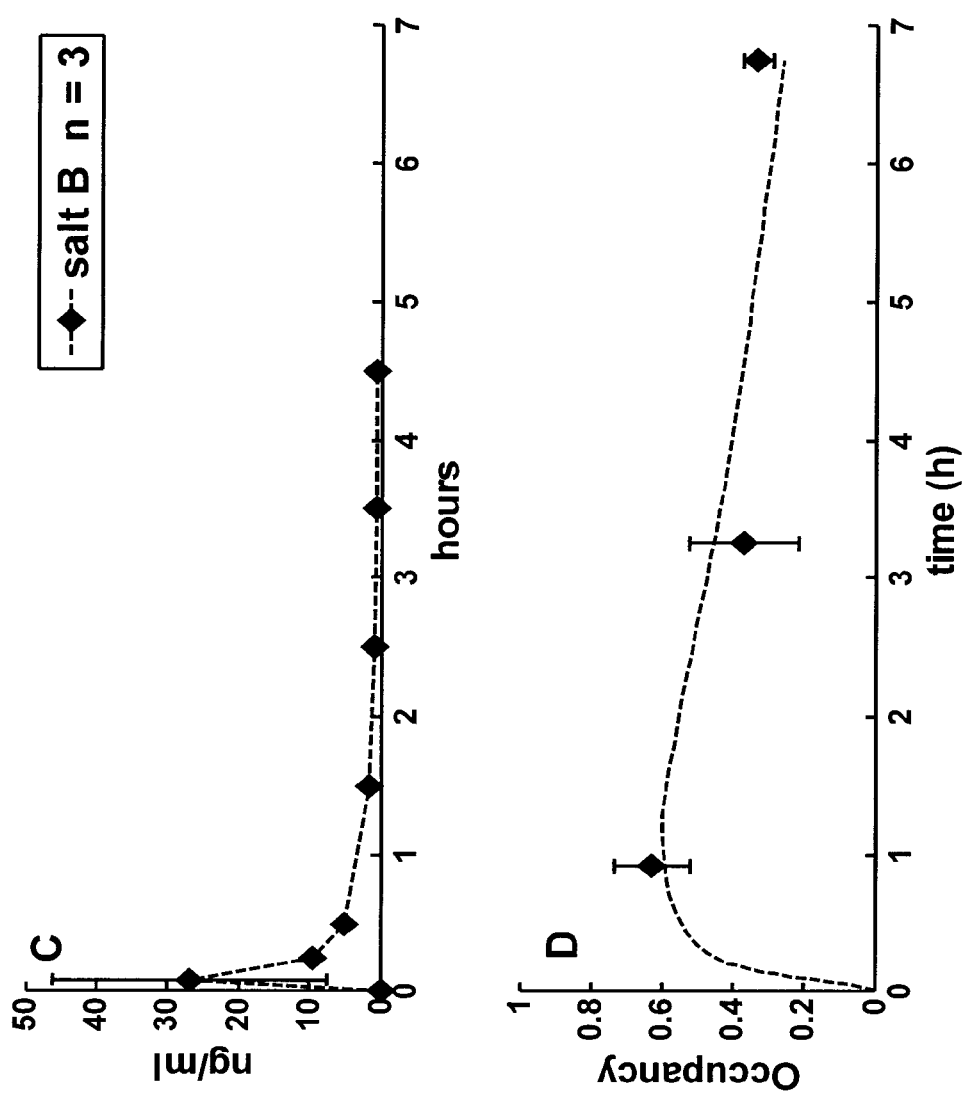
Figures 13, C and D

PIPERAZINE DERIVATIVE HAVING AFFINITY FOR THE HISTAMINE H3 RECEPTOR

This application is a 371 of International Application No. PCT/EP2008/061664, filed 4 Sep. 2008, which claims the priority of GB Application No. GB 0814987.4 filed 15 Aug. 2008 and GB Application No. GB 0717336.2 filed 6 Sep. 2007, which are incorporated herein in their entirety.

BACKGROUND OF THE INVENTION

The present invention relates to a novel piperazine derivative having pharmacological activity, to processes for its preparation, to compositions containing it, and to its use in the treatment of neurological or psychiatric disorders such as cognitive impairment e.g. in Alzheimer's disease.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed. Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). The histamine H3 receptor antagonist GSK189254 inhibited [3]R-α-methylhistamine ex vivo binding in the rat cortex following oral administration to the rat, and at certain oral doses improved performance of rats in the following cognition paradigms: passive avoidance, water maze, object recognition, and attentional set shift (A. D. Medhurst et al., *J. Pharmacol. Exp. Therap.*, 2007, 321(3), 1032-1045.).

These data suggest that novel H3 antagonists and/or inverse agonists could be useful for the treatment of cognitive impairments in neurological diseases such as Alzheimer's disease or a related neurodegenerative disorder.

WO 2005/040144 A1 (Glaxo Group Limited) discloses a series of 1-benzoyl-substituted diazepanyl derivatives having affinity for and being antagonists and/or inverse agonists of the histamine H3 receptor. Example 10 of WO 2005/040144 A1 discloses 1-(isopropyl)-4-{[4-(tetrahydro-2H-pyran-4-yloxy)phenyl]carbonyl}hexahydro-1H-1,4-diazepine hydrochloride:

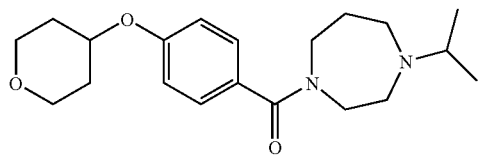

WO 2004/037801 A1 (Janssen Pharmaceutica, N.V.) discloses a series of piperazinyl and diazepanyl benzamides and benzothiamides with the ability to modulate the activity of the histamine receptor, specifically the H3 receptor.

WO 2004/101546 A1 (Glaxo Group Limited) discloses a number of (piperidine-4-carbonyl)-piperazine derivatives and (piperidine-4-carbonyl)-[1,4]-diazepane derivatives having affinity for and being antagonists and/or inverse agonists of the histamine H3 receptor.

WO 03/004480 A2 (Novo Nordisk A/S and Boehringer Ingelheim International GmbH) discloses a series of substituted piperazines and diazapanes having binding affinity to the histamine H3 receptor.

BRIEF SUMMARY OF THE INVENTION

The present invention provides a compound or salt thereof, which has affinity for, and which is an antagonist and/or inverse agonist of, the histamine H3 receptor.

The present invention provides, in a first aspect, 1-(1-methylethyl)-4-{[4-(tetrahydro-2H-pyran-4-yloxy)phenyl]carbonyl}piperazine

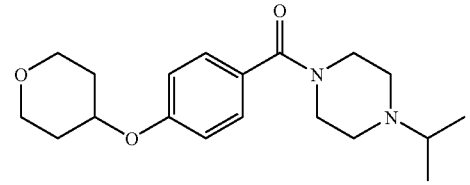

or a salt thereof.

BRIEF DESCRIPTION OF THE DRAWINGS

FIG. 12, graph B, is a graph showing the average (mean) measured H3 receptor occupancy time course at three time points during an in vivo pig-PET study, and the $k_{on}$-$k_{off}$ limited model fitted to it, for "salt A" within the present invention (measurements as filled circles, and model fit as solid line), and for "salt B" a comparator compound (measurements as filled diamonds, and model fit as dashed line), following 50 micrograms/kg intravenous administration of salt A or salt B to pigs.

FIG. 13, parts A and B, are graphs showing the average (mean) plasma concentration over time and average (mean) H3 receptor occupancy time course respectively for "salt A" (only), as shown in part of FIG. 12 graphs A and B.

FIG. 13, parts C and D, are graphs showing the average (mean) plasma concentration over time and average (mean) H3 receptor occupancy time course respectively for "salt B" (only), as shown in part of FIG. 12 graphs A and B.

DETAILED DESCRIPTION OF THE INVENTION

Figure 1:
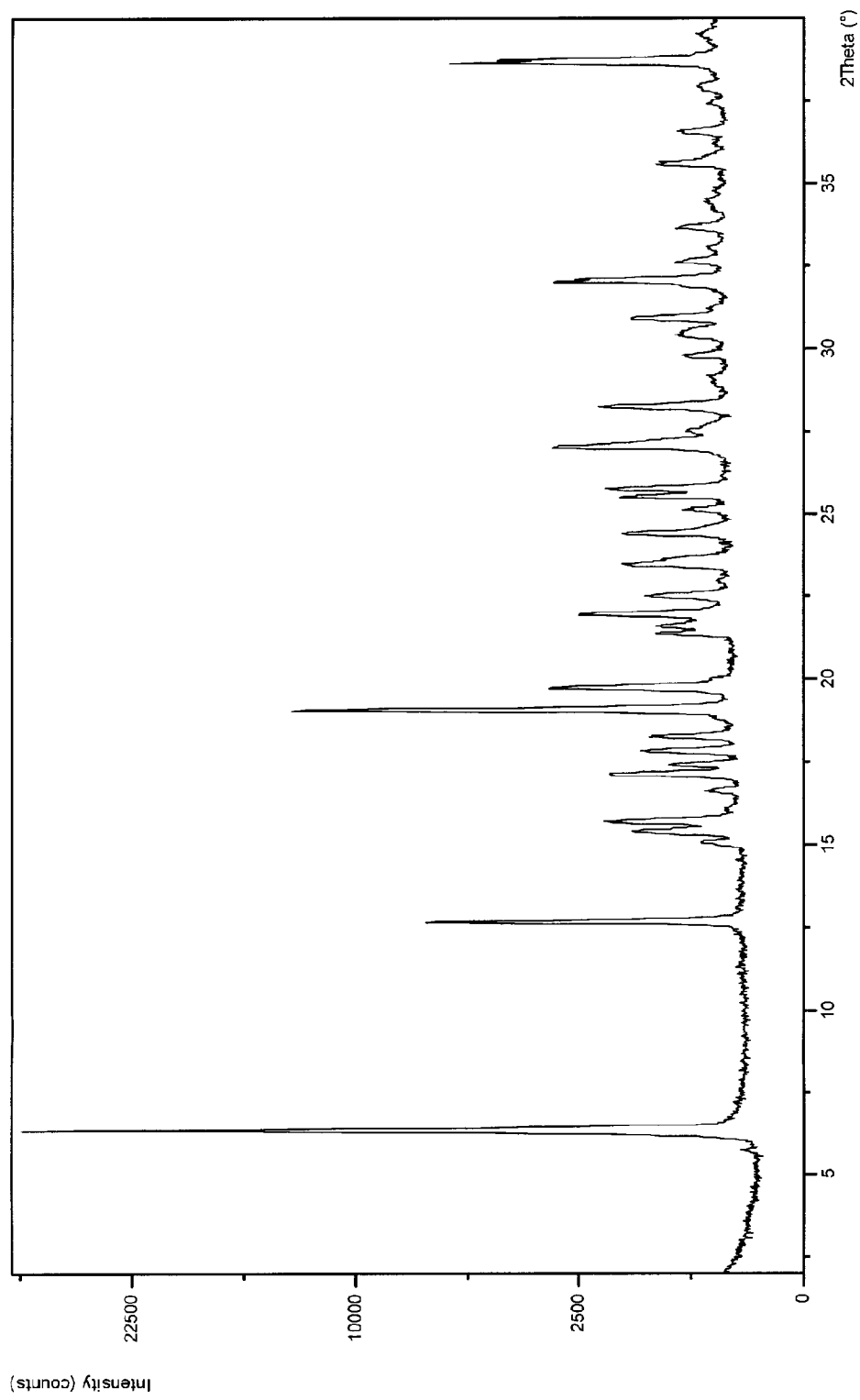
FIG. 1 is an X-ray powder diffraction (XRPD) spectrum of crystalline Form 1 of 1-(1-methylethyl)-4-{[4-(tetrahydro-2H-pyran-4-yloxy)phenyl]carbonyl}piperazine hydrochloride, expressed in terms of two-theta angles (in degrees), and obtained with a diffractometer using copper Kα (copper K-alpha) X-radiation, with a step size of 0.0167° two-theta, a time per step of 31.75 sec, and using a sample mounted on a silicon wafer plate.

The present invention provides a compound or salt thereof, which has affinity for, and which is an antagonist and/or inverse agonist of, the histamine H3 receptor.

The present invention provides, in a first aspect, 1-(1-methylethyl)-4-{[4-(tetrahydro-2H-pyran-4-yloxy)phenyl]carbonyl}piperazine

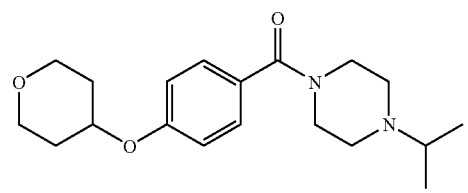

or a salt thereof.

In preliminary tests comprising oral administration to rats or pigs, 1-(1-methylethyl)-4-{[4-(tetrahydro-2H-pyran-4-yloxy)phenyl]carbonyl}piperazine, as its hydrochloride salt, has exhibited in rats and pigs certain time courses (decays over time) of brain histamine H3 receptor occupancy (see the Rat ex vivo binding studies and the Pig-PET studies hereinafter), which suggest that 1-(1-methylethyl)-4-{[4-(tetrahydro-2H-pyran-4-yloxy)phenyl]carbonyl}piperazine or a pharmaceutically acceptable salt thereof might have certain suitable properties for human pharmaceutical use, in particular in the treatment of cognitive impairment in humans such as cognitive impairment in Alzheimer's disease.

In the context of this invention, reference to 1-(1-methylethyl)-4-{[4-(tetrahydro-2H-pyran-4-yloxy)phenyl]carbonyl}piperazine (the "free base") or a salt thereof encompasses solvates and hydrates of the free base or the salt thereof.

In one embodiment, the invention provides 1-(1-methylethyl)-4-{[4-(tetrahydro-2H-pyran-4-yloxy)phenyl]carbonyl}piperazine (the "free base").

Because of its potential use in medicine, a salt of 1-(1-methylethyl)-4-{[4-(tetrahydro-2H-pyran-4-yloxy)phenyl]carbonyl}piperazine is preferably a pharmaceutically acceptable salt thereof, in particular a pharmaceutically acceptable acid addition salt thereof.

Pharmaceutically acceptable acid addition salts of 1-(1-methylethyl)-4-{[4-(tetrahydro-2H-pyran-4-yloxy)phenyl]carbonyl}piperazine include hydrobromide (e.g. monohydrobromide), hydrochloride (e.g. monohydrochloride), sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salts. Such salts can generally be formed by mixing with the appropriate acid, optionally in a suitable solvent such as an organic solvent, to give the salt, which can be isolated, for example by crystallisation and filtration, usually followed by drying.

The invention includes within its scope all possible stoichiometric and non-stoichiometric forms of the salts of the compound of the invention including hydrates and solvates.

In one preferred embodiment, the compound or salt is in the form of a hydrochloride salt, 1-(1-methylethyl)-4-{[4-(tetrahydro-2H-pyran-4-yloxy)phenyl]carbonyl}piperazine hydrochloride, typically the monohydrochloride salt.

1-(1-Methylethyl)-4-{[4-(tetrahydro-2H-pyran-4-yloxy) phenyl]carbonyl}piperazine hydrochloride, e.g. monohydrochloride, can be a solid form, particularly a crystalline form, more particularly crystalline Form 1 or crystalline Form 2.

The invention therefore also provides crystalline Form 1 of 1-(1-methylethyl)-4-{[4-(tetrahydro-2H-pyran-4-yloxy) phenyl]carbonyl}piperazine hydrochloride, e.g. monohydrochloride, (hereinafter "crystalline Form 1").

Crystalline Form 1 of 1-(1-methylethyl)-4-{[4-(tetrahydro-2H-pyran-4-yloxy)phenyl]carbonyl}piperazine hydrochloride, e.g. monohydrochloride, can be characterised by an X-ray powder diffraction (XRPD) spectrum having five or more, e.g. eight or more, e.g. all, of the following peaks defined as degrees two-theta angles obtained with a diffractometer using copper Kα (copper K-alpha) X-radiation:

6.4±0.1, 12.7±0.1, 15.4±0.1, 15.7±0.1, 17.1±0.1, 19.1±0.1, 19.7±0.1, 21.9±0.1, 25.5±0.1, 27.0±0.1, and 28.2±0.1 degrees two-theta;

provided that the X-ray powder diffraction spectrum has the following two peaks:

15.7±0.1 and 25.5±0.1 degrees two-theta.

Alternatively or additionally, crystalline Form 1 of 1-(1-methylethyl)-4-{[4-(tetrahydro-2H-pyran-4-yloxy)phenyl] carbonyl}piperazine hydrochloride, e.g. monohydrochloride, can be characterised by an X-ray powder diffraction (XRPD) spectrum substantially the same as that shown in FIG. 1, expressed in terms of two-theta angles (in degrees) and obtained with a diffractometer using copper Kα (copper K-alpha) X-radiation.

In one embodiment, crystalline Form 1, characterised by the XRPD spectrum peaks defined herein and/or characterised by an XRPD spectrum substantially the same as that shown in FIG. 1, can be additionally characterised as having been obtained with a diffractometer using a step size of 0.0167° two-theta or less, and/or a time per step of 31.75 sec or more, and/or using a sample mounted on a silicon wafer plate.

Figure 5:
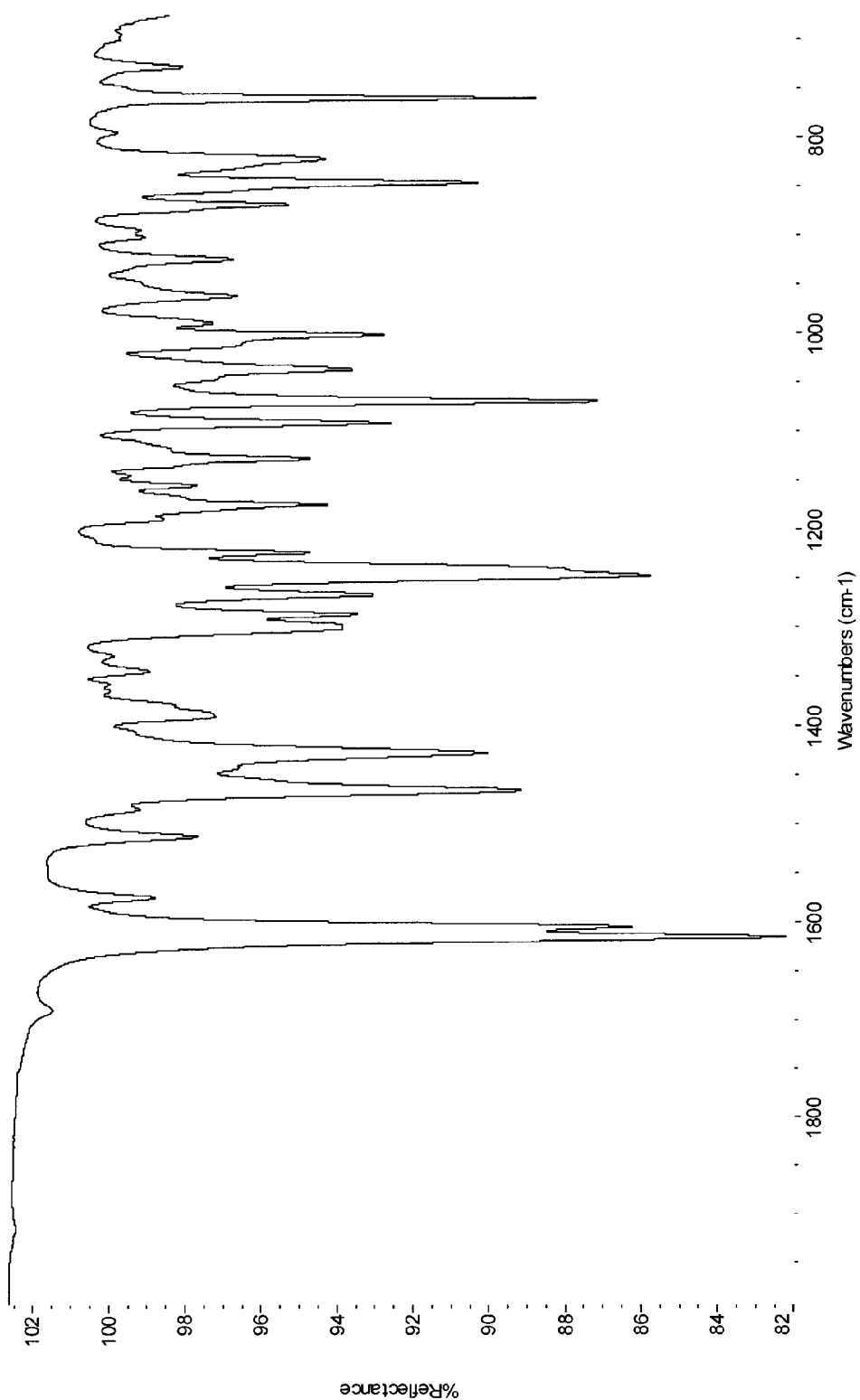
FIG. 5 is a Fourier-Transform Infrared (FT-IR) spectrum for crystalline Form 1 of 1-(1-methylethyl)-4-{[4-(tetrahydro-2H-pyran-4-yloxy)phenyl]carbonyl}piperazine hydrochloride, showing the spectral region from 2000 to 675 cm$^{-1}$.

Alternatively or additionally, crystalline Form 1 of 1-(1-methylethyl)-4-{[4-(tetrahydro-2H-pyran-4-yloxy)phenyl] carbonyl}piperazine hydrochloride, e.g. monohydrochloride, can be characterised by a solid-form Fourier-Transform Infrared (FT-IR) spectrum substantially the same as that shown in FIG. 5. FIG. 5 shows the FT-IR spectrum of crystalline Form 1 in the spectral region from 2000 to 675 cm$^{-1}$. The FT-IR spectrum can e.g. be measured using a Nicolet Avatar 360 FT-IR spectrometer, and/or can e.g. be as measured at 4 cm$^{-1}$ or 2 cm$^{-1}$ resolution. A variation can be allowed for each peak of about ±2 cm$^{-1}$.

Alternatively or additionally, crystalline Form 1 of 1-(1-methylethyl)-4-{[4-(tetrahydro-2H-pyran-4-yloxy)phenyl] carbonyl}piperazine hydrochloride, e.g. monohydrochloride, can be characterised by a $^{13}$C solid-state nuclear magnetic resonance (solid-state NMR) spectrum having the following chemical shifts for the resonances: 18.5±0.3, 30.4±0.3, 31.8±0.3, 37.6±0.3, 45.8±0.3, 49.4±0.3, 52.3±0.3, 59.2±0.3, 63.6±0.3, 68.4±0.3, 110.3±0.3, 118.8±0.3, 128.4±0.3, 131.2±0.3, 133.9±0.3, 159.1±0.3, and 167.6±0.3 ppm. This solid-state NMR spectrum can for example be obtained at a frequency of 90.55 MHz for $^{13}$C observation, e.g. using a 4-mm Bruker HFX MAS (magic-angle spinning) probe at a temperature of 296K, and/or e.g. using a spinning speed of 8 kHz. Data can e.g. be acquired using a cross polarisation sequence with side-band suppression. A relaxation delay of 10 seconds can be used during scanning.

In one embodiment, the hydrochloride salt of the invention is substantially (e.g. 60% or more or 70% or more or 80% or more by weight or molarity) in the form of crystalline Form 1 in terms of crystal form purity.

The invention also provides crystalline Form 2 of 1-(1-methylethyl)-4-{[4-(tetrahydro-2H-pyran-4-yloxy)phenyl] carbonyl}piperazine hydrochloride, e.g. monohydrochloride, (hereinafter "crystalline Form 2").

Without being bound by theory, crystalline Form 2 appears to be more thermodynamically stable than crystalline Form 1, which may give certain advantages in relation to storage, formulation and/or use.

Crystalline Form 2 of 1-(1-methylethyl)-4-{[4-(tetrahydro-2H-pyran-4-yloxy)phenyl]carbonyl}piperazine hydrochloride, e.g. monohydrochloride, can be characterised by an X-ray powder diffraction (XRPD) spectrum having five or more, e.g. eight or more, e.g. all, of the following peaks defined as degrees two-theta angles obtained with a diffractometer using copper Kα (copper K-alpha) X-radiation:

6.4±0.1, 12.8±0.1, 15.4±0.1, 19.2±0.1, 19.7±0.1, 20.0±0.1, 21.8±0.1, 21.9±0.1, 23.5±0.1, 24.65±0.1 (or 24.7±0.1), 25.8±0.1, and 27.0±0.1 degrees two-theta;

provided that the X-ray powder diffraction spectrum has the following two peaks:

20.0±0.1 degrees two-theta,
and either 24.65±0.1 or 24.7±0.1 degrees two-theta.

Figure 2:
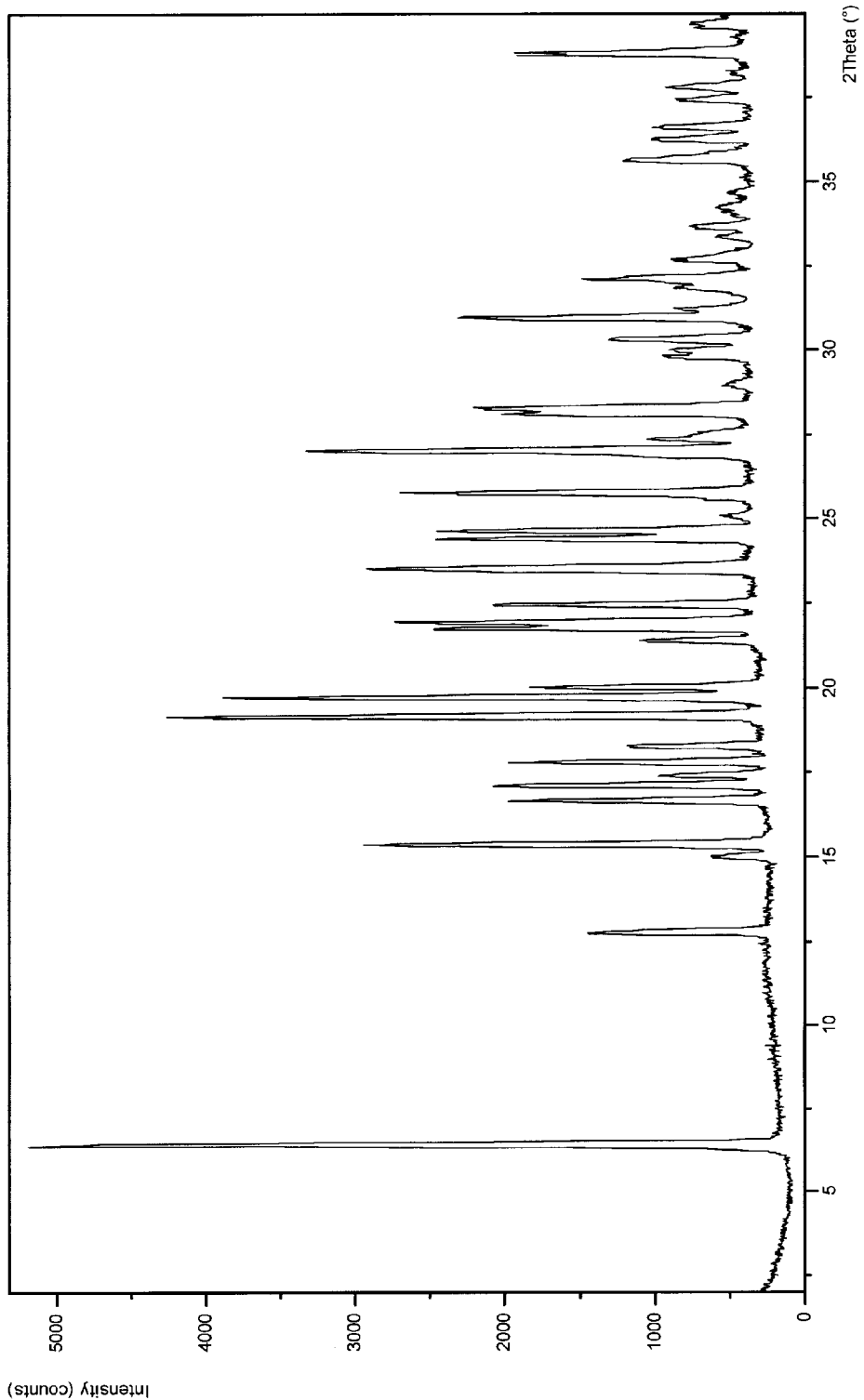
FIG. 2 is an X-ray powder diffraction (XRPD) spectrum of crystalline Form 2 of 1-(1-methylethyl)-4-{[4-(tetrahydro-2H-pyran-4-yloxy)phenyl]carbonyl}piperazine hydrochloride, expressed in terms of two-theta angles (in degrees), and obtained with a diffractometer using copper Kα (copper K-alpha) X-radiation, with a step size of 0.0167°two-theta, a time per step of 31.75 sec, and using a sample mounted on a silicon wafer plate.

Alternatively or additionally, crystalline Form 2 of 1-(1-methylethyl)-4-{[4-(tetrahydro-2H-pyran-4-yloxy)phenyl] carbonyl}piperazine hydrochloride, e.g. monohydrochloride, can be characterised by an X-ray powder diffraction (XRPD) spectrum substantially the same as that shown in FIG. 2, expressed in terms of two-theta angles (in degrees) and obtained with a diffractometer using copper Kα (copper K-alpha) X-radiation.

In one embodiment, crystalline Form 2, characterised by the XRPD spectrum peaks defined herein and/or characterised by an XRPD spectrum substantially the same as that shown in FIG. 2, can be additionally characterised as having been obtained with a diffractometer using a step size of 0.0167° two-theta or less, and/or a time per step of 31.75 sec or more, and/or using a sample mounted on a silicon wafer plate.

Figure 7:
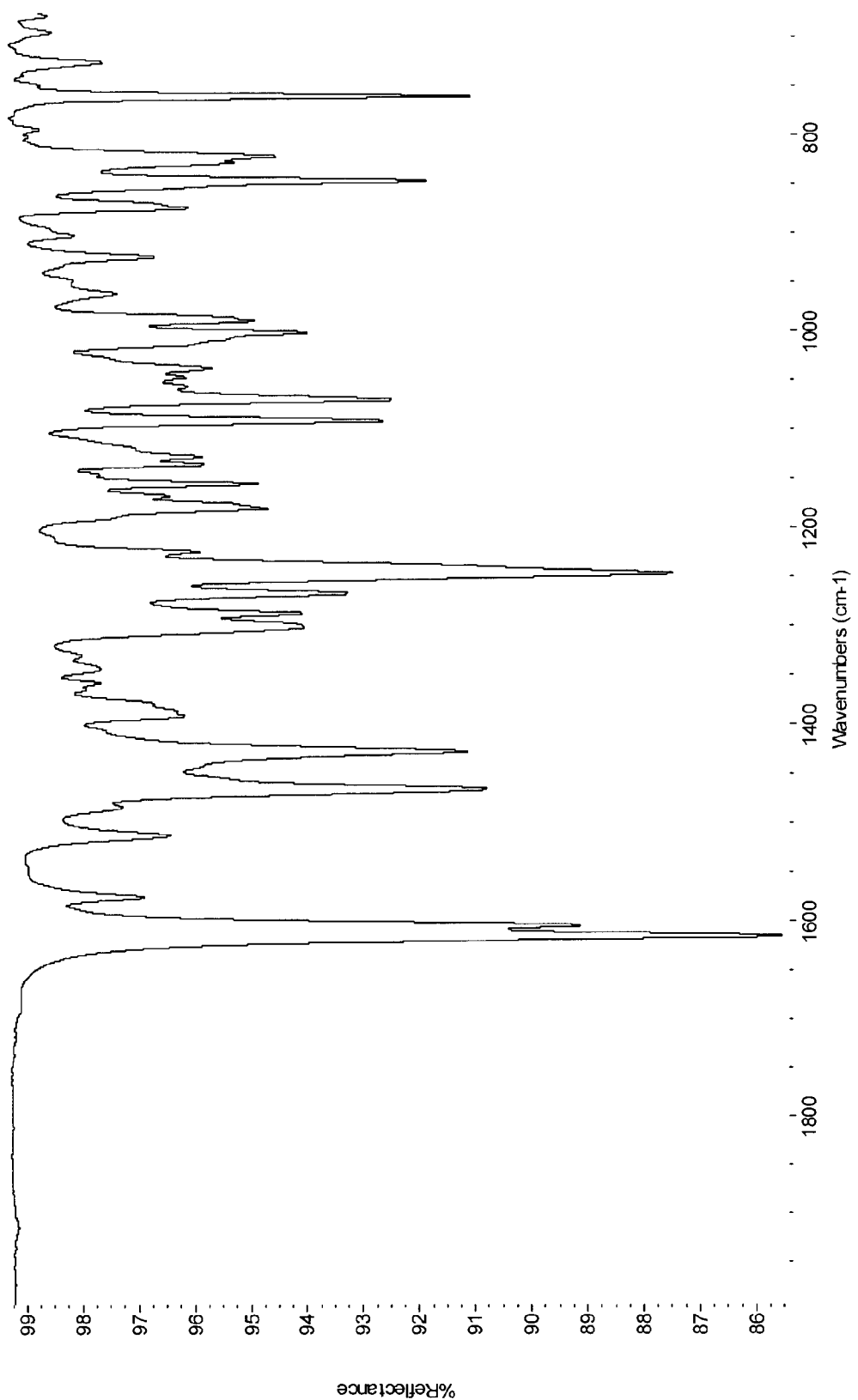
FIG. 7 is a Fourier-Transform Infrared (FT-IR) spectrum for crystalline Form 2 of 1-(1-methylethyl)-4-{[4-(tetrahydro-2H-pyran-4-yloxy)phenyl]carbonyl}piperazine hydrochloride, showing the spectral region from 2000 to 675 cm$^{-1}$.

Alternatively or additionally, crystalline Form 2 of 1-(1-methylethyl)-4-{[4-(tetrahydro-2H-pyran-4-yloxy)phenyl] carbonyl}piperazine hydrochloride, e.g. monohydrochloride, can be characterised by a solid-form Fourier-Transform Infrared (FT-IR) spectrum substantially the same as that shown in FIG. 7. FIG. 7 shows the FT-IR spectrum of crystalline Form 2 in the spectral region from 2000 to 675 cm$^{-1}$. The FT-IR spectrum can e.g. be measured using a Nicolet Avatar 360 FT-IR spectrometer, and/or can e.g. be as measured at 4 cm$^{-1}$ or 2 cm$^{-1}$ resolution. A variation can be allowed for each peak of ±2 cm$^{-1}$ such as ±1 cm$^{-1}$.

Alternatively or additionally, crystalline Form 2 of 1-(1-methylethyl)-4-{[4-(tetrahydro-2H-pyran-4-yloxy)phenyl] carbonyl}piperazine hydrochloride, e.g. monohydrochloride, can be characterised by a $^{13}$C solid-state nuclear magnetic resonance (solid-state NMR) spectrum having the following chemical shifts for the resonances: 18.8±0.3, 19.5±0.3, 32.4±0.3, 37.5±0.3, 45.7±0.3, 49.3±0.3, 52.7±0.3, 59.1±0.3, 66.3±0.3, 71.1±0.3, 109.4±0.3, 119.6±0.3, 128.4±0.3, 131.3±0.3, 134.3±0.3, 158.7±0.3, and 167.8±0.3 ppm. This solid-state NMR spectrum can for example be obtained at a frequency of 90.55 MHz for $^{13}$C observation, e.g. using a 4-mm Bruker HFX MAS (magic-angle spinning) probe at a temperature of 296K, and/or e.g. using a spinning speed of 8 kHz. Data can e.g. be acquired using a cross polarisation sequence with side-band suppression. A relaxation delay of 10 seconds can be used during scanning.

The hydrochloride salt of the invention can suitably be substantially (e.g. 70% or more or 80% or more or 90% or more or 95% or more by weight or molarity) in the form of crystalline Form 2 in terms of crystal form purity.

Synthetic Processes

The present invention also provides a process for the preparation of 1-(1-methylethyl)-4-{[4-(tetrahydro-2H-pyran-4-yloxy)phenyl]carbonyl}piperazine or a salt (e.g. pharmaceutically acceptable salt) thereof, which process comprises:
- a) reacting 4-(tetrahydro-2H-pyran-4-yloxy)benzoyl chloride with 1-isopropyl piperazine; or
- b) reacting 4-(tetrahydro-2H-pyran-4-yloxy)benzoic acid, or a non-acid-chloride derivative thereof in which the carboxylic acid group has been activated, with 1-isopropyl piperazine;

and optionally preparing a salt (e.g. pharmaceutically acceptable salt) of 1-(1-methylethyl)-4-{[4-(tetrahydro-2H-pyran-4-yloxy)phenyl]carbonyl}piperazine.

Process (a) typically comprises the use of amide formation conditions in the presence of a suitable base such as triethylamine or a solid supported base (e.g. diethylaminomethylpolystyrene), in an appropriate solvent e.g. a non-aqueous organic solvent such as dichloromethane, at an appropriate temperature, for example from about −10° C. to about 40° C., such as room temperature. In a particular embodiment of process (a), a catalytic amount of N,N-dimethylformamide (DMF) is added to catalyse the reaction.

In the synthetic processes, room temperature (ambient temperature) is usually 12-35° C., for example 18-30° C. or 18-25° C., such as about 22° C.

Process (b) typically comprises activation of 4-(tetrahydro-2H-pyran-4-yloxy)benzoic acid with a coupling reagent, e.g. in a suitable solvent e.g. a polar aprotic organic solvent, such as N,N-dimethylformamide, dimethylsulfoxide, acetonitrile or propionitrile, followed by reaction with 1-isopropyl piperazine.

In one embodiment, the coupling reagent is an organic di-substituted carbodiimide, such as 1-(3-dimethylaminopropyl)-3-ethylcarbodiimide hydrochloride (EDC) or dicyclohexylcarbodiimide (DCC), in which case: the reaction can optionally be carried out in the presence of 1-hydroxybenzotriazole (HOBT), and/or the reaction solvent can for example be N,N-dimethylformamide, and/or the reaction temperature can e.g. be from about 0° C. to about 40° C., such as room temperature.

In process (b), in one embodiment, the coupling reagent is carbonyl diimidazole, pivaloyl chloride (trimethylacetyl chloride) or 2-propane phosphonic acid anhydride. However, for activation of the 4-(tetrahydro-2H-pyran-4-yloxy)benzoic acid with a coupling reagent, it is preferable, especially for processes carried out on a medium or large scale, that the coupling reagent is carbonyl diimidazole (CD). On a medium or large scale, the use of carbonyl diimidazole as coupling reagent is thought to give better yields and/or a cleaner reaction, compared to the use of pivaloyl chloride (trimethylacetyl chloride) or 2-propane phosphonic acid anhydride as a coupling reagent.

In process (b), more particularly, the activation of the 4-(tetrahydro-2H-pyran-4-yloxy)benzoic acid with the carbonyl diimidazole coupling reagent, and the subsequent reaction with 1-isopropyl piperazine, are both carried out in a reaction solvent comprising (or, in one particular embodiment, consisting essentially of) acetonitrile and/or propionitrile, more preferably acetonitrile.

When carbonyl diimidazole (CDI) is used as coupling reagent for activation of the 4-(tetrahydro-2H-pyran-4-yloxy)benzoic acid, followed by reaction with the 1-isopropyl piperazine, then the reaction conditions can in particular be as follows, independently and/or in any combination:
- the carbonyl diimidazole is typically present in 0.5 to 1.5 mole equivalents (with reference to the number of moles of the 4-(tetrahydro-2H-pyran-4-yloxy)benzoic acid), suitably 0.9 to 1.1 mole equivalents, preferably 1.0 to 1.1 mole equivalents, e.g. 1.1 mole equivalents; and/or
- the 1-isopropyl piperazine is typically present in 0.5 to 1.5 mole equivalents (with reference to the number of moles of the 4-(tetrahydro-2H-pyran-4-yloxy)benzoic acid), suitably 1.0 to 1.25 mole equivalents, preferably 1.1 to 1.2 mole equivalents, e.g. 1.15 or 1.2 mole equivalents; and/or
- the reaction (the activation of the 4-(tetrahydro-2H-pyran-4-yloxy)benzoic acid with CDI, or the subsequent reaction with 1-isopropyl piperazine, or both) is typically carried out in a suitable organic solvent such as a polar aprotic organic solvent, for example a solvent comprising (e.g. consisting essentially of) acetonitrile, propionitrile, dimethylsulfoxide, N,N-dimethylformamide (DMF), N-methylpyrrolidinone (NMP), and/or 1,4-dioxane; preferably the reaction solvent comprises (e.g. consists essentially of) acetonitrile and/or propionitrile, more preferably acetonitrile; and/or
- the reaction solvent is typically dry, although a small percentage of water in the reaction solvent can sometimes be tolerated; and/or
- when the reaction solvent is acetonitrile or propionitrile, the temperature of the reaction (for either the activation of the 4-(tetrahydro-2H-pyran-4-yloxy)benzoic acid with the carbonyl diimidazole, or for the subsequent reaction with the 1-isopropyl piperazine, or for both) can for example be from about 0° C. to the boiling point or reflux temperature of the solvent. The temperature of the activation reaction can e.g. be in the range of about 20 to about 40° C. (e.g. about 30° C.), e.g. followed by reaction with the 1-isopropyl piperazine at a temperature of from about 20° C. to the boiling point or reflux temperature of the reaction solvent (e.g. from about 40 to about 60° C., e.g. about 50° C.); this low activation reaction temperature can help to maximise yield due to decreased CDI decomposition, but any surviving excess CDI after the activation reaction is thought to then be more likely to react with the later-added 1-isopropyl piperazine to form a difficult-to-remove impurity which is thought to be 1-isopropyl-piperazin-4-yl-C(O)-imidazole or a salt thereof. Hence, it is currently thought preferable to activate the 4-(tetrahydro-2H-pyran-4-yloxy)benzoic acid with the carbonyl diimidazole at a temperature of from about 50° C. to the boiling point/reflux temperature of the reaction solvent or from about 60° C. to the boiling/reflux temperature (e.g. about 60 to about 70° C., e.g. 65 to 70° C., e.g. in acetonitrile solvent), and optionally also to have this temperature range (from about 50° C. to the boiling point/reflux temperature, e.g. about 60 to about 70° C.) as the temperature for the subsequent reaction with the 1-isopropyl piperazine, e.g. in order to potentially reduce this impurity; and/or
- the 4-(tetrahydro-2H-pyran-4-yloxy)benzoic acid and the carbonyl diimidazole are typically reacted together (e.g. with stirring) for at least 0.5 hours, suitably for at least 2 hours, e.g. for 0.5 to 5 hours such as 0.5 to 3 hours, e.g. for 2 to 5 hours or 2 to 3 hours, before the 1-isopropyl piperazine is mixed with the activated 4-(tetrahydro-2H-pyran-4-yloxy)benzoic acid; and/or
- the product of activation of the 4-(tetrahydro-2H-pyran-4-yloxy)benzoic acid by the carbonyl diimidazole, and the 1-isopropyl piperazine, are typically reacted together (e.g. with stirring) for at least 0.5 hours (e.g. 0.5 to 24 hours), suitably for at least 1 hour (e.g. 1 to 3 hours), such as for at least 2 hours (e.g. 2 to 3 hours).

General Process for Preparation of a Salt (e.g. Hydrochloride Salt) of 1-(1-methylethyl)-4-{[4-(tetrahydro-2H-pyran-4-yloxy)phenyl]carbonyl}piperazine:

To prepare, crystallise and isolate a salt (e.g. hydrochloride) of the compound of the invention, in one embodiment, at the end of the reaction in which the 4-(tetrahydro-2H-pyran-4-yloxy)benzoic acid has been activated by a coupling reagent (e.g. carbonyl diimidazole) followed by reaction of the activated acid with the 1-isopropyl piperazine, in a reaction solvent such as acetonitrile or propionitrile, the following process can be carried out:

the volume of reaction solvent (e.g. acetonitrile or propionitrile) is reduced under reduced pressure, e.g. to about 2-5 volumes e.g. about 3 volumes (e.g. of acetonitrile or propionitrile), and then a solution of the appropriate salt-forming acid (e.g. HCl) in a suitable solvent (e.g. a crystallisation solvent as defined below e.g. isopropanol) (e.g. to prepare the hydrochloride salt: this can be HCl in isopropanol, e.g. 5 to 6 N HCl in isopropanol, e.g. ca. 0.9 volumes thereof) is added to the reaction mixture; with preferably the appropriate salt-forming acid e.g. HCl being added in an amount of 0.5 to 1.3 mole equivalents such as 0.85 to 1.05 mole equivalents e.g. 1.0 mole equivalents with respect to the molar amount of the 4-(tetrahydro-2H-pyran-4-yloxy)benzoic acid used), and preferably, before or after or at the same time as the addition of the appropriate salt-forming acid, a crystallisation solvent is added (wherein the crystallisation solvent can e.g. comprise or be: an alcohol being a $C_{1-3}$ alcohol or n-butanol (including mixtures of alcohols), for example isopropanol, n-propanol, n-butanol, ethanol, or methanol; a mixture of water and an alcohol being a $C_{1-3}$ alcohol or n-butanol, for example isopropanol:water, ethanol:water, or methanol:water; isopropyl acetate; ethyl acetate; a $C_{3-6}$ ketone such as methyl isobutyl ketone (MIBK), methyl ethyl ketone, or acetone; acetonitrile; or dichloromethane; and wherein suitably the crystallisation solvent comprises or is an alcohol being a $C_{1-3}$ alcohol or n-butanol (including mixtures of alcohols), or a mixture of water and an alcohol being a $C_{1-3}$ alcohol or n-butanol; such as preferably: isopropanol, isopropanol:water such as ca. 2-10% e.g. ca. 2-5% e.g. ca. 5% water in isopropanol, or ethanol:water such as ca. 1-5% water in ethanol or industrial methylated spirits) (e.g. 6 to 20 volumes, e.g. ca. 12 volumes of the crystallisation solvent can e.g. be added), and the solvent-containing mixture comprising the salt (e.g. HCl salt) product is at, or is heated to, a temperature of about 50° C. to the boiling point or reflux temperature of the solvent (e.g. about 50-75° C., e.g. about 60-70° C., e.g. about 60-65° C.), and the salt (e.g. hydrochloride salt) of the 1-(1-methylethyl)-4-{[4-(tetrahydro-2H-pyran-4-yloxy)phenyl]carbonyl}piperazine is allowed or caused to crystallise or recrystallise from the hot mixture (e.g. by cooling the hot mixture), and the crystalline salt (e.g. hydrochloride salt) of the 1-(1-methylethyl)-4-{[4-(tetrahydro-2H-pyran-4-yloxy)phenyl]carbonyl}piperazine is isolated from the solvent (e.g. by filtration), and is usually dried (e.g. by drying under reduced pressure at about 40-60° C. e.g. about 50° C., or e.g. by drying at room temperature e.g. under suction or a stream of gas such as air or nitrogen).

For the hydrochloride (e.g. monohydrochloride) salt of 1-(1-methylethyl)-4-{[4-(tetrahydro-2H-pyran-4-yloxy)phenyl]carbonyl}piperazine, without being bound be theory, it appears, from preliminary experiments on the above-mentioned types of HCl-salt-formations and crystallisations, that crystalline Form 1 often tends to be the kinetic product of the salt-forming process, and that crystalline Form 2 is the thermodynamic product (i.e. thermodynamically more stable product). Crystalline Form 1 (or a predominance of crystalline Form 1) is often formed initially depending on the conditions, but, depending on the conditions (such as the type of solvent and the solubility of crystalline Form 1 in it, and/or the temperature and/or temperature time course, and/or the contact time of the crystalline Form 1 with the solvent), the crystalline Form 1 can then often convert to crystalline Form 2 to a greater or lesser extent when in contact with a suitable solvent i.e. a solvent suitable for converting crystalline Form 1 to crystalline Form 2.

The invention, in one aspect, therefore provides a process for preparing crystalline Form 2 of 1-(1-methylethyl)-4-{[4-(tetrahydro-2H-pyran-4-yloxy)phenyl]carbonyl}piperazine hydrochloride (e.g. monohydrochloride), comprising: converting crystalline Form 1 to crystalline Form 2 by contacting crystalline Form 1 with a suitable conversion solvent, for example by slurrying crystalline Form 1 in the suitable conversion solvent, for a sufficient time and/or at a sufficiently-high temperature to effect conversion of crystalline Form 1 to crystalline Form 2. The suitable conversion solvent typically comprises (e.g. consists essentially of) a $C_{1-3}$ alcohol or n-butanol or a mixture of water and an alcohol being a $C_{1-3}$ alcohol or n-butanol. The time and/or temperature required to effect conversion can e.g. depend on the solvent and the solubility of Form 1 in it. In the conversion process, the crystalline product of the process is suitably substantially (e.g. 70% or more or 80% or more or 90% or more or 95% or more by weight or molarity) in the form of crystalline Form 2 in terms of crystal form purity.

In order to prepare crystalline Form 1 of 1-(1-methylethyl)-4-{[4-(tetrahydro-2H-pyran-4-yloxy)phenyl] carbonyl}piperazine hydrochloride, the above-mentioned HCl-salt-formation process suitably uses a crystallisation solvent such as solvent comprising a $C_{1-3}$ alcohol or n-butanol or a mixture of water and an alcohol being a $C_{1-3}$ alcohol or n-butanol, in particular isopropanol, n-propanol, n-butanol, ethanol or a mixture thereof, and after formation, the 1-(1-methylethyl)-4-{[4-(tetrahydro-2H-pyran-4-yloxy)phenyl]carbonyl}piperazine hydrochloride (e.g. monohydrochloride) is allowed or caused to crystallise from the hot mixture by cooling the hot mixture, e.g. to about 0 to about 25° C., over a period of 2-4 hours or less (e.g. over 1.5-3 hours or less, e.g. over ca. 1.5 hours) measured from the onset of crystallisation, and the crystalline hydrochloride salt of the 1-(1-methylethyl)-4-{[4-(tetrahydro-2H-pyran-4-yloxy)phenyl] carbonyl}piperazine comprising crystalline Form 1 is isolated from the solvent after no more than 6 hours (preferably no more than 4 hours, e.g. no more than 2-3 hours, e.g. ca. 1.5 hours), of contact time with the solvent measured from the onset of crystallisation.

In order to prepare crystalline Form 2 of 1-(1-methylethyl)-4-{[4-(tetrahydro-2H-pyran-4-yloxy)phenyl] carbonyl}piperazine hydrochloride, e.g. by conversion of Form 1 into Form 2, (i) the above-mentioned HCl-salt-formation process uses a crystallisation solvent (e.g. an alcohol being a $C_{1-3}$ alcohol or n-butanol (including mixtures of alcohols), or a mixture of water and an alcohol being a $C_{1-3}$ alcohol or n-butanol; in particular isopropanol, n-propanol, n-butanol, ethanol, methanol, isopropanol:water, ethanol:water, or methanol:water; preferably isopropanol, or isopropanol:water such as ca. 2-10% e.g. ca. 2-5% e.g. ca. 5% water in isopropanol, or ethanol:water such as ca. 1-5% water in ethanol or industrial methylated spirits); and (ii)(a) in the event that the crystallisation solvent is methanol, isopropanol:water, n-propanol:water, n-butanol:water, ethanol:water, or methanol:water, then after formation the 1-(1-methylethyl)-4-{[4-(tetrahydro-2H-pyran-4-yloxy)phenyl]carbonyl}piperazine hydrochloride (e.g. monohydrochloride) is allowed or caused to crystallise or recrystallise from the hot mixture (e.g. at about 50-75° C., e.g. ca. 60-70° C., e.g. ca. 60-65° C.), by cooling the hot mixture, e.g. to about 0 to about 30° C., over a period of 4 hours or more (e.g. 5-6 hours or more) measured from the onset of crystallisation (preferably using gradual cooling); and optionally, before cooling, by ageing the mixture of the salt and the solvent (e.g. slurry) at a temperature of about 50° C. to the boiling point or reflux temperature of the solvent (e.g. at about 50-75° C., e.g. ca. 60-70° C., e.g. ca. 60-65° C.) for 0.5 hours or more (e.g. for 1 hour or more, e.g. 1-3 hours, or for 2 hours or more e.g. ca. 2 hours) measured from the onset of crystallisation; or (ii)(b) in the event that the crystallisation solvent is ethanol, isopropanol, n-propanol or n-butanol, then after formation the 1-(1-methylethyl)-4-{[4-(tetrahydro-2H-pyran-4-yloxy)phenyl]carbonyl}piperazine hydrochloride (e.g. monohydrochloride) is allowed or caused to crystallise or recrystallise from the hot mixture, and the mixture of the salt and the solvent (e.g. a slurry) is aged at a temperature of about 50° C. to the boiling point or reflux temperature of the solvent (e.g. at about 50-75° C., e.g. ca. 60-75° C., e.g. ca. 60-70° C.) for 6 hours or more (e.g. for 10 hours or more, e.g. for 15 hours or more, e.g. for about 18-24 hours) measured from the onset of crystallisation; and then the hot mixture is cooled, e.g. to about 0 to about 30° C., e.g. using gradual cooling;

and (iii) the crystalline hydrochloride salt of the 1-(1-methylethyl)-4-{[4-(tetrahydro-2H-pyran-4-yloxy)phenyl]carbonyl}piperazine, substantially (e.g. 80% or more or 90% or more or 95% or more by weight or molarity) in the form of crystalline Form 2, is isolated from the solvent (e.g. by filtration), and is usually dried (e.g. by drying under reduced pressure at about 40-60° C. e.g. about 50° C., or e.g. by drying at room temperature e.g. under suction or a stream of gas such as air or nitrogen).

Synthetic Processes, Continued 4-(Tetrahydro-2H-pyran-4-yloxy)benzoyl chloride (V) or 4-(tetrahydro-2H-pyran-4-yloxy)benzoic acid (IV) may be prepared in accordance with the following scheme wherein P represents a suitable protecting group, such as $C_{1-6}$ straight-chain alkyl (e.g. methyl, ethyl, n-propyl or n-butyl) or isopropyl or isobutyl, or benzyl; such as methyl or ethyl; in particular methyl.

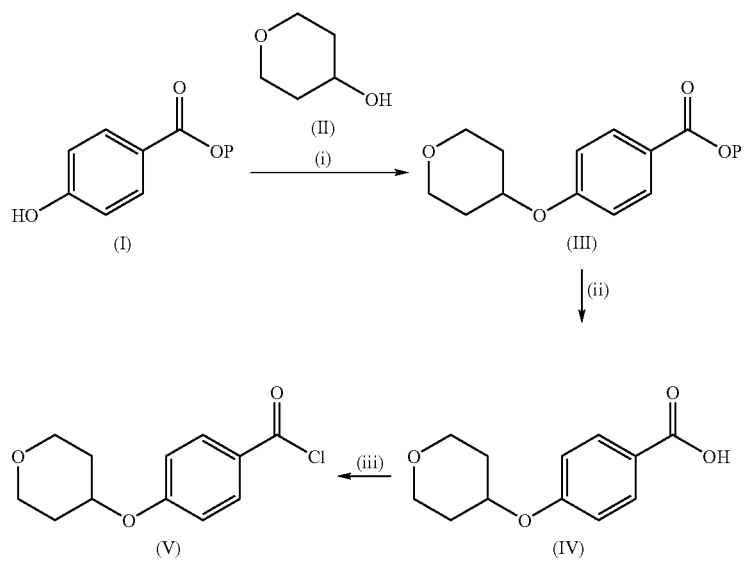

Step (i) typically comprises the use of a phosphine such as triphenylphosphine in a suitable solvent such as tetrahydrofuran, toluene and/or xylene (wherein "xylene" can be o-xylene, m-xylene, p-xylene, or a mixture of xylenes), followed by the addition (e.g. slow and/or dropwise addition) of an azodicarboxylate such as diethyl azodicarboxylate or diisopropyl azodicarboxylate, at a suitable temperature, for example, from room temperature to about 80° C., e.g. room temperature. Reaction times (including any azodicarboxylate addition time) can be e.g. from 0.5 to 72 hours. When using tetrahydrofuran as reaction solvent, room temperature can be used, and the reaction time is for example from 3 to 72 hours. When the reaction solvent comprises or consists essentially of toluene and/or xylene, in particular toluene, a reaction temperature of about 40 to about 80° C., e.g. about 40 to about 70° C., e.g. about 55° C., can be used; and/or a reaction time (including any azodicarboxylate addition time) of about 0.5 to 6 hours, e.g. 0.5 to 3 hours, e.g. 1-2 hours, can be used. In a particular embodiment, the reaction solvent comprises or consists essentially of toluene and/or xylene, preferably toluene, and reaction step (i) uses triphenylphosphine and diisopropyl azodicarboxylate; in which case suitably the heated (e.g. ca. 40-70° C.) reaction mixture can be cooled (e.g. to −10 to 25° C., e.g. to ca. 0-5° C., provided that it is not cooled to the melting point of the solvent or below), e.g. for 0.5 to 2 hours, and then the solid biproduct formed is removed e.g. by filtration. The use of toluene as reaction solvent helps to crystallise out the biproduct adduct of triphenylphosphine oxide and diisopropyl hydrazinedicarboxylate from the solution (especially when the reaction mixture is seeded with this adduct e.g. after cooling), which helps to reduce the levels of triphenylphosphine oxide in the crude product (III).

When using toluene and/or xylene as a solvent in reaction step (i), in one embodiment, the reaction product compound of formula (III) is not isolated. Optionally, in this embodiment, the toluene and/or xylene solution of the compound of formula (III) is used directly in the subsequent reaction (deprotection e.g. hydrolysis) step (ii), in particular when $C_{1-6}$ straight-chain alkyl (e.g. methyl, ethyl, n-propyl or n-butyl) or isopropyl or isobutyl and the subsequent step (ii) comprises alkaline (e.g. NaOH or KOH) hydrolysis of the ester.

According to a further aspect of the invention, there is provided a process for preparing a compound of formula (III)

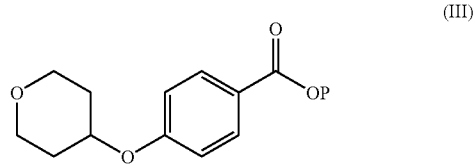

(III)

wherein P represents a protecting group such as $C_{1-6}$ straight-chain alkyl (e.g. methyl, ethyl, n-propyl or n-butyl) or isopropyl or isobutyl, or benzyl (in particular $C_{1-6}$ straight-chain alkyl or isopropyl, e.g. methyl or ethyl), wherein the process comprises:
(i) reacting the compound of formula (I)

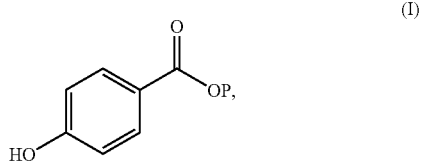

(I)

wherein P represents the protecting group as defined for the compound of formula (III), with 4-hydroxytetrahydropyran of formula (II) or a derivative thereof in which its OH group is activated;
wherein the reaction step (i) is carried out in a reaction solvent comprising or consisting essentially of toluene and/or xylene (in particular toluene).
"Xylene" can be o-xylene, m-xylene, p-xylene, or a mixture of xylenes.
In this process aspect of the invention using a step (i) reaction solvent comprising toluene and/or xylene, the reaction conditions for step (i) can in particular be as described herein for step (i) for the general synthetic processes. In particular, reaction step (i) can use triphenylphosphine and diisopropyl azodicarboxylate. For a step (i) reaction solvent comprising toluene and/or xylene, in particular toluene, a reaction temperature of about 40 to about 80° C., e.g. about 40 to about 70° C., e.g. about 55° C., can be used; and/or a reaction time (including any azodicarboxylate addition time) of about 0.5 to 6 hours, e.g. 0.5 to 3 hours, e.g. 1-2 hours, can be used. In a particular embodiment, when the step (i) reaction solvent comprises toluene and/or xylene, preferably toluene, and reaction step (i) uses triphenylphosphine and diisopropyl azodicarboxylate, the heated (e.g. ca. 40-70° C.) reaction mixture can be cooled (e.g. to −10 to 25° C., e.g. to ca. 0-5° C., provided that it is not cooled to the melting point of the solvent or below), e.g. for 0.5 to 2 hours, and then the solid biproduct (the adduct of triphenylphosphine oxide and diisopropyl hydrazinedicarboxylate) formed is removed e.g. by filtration. In particular, the reaction mixture can be seeded with the adduct of the adduct of triphenylphosphine oxide and diisopropyl hydrazinedicarboxylate, e.g. after cooling the reaction mixture. The use of toluene as reaction solvent helps to crystallise out the biproduct adduct of triphenylphosphine oxide and diisopropyl hydrazinedicarboxylate from the solution (especially when the reaction mixture is seeded with this adduct e.g. after cooling), which helps to reduce the levels of triphenylphosphine oxide in the crude product (III).

For the aspect of the invention being a process for preparing a compound of formula (III), using a step (i) reaction solvent comprising toluene and/or xylene; there is also provided a process for preparing a compound of formula (IV), which is 4-(tetrahydro-2H-pyran-4-yloxy)benzoic acid, comprising:
performing step (i) using a reaction solvent comprising or consisting essentially of toluene and/or xylene, and then,
(ii) converting the compound of formula (III) to the compound of formula (IV); e.g. by hydrolysing the ester within the compound of formula (III) when P represents $C_{1-6}$ straight-chain alkyl (e.g. methyl, ethyl, n-propyl or n-butyl) or isopropyl or isobutyl (in particular methyl or ethyl), e.g. under alkaline conditions (e.g. using sodium hydroxide or potassium hydroxide, e.g. aqueous), or e.g. by hydrogenation when P represents benzyl. In this process aspect of the invention, there is also provided a process for the preparation of 1-(1-methylethyl)-4-{[4-(tetrahydro-2H-pyran-4-yloxy)phenyl]carbonyl}piperazine or a salt thereof, which process comprises:
performing step (i) using a reaction solvent comprising or consisting essentially of toluene and/or xylene; then
(ii) converting the compound of formula (III) to the compound of formula (IV), which is 4-(tetrahydro-2H-pyran-4-yloxy)benzoic acid, e.g. as described herein; and then
either a) converting the 4-(tetrahydro-2H-pyran-4-yloxy)benzoic acid to 4-(tetrahydro-2H-pyran-4-yloxy)benzoyl chloride and then reacting this with 1-isopropyl piperazine;
or b) reacting the 4-(tetrahydro-2H-pyran-4-yloxy)benzoic acid with 1-isopropyl piperazine, or converting the 4-(tetrahydro-2H-pyran-4-yloxy)benzoic acid to a non-acid-chloride derivative thereof in which the carboxylic acid group has been activated, and then reacting this with 1-isopropyl piperazine;
and optionally preparing a salt (e.g. pharmaceutically acceptable salt) of 1-(1-methylethyl)-4-{[4-(tetrahydro-2H-pyran-4-yloxy)phenyl]carbonyl}piperazine. Steps a) and/or b) can e.g. be as described herein.

Step (ii) is a deprotection reaction. When P represents $C_{1-6}$ straight-chain alkyl (e.g. methyl, ethyl, n-propyl or n-butyl)

or isopropyl or isobutyl (in particular methyl or ethyl), the reaction typically comprises treatment with a suitable alkali (e.g. aqueous), such as sodium hydroxide or potassium hydroxide (e.g. aqueous sodium hydroxide or potassium hydroxide solution), in a suitable solvent such as methanol (e.g. when P=Me), or ethanol (e.g. when P=Et), or toluene and/or xylene; e.g. at a suitable temperature, such as 70-100° C. (e.g. 95° C. or 80° C.) and/or at reflux, e.g. for 1 to 24 hours such as 2-6 hours or 2-3 hours; typically until the hydrolysis is substantially complete. In a particular embodiment, when the step (ii) reaction solvent is toluene and/or xylene, and the reaction comprises treatment with a suitable aqueous alkali such as aqueous sodium hydroxide or potassium hydroxide solution, the reaction comprises efficient (e.g. vigorous) stirring or mixing.

In a particular embodiment, a toluene and/or xylene solution containing the compound of formula (III), produced in step (i), is used directly in the subsequent hydrolysis step (ii), i.e. without isolation of the compound of formula (III), in particular when the subsequent step (ii) comprises alkaline (e.g. NaOH or KOH) hydrolysis of the ester. The reaction conditions for steps (i) and/or (ii) can in particular be as described herein, e.g. reaction step (i) can use triphenylphosphine and diisopropyl azodicarboxylate.

When P represents benzyl, the deprotection reaction (ii) can comprise hydrogenation.

According to another aspect of the invention, there is provided a process for preparing a compound of formula (IV)

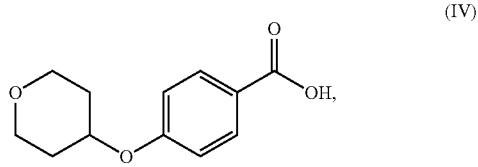

(IV)

which is 4-(tetrahydro-2H-pyran-4-yloxy)benzoic acid, wherein the process comprises:
(i) reacting the compound of formula (I), wherein P represents $C_{1-6}$ straight-chain alkyl (e.g. methyl, ethyl, n-propyl or n-butyl) or isopropyl or isobutyl (in particular methyl or ethyl), with 4-hydroxytetrahydropyran of formula (II) or a derivative thereof in which its OH group is activated, to prepare a compound of formula (III), wherein P has the same definition as in the compound of formula (I), and
(ii) hydrolysing the ester within the compound of formula (III), e.g. under alkaline conditions (e.g. using sodium hydroxide or potassium hydroxide, e.g. aqueous), to form the compound of formula (IV),
wherein the reaction steps (i) and (ii) are both carried out in a reaction solvent comprising or consisting essentially of toluene and/or xylene (in particular toluene). "Xylene" can be o-xylene, m-xylene, p-xylene, or a mixture of xylenes.

In a particular embodiment of this process aspect of the invention, the toluene and/or xylene solution of the compound of formula (III) produced in step (i) is used directly in the subsequent hydrolysis step (ii), i.e. without isolation of the compound of formula (III), in particular when the subsequent step (ii) comprises alkaline (e.g. NaOH or KOH) hydrolysis of the ester. The reaction conditions for steps (i) and/or (ii) can in particular be as described herein, e.g. reaction step (i) can use triphenylphosphine and diisopropyl azodicarboxylate. In a particular embodiment of this process aspect of the invention, there is also provided a process for the preparation of 1-(1-methylethyl)-4-{[4-(tetrahydro-2H-pyran-4-yloxy)phenyl]carbonyl}piperazine or a salt thereof, which process comprises:

performing steps (i) and (ii), wherein the reaction steps (i) and (ii) are both carried out in a reaction solvent comprising or consisting essentially of toluene and/or xylene, e.g. as described hereinabove; and then
either a) converting the 4-(tetrahydro-2H-pyran-4-yloxy)benzoic acid to 4-(tetrahydro-2H-pyran-4-yloxy)benzoyl chloride and then reacting this with 1-isopropyl piperazine;
or b) reacting the 4-(tetrahydro-2H-pyran-4-yloxy)benzoic acid with 1-isopropyl piperazine, or converting the 4-(tetrahydro-2H-pyran-4-yloxy)benzoic acid to a non-acid-chloride derivative thereof in which the carboxylic acid group has been activated, and then reacting this with 1-isopropyl piperazine;
and optionally preparing a salt (e.g. pharmaceutically acceptable salt) of 1-(1-methylethyl)-4-{[4-(tetrahydro-2H-pyran-4-yloxy)phenyl]carbonyl}piperazine.

Steps a) and/or b) can e.g. be as described herein.

Step (iii) typically comprises treatment with suitable chlorinating agent such as oxalyl chloride or thionyl chloride, e.g. in a suitable solvent (e.g. non-aqueous organic solvent) such as dichloromethane or ethyl acetate (suitably dichloromethane), or (for thionyl chloride) without solvent, at a suitable temperature, such as room temperature.

Compounds of formula (I) are either commercially available (for example, methyl 4-hydroxybenzoate is available from Aldrich), or they may be prepared from commercially available compounds using standard methodology. 1-Isopropyl piperazine and 4-hydroxytetrahydropyran are commercially available, e.g. from Aldrich.

Uses 1-(1-Methylethyl)-4-{[4-(tetrahydro-2H-pyran-4-yloxy)phenyl]carbonyl}piperazine or a pharmaceutically acceptable salt thereof has affinity for and is an antagonist and/or inverse agonist of the histamine H3 receptor, and for example has potentially useful therapeutic properties.

More particularly, 1-(1-methylethyl)-4-{[4-(tetrahydro-2H-pyran-4-yloxy)phenyl]carbonyl}piperazine or a pharmaceutically acceptable salt thereof has potential use in the treatment or prophylaxis (in particular treatment) of:

neurological diseases (e.g. in a mammal such as a human); such as: cognitive impairment(s), cognitive deficit, Alzheimer's disease, dementia (such as Lewy body dementia or vascular dementia), age-related memory dysfunction, epilepsy, migraine, Parkinson's disease, multiple sclerosis (including fatigue), fatigue (in particular fatigue in multiple sclerosis, fatigue in depression, fatigue in cancer or in cancer chemotherapy, or chronic fatigue syndrome) such as cognitive and/or psychological fatigue, stroke, pain of neuropathic origin (such as neuralgias e.g. post-herpetic neuralgia, neuritis, neuropathic back pain, allodynia, etc.), inflammatory pain (in particular chronic inflammatory pain such as pain in osteoarthritis or pain in rheumatoid arthritis or inflammatory back pain; or acute inflammatory pain), or sleep disorders (such as hypersomnolence, excessive daytime sleepiness, narcolepsy, or sleep deficits associated with Parkinson's disease, restless leg's syndrome and/or fatigue, especially in multiple sclerosis);
wherein cognitive impairment(s) can be cognitive impairment(s) in: Alzheimer's disease, dementia (e.g. Lewy body dementia or vascular dementia), mild cognitive impairment, or a related neurodegenerative disorder; or cognitive impairment(s) in Parkinson's disease, or cognitive impairment(s) in schizophrenia; or
psychiatric disorders (e.g. in a mammal such as a human); such as: psychotic disorders (such as schizophrenia or bipolar disorder), attention deficit hyperactivity disorder (ADHD), depression (including major depressive disorder), anxiety or addiction; or other diseases (e.g. in a mammal such as a human); such as obesity or a gastro-intestinal disorder.

Thus the invention also provides 1-(1-methylethyl)-4-{[4-(tetrahydro-2H-pyran-4-yloxy)phenyl]carbonyl}piperazine or a pharmaceutically acceptable salt thereof, for use as a therapeutic substance in the treatment or prophylaxis (in particular treatment) of any of the above disorders; in particular cognitive impairment(s), e.g. cognitive impairment(s) in a disease such as Alzheimer's disease, dementia (e.g. Lewy body dementia or vascular dementia), mild cognitive impairment, or a related neurodegenerative disorder, or cognitive impairment(s) in Parkinson's disease, or cognitive impairment(s) in schizophrenia; or fatigue; or a sleep disorder.

The invention also provides 1-(1-methylethyl)-4-{[4-(tetrahydro-2H-pyran-4-yloxy)phenyl]carbonyl}piperazine or a pharmaceutically acceptable salt thereof, for use as a therapeutic substance in the treatment or prophylaxis (in particular treatment) of any of the above disorders, in particular cognitive impairment(s), fatigue or a sleep disorder, in a mammal (e.g. rodent such as rat, or pig or human) such as a human.

The invention further provides a method of treatment or prophylaxis (in particular treatment) of any of the above disorders, e.g. a neurological disease, in a mammal such as a human, which comprises administering to the sufferer (the mammal in need thereof) a therapeutically effective amount of 1-(1-methylethyl)-4-{[4-(tetrahydro-2H-pyran-4-yloxy)phenyl]carbonyl}piperazine or a pharmaceutically acceptable salt thereof.

The invention further provides a method of treatment or prophylaxis (in particular treatment) of:
- cognitive impairment(s); e.g. cognitive impairment(s) in a disease such as Alzheimer's disease, dementia (e.g. Lewy body dementia or vascular dementia), mild cognitive impairment, or a related neurodegenerative disorder, or cognitive impairment(s) in Parkinson's disease, or cognitive impairment(s) in schizophrenia;
- or fatigue (in particular fatigue in multiple sclerosis, fatigue in depression, fatigue in cancer or in cancer chemotherapy, or chronic fatigue syndrome);
- or a sleep disorder (such as hypersomnolence, excessive daytime sleepiness, narcolepsy, or sleep deficits associated with Parkinson's disease, restless leg's syndrome and/or fatigue); in a mammal (e.g. rodent such as rat, or pig or human), such as a human, in need thereof, which comprises administering to the mammal a therapeutically effective amount of 1-(1-methylethyl)-4-{[4-(tetrahydro-2H-pyran-4-yloxy)phenyl]carbonyl}piperazine or a pharmaceutically acceptable salt thereof.

In another aspect, the invention provides the use of 1-(1-methylethyl)-4-{[4-(tetrahydro-2H-pyran-4-yloxy)phenyl]carbonyl}piperazine or a pharmaceutically acceptable salt thereof in the manufacture of a medicament for use in the treatment or prophylaxis (in particular treatment) of any of the above disorders, in particular a neurological disease and/or in particular cognitive impairment(s), fatigue or a sleep disorder.

In particular, the invention provides the use of 1-(1-methylethyl)-4-{[4-(tetrahydro-2H-pyran-4-yloxy)phenyl]carbonyl}piperazine or a pharmaceutically acceptable salt thereof in the manufacture of a medicament for use in the treatment or prophylaxis (in particular treatment) of any of the above disorders, in particular a neurological disease and/or in particular cognitive impairment(s), fatigue or a sleep disorder, in a mammal (e.g. rodent such as rat, or pig or human) such as a human.

More particularly, the invention provides the use of 1-(1-methylethyl)-4-{[4-(tetrahydro-2H-pyran-4-yloxy)phenyl]carbonyl}piperazine or a pharmaceutically acceptable salt thereof in the manufacture of a medicament:
- for use in the treatment or prophylaxis (in particular treatment) of cognitive impairment(s); e.g. cognitive impairment(s) in a disease such as Alzheimer's disease, dementia (e.g. Lewy body dementia or vascular dementia), mild cognitive impairment, or a related neurodegenerative disorder, or cognitive impairment(s) in Parkinson's disease, or cognitive impairment(s) in schizophrenia;
- or for use in the treatment or prophylaxis (in particular treatment) of fatigue (in particular fatigue in multiple sclerosis, fatigue in depression, fatigue in cancer or in cancer chemotherapy, or chronic fatigue syndrome);
- or for use in the treatment or prophylaxis (in particular treatment) of a sleep disorder (such as hypersomnolence, excessive daytime sleepiness, narcolepsy, or sleep deficits associated with Parkinson's disease, restless leg's syndrome and/or fatigue);
- e.g. in a mammal (e.g. rodent such as rat, or pig or human) such as a human.

Pharmaceutical Compositions, Doses, and Dosage Regimens

When used in therapy, the compound of the invention or a pharmaceutically acceptable salt thereof is usually formulated in a pharmaceutical composition. Such compositions can be prepared using various procedures.

Thus, the present invention further provides a pharmaceutical composition for use in the treatment or prophylaxis (e.g. treatment) of any of the above disorders, e.g. a neurological disease and/or cognitive impairment(s), fatigue or a sleep disorder, which comprises 1-(1-methylethyl)-4-{[4-(tetrahydro-2H-pyran-4-yloxy)phenyl]carbonyl}piperazine or a pharmaceutically acceptable salt thereof and a pharmaceutically acceptable carrier.

The present invention further provides a pharmaceutical composition which comprises 1-(1-methylethyl)-4-{[4-(tetrahydro-2H-pyran-4-yloxy)phenyl]carbonyl}piperazine or a pharmaceutically acceptable salt thereof and a pharmaceutically acceptable carrier.

A pharmaceutical composition of the invention, which may be prepared by admixture, for example at ambient temperature and/or atmospheric pressure, is usually adapted for oral, parenteral or rectal administration and, as such, may be in the form of a tablet, a capsule, an oral liquid preparation, a powder, granules, a lozenge, a reconstitutable powder, an injectable or infusible solution or suspension, or a suppository.

An orally administrable pharmaceutical composition, such as a tablet or capsule, is generally preferred.

A tablet or capsule for oral administration may be in unit dose form, and may contain one or more excipients, such as a binding agent (e.g. povidone, hydroxypropylmethylcellulose or starch), a filler (e.g. mannitol or lactose), microcrystalline cellulose, a lubricant e.g. tabletting lubricant (e.g. magnesium stearate, calcium stearate or stearic acid), a disintegrant e.g. tablet disintegrant, and/or a pharmaceutically acceptable wetting agent. A tablet may be coated, e.g. film-coated, e.g. according to a tablet coating method. A capsule can be a hard or soft capsule, containing the compound or salt of the invention and the one or more excipients e.g. in powder or pellet form.

An oral liquid preparation may be in the form of, for example, an aqueous or oily suspension, a solution, an emulsion, a syrup or elixir, or may be in the form of a dry product for reconstitution with water or other suitable vehicle before use. Such liquid preparations may contain additive(s) such as suspending agents, emulsifying agents, non-aqueous vehicles (which may include edible oils), and/or preservatives, and/or, if desired, flavourings and/or colorants.

For parenteral administration, fluid unit dosage forms are typically prepared utilising the compound of the invention or pharmaceutically acceptable salt thereof and a sterile vehicle.

The compound or salt, e.g. depending on the vehicle and/or concentration used, can be either suspended or dissolved in the vehicle. In preparing solutions, the compound or salt can be dissolved for injection and filter sterilised before filling into a suitable vial or ampoule and sealing. Adjuvant(s) such as a local anaesthetic, preservative(s) and/or buffering agent(s) can be dissolved in the vehicle. To enhance the stability, the composition can be frozen after filling into the vial and the water removed under vacuum. Parenteral suspensions are typically prepared in substantially the same manner, except that the compound or salt is suspended in the vehicle instead of being dissolved, and sterilisation typically is not accomplished by filtration. In one embodiment, the compound or salt is sterilised, e.g. by exposure to ethylene oxide, before suspension in a sterile vehicle. In one embodiment, a surfactant or wetting agent is included in the composition to facilitate uniform distribution of the compound or salt.

The pharmaceutical composition may contain from 0.1% to 99% by weight of the composition of the active material (i.e. the 1-(1-methylethyl)-4-{[4-(tetrahydro-2H-pyran-4-yloxy)phenyl]carbonyl}piperazine or the pharmaceutically acceptable salt thereof), in particular from 1 to 60% by weight or from 10 to 60% by weight of the composition of the active material. For example, this may vary depending on the route of administration and/or the composition's intended use(s).

The total amount of the pharmaceutically acceptable carrier in the pharmaceutical composition can for example vary depending on the pharmaceutical composition and/or its intended use and/or the route of administration. In one embodiment, the total amount of the pharmaceutically acceptable carrier in the pharmaceutical composition (e.g. or i.e. the total amount of the one or more excipients present therein, such as one or more of the excipient types mentioned herein), is in the range of from 1% to 99.9% by weight of the composition, for example from 40% to 99% by weight such as from 40% to 90% by weight of the composition. Additionally or alternatively, in one embodiment, for a composition (e.g. composition for oral administration, e.g. tablet or capsule) in unit dose form, the total amount of the pharmaceutically acceptable carrier in the unit dose form pharmaceutical composition (e.g. or i.e. the total amount of the one or more excipients present therein) can be from 10 mg to 2000 mg, for example from 20 mg to 1500 mg such as from 100 mg to about 1000 mg.

The dose, e.g. oral dose, of the 1-(1-methylethyl)-4-{[4-(tetrahydro-2H-pyran-4-yloxy)phenyl]carbonyl}piperazine or the pharmaceutically acceptable salt thereof, e.g. used in the treatment or prophylaxis of the aforementioned disorders/diseases/conditions and/or comprised in a pharmaceutical composition, can for example vary in the usual way with the seriousness of the disorders, the weight of the sufferer, and/or other similar factors. However, as a general guide, in one embodiment a suitable unit dose (e.g. oral unit dose) of 0.02 to 1000 mg or 0.05 to 1000 mg, for example 0.1 to 200 mg such as 1.0 to 200 mg, and/or for example 0.02 to 200 mg or 0.05 to 200 mg such as 0.05 to 45 mg or 0.1 to 45 mg, of the compound or the pharmaceutically acceptable salt of the invention (measured as the "free base" compound), may be used, for example in a pharmaceutical composition (e.g. in an oral pharmaceutical composition, and/or e.g. in a unit dose form) of the invention. In one embodiment, such a unit dose is for administration once a day, e.g. orally and/or to a mammal such as a human; alternatively such a unit dose may be for administration more than once a day, for example two or three times a day, e.g. orally and/or to a mammal such as a human. Such therapy may extend for a number of weeks, months or years.

One Embodiment of a Pharmaceutical Dosage Form

In one embodiment, the invention provides a pharmaceutical dosage form (e.g. orally-adminitrable dosage form) comprising:
a) 1-(1-methylethyl)-4-{[4-(tetrahydro-2H-pyran-4-yloxy)phenyl]carbonyl}piperazine or a pharmaceutically acceptable salt thereof (e.g. hydrochloride salt);
b) optionally a stabiliser, which reduces degradation of the 1-(1-methylethyl)-4-{[4-(tetrahydro-2H-pyran-4-yloxy)phenyl]carbonyl}piperazine or the salt thereof in the dosage form when compared to a dosage form lacking said stabiliser; and
c) a pharmaceutically acceptable excipient.

In one embodiment of this embodiment, the pharmaceutical dosage form (e.g. orally-adminitrable dosage form) comprises a carrier tablet, which carrier tablet is at least partially (e.g. partially or wholly, e.g. only partially) covered by a film comprising:
a) 1-(1-methylethyl)-4-{[4-(tetrahydro-2H-pyran-4-yloxy)phenyl]carbonyl}piperazine or a pharmaceutically acceptable salt thereof (e.g. hydrochloride salt), and
b) optionally a stabiliser that reduces degradation of the 1-(1-methylethyl)-4-{[4-(tetrahydro-2H-pyran-4-yloxy)phenyl]carbonyl}piperazine or the salt thereof in the dosage form, when compared to a dosage form lacking said stabiliser.

In this embodiment, the term "carrier tablet" refers to a pharmaceutically acceptable tablet substantially free of the 1-(1-methylethyl)-4-{[4-(tetrahydro-2H-pyran-4-yloxy)phenyl]carbonyl}piperazine or the pharmaceutically acceptable salt thereof.

In one embodiment, the carrier tablet is formed by direct compression technology.

In one embodiment, the carrier tablet comprises:
a diluent (e.g. in an amount of from 50 to 100%, e.g. from 80 to 98%, by weight of the carrier tablet), such as microcrystalline cellulose e.g. microcrystalline cellulose having a nominal mean particle size of about 50 microns (e.g. Avicel PH-101™) or 100 microns (e.g. Avicel PH-102™), or lactose, or mannitol; and/or
a binding agent (e.g. in an amount of from 0.5 to 15%, e.g. from 2 to 10%, by weight of the carrier tablet), such as starch (e.g. corn starch, potato starch or pre-gelatinised starch), polyvinylpyrrolidone (povidone), or hydroxypropylmethylcellulose; and/or
a lubricant (e.g. in an amount of from 0.1 to 5%, e.g. from 0.3 to 3%, by weight of the carrier tablet), such as magnesium stearate, calcium stearate or stearic acid.

In one embodiment, the carrier tablet is a tablet comprising microcrystalline cellulose (e.g. Avicel PH-102™) (e.g. at 90% by weight of the carrier tablet), pregelatinized starch (e.g. Starch 1500™) (e.g. at 9% by weight of the carrier tablet), and magnesium stearate (e.g. at 1% by weight of the carrier tablet).

The above-mentioned pharmaceutical dosage form comprising the optional stabiliser, can for example contain from 0.02 mg to 2 mg (e.g. 0.05 mg to 1 mg) of the 1-(1-methylethyl)-4-{[4-(tetrahydro-2H-pyran-4-yloxy)phenyl]carbonyl}piperazine or the pharmaceutically acceptable salt thereof (e.g. hydrochloride salt), when measured as the amount of free base present.

In one embodiment, the dosage form does not comprise a stabiliser.

In a particular embodiment, the dosage form does comprise a stabiliser.

In the above-mentioned pharmaceutical dosage form(s), the stabiliser can typically comprise citric acid or a salt thereof, malic acid or a salt thereof, ascorbic acid or a salt thereof, sodium bicarbonate, optionally butylated hydroxyanisole and/or butylated hydroxytoluene. In one particular embodiment, the stabiliser comprises optionally butylated hydroxyanisole, such as butylated hydroxyanisole, or, more particularly, citric acid or a salt thereof, such as citric acid. In the dosage form, the molar ratio of the citric acid or the salt thereof (measured as citric acid) to the 1-(1-methylethyl)-4-{[4-(tetrahydro-2H-pyran-4-yloxy)phenyl]carbonyl}piperazine or the salt thereof (measured as the free base) can for example be from 550:1 to 1:2, such as from 500:1 to 2:3.

In one embodiment, the carrier tablet is coated with a carrier tablet film coat, e.g. to a 2-6% weight gain, for example using a coating not soluble in water (or not soluble in methanol or ethanol), for example using ethylcellulose (e.g. Surelease™) or methacrylic acid copolymer (e.g. Eudragit™) as the carrier tablet film coat. The film covering the carrier tablet and comprising the compound or salt of the invention and the optional stabiliser is typically outside of and/or coated onto the carrier tablet film coat.

In one embodiment, in the above-mentioned dosage form comprising the optional stabiliser, there is substantially no absorption of the 1-(1-methylethyl)-4-{[4-(tetrahydro-2H-pyran-4-yloxy)phenyl]carbonyl}piperazine or the pharmaceutically acceptable salt thereof by the carrier tablet.

The carrier tablet can in particular have one or more recesses or depressions. In a particular embodiment, the film (which at least partially, e.g. only partially, covers the carrier tablet and which comprises the compound or salt of the invention and the optional stabiliser) is substantially present within the one or more recesses or depressions of the carrier tablet.

In one embodiment, the above-mentioned dosage form (e.g. comprising a carrier tablet at least partially covered by a film comprising the compound or salt of the invention and an optional stabiliser) is further coated with an outer film coating.

In another aspect of this embodiment, the invention provides a method for preparing the above-mentioned pharmaceutical dosage form (comprising a carrier tablet at least partially covered by a film comprising the compound or salt of the invention and an optional stabiliser), wherein the method comprises dispensing a solution or suspension of 1-(1-methylethyl)-4-{[4-(tetrahydro-2H-pyran-4-yloxy)phenyl]carbonyl}piperazine or a pharmaceutically acceptable salt thereof and a stabiliser (e.g. citric acid or a salt thereof, e.g. present at about 2-3% w/v) onto a carrier tablet. Any solvent may be used provided that the stabiliser and any other excipients present in the film (which is to at least partially cover the carrier tablet) are soluble in the solvent. The solvent is typically volatile. The solvent should be pharmaceutically acceptable in any (residual) quantities in which it appears in the finished dosage form. The solvent used in the method can include water, and/or an organic solvent such as methanol, ethanol, acetone, acetic acid and/or dichloromethane. A mixture of solvents (e.g. water-ethanol) may be used. In one embodiment, the solvent is methanol.

In the method for preparing the dosage form, the carrier tablet and the dispensed solution or suspension may be heated (e.g. in a forced air oven) to evaporate excess liquid and may result in the formation of a film upon at least a part of the surface of the carrier tablet. The dosage form may then optionally be film coated, e.g. according to known methods, to create an outer film coating.

The carrier tablet used in the method for preparing the dosage form may have a recess or depression that provides a basin for the solution or suspension of the 1-(1-methylethyl)-4-{[4-(tetrahydro-2H-pyran-4-yloxy)phenyl]carbonyl}piperazine or the pharmaceutically acceptable salt thereof and the stabiliser to land after being dispensed. Typically, biconcave tablets having recesses on two faces of the tablet are employed.

In one optional embodiment, the above-mentioned dosage form comprising a carrier tablet of the present invention is produced by an apparatus described in WO 2005/123569, and more particularly is produced by an apparatus containing a dispensing module for accurately dispensing a predetermined amount of the solution or suspension of the 1-(1-methylethyl)-4-{[4-(tetrahydro-2H-pyran-4-yloxy)phenyl]carbonyl}piperazine or the pharmaceutically acceptable salt thereof and the stabiliser onto the carrier tablets. The apparatus may also have a holding member for holding the carrier tablets, which may move continually along the apparatus as the dispensing module dispenses the solution or suspension onto each of the carrier tablets. The apparatus may also have a drying system that dries or evaporates solvent from the solution or suspension deposited on each of the carrier tablets. The holding member may move continually along the apparatus as the drying system dries the dosage on each of the carrier tablets. The drying system may dry the dosage form by use of heated air, or by infrared or microwave heating. The apparatus may also have a coating system that applies an outer film coating over the dosage form.

Combinations 1-(1-Methylethyl)-4-{[4-(tetrahydro-2H-pyran-4-yloxy)phenyl]carbonyl}piperazine or a pharmaceutically acceptable salt thereof may be used in combination with other therapeutic agents. When 1-(1-methylethyl)-4-{[4-(tetrahydro-2H-pyran-4-yloxy)phenyl]carbonyl}piperazine or a pharmaceutically acceptable salt thereof is intended for use in the treatment or prophylaxis (in particular treatment) of Alzheimer's disease, dementia, mild cognitive impairment, or a related neurodegenerative disorder, in particular in the treatment or prophylaxis (in particular treatment) of cognitive impairment(s) in Alzheimer's disease, dementia (e.g. Lewy body dementia or vascular dementia), mild cognitive impairment, or a related neurodegenerative disorder, e.g. in a mammal such as a human, it may be used in combination with medicaments claimed to be useful as either disease modifying or symptomatic treatments of Alzheimer's disease, dementia, mild cognitive impairment, or a related neurodegenerative disorder. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil e.g. donepezil hydrochloride, rivastigmine, or galantamine e.g. galantamine hydrobromide), nicotinic receptor agonists or allosteric modulators (such as $\alpha 7$ agonists or allosteric modulators or $\alpha 4\beta 2$ agonists or allosteric modulators), PPAR agonists (such as PPAR$\gamma$ agonists), 5-HT$_4$ receptor partial agonists, 5-HT$_6$ receptor antagonists [such as 3-(phenylsulfonyl)-8-(1-piperazinyl)quinoline or a salt thereof, e.g. disclosed in WO03/080580 as the hydrochloride salt (Example 2) and as the free base (Example 16)], 5HT1A receptor antagonists, NMDA receptor antagonists or modulators (such as memantine e.g. memantine hydrochloride), or disease modifying agents such as $\beta$ or $\gamma$-secretase inhibitors.

When 1-(1-methylethyl)-4-{[4-(tetrahydro-2H-pyran-4-yloxy)phenyl]carbonyl}piperazine or a pharmaceutically acceptable salt thereof is intended for use in the treatment of narcolepsy, it may be used in combination with medicaments claimed to be useful as treatments for narcolepsy. Suitable examples of such other therapeutic agents include modafinil, armodafinil and monoamine uptake blockers.

When 1-(1-methylethyl)-4-{[4-(tetrahydro-2H-pyran-4-yloxy)phenyl]carbonyl}piperazine or a pharmaceutically acceptable salt thereof is intended for use in the treatment of schizophrenia, it may be used in combination with medicaments claimed to be useful as treatments of schizophrenia including i) antipsychotics including typical antipsychotics (for example chlorpromazine, thioridazine, mesoridazine, fluphenazine, perphenazine, prochlorperazine, trifluoperazine, thiothixine, haloperidol, molindone or loxapine), atypical antipsychotics (for example clozapine, olanzapine, risperidone, quetiapine, ziprasidone, amisulpride or aripiprazole), glycine transporter 1 inhibitors and metabotropic receptor ligands; ii) drugs for extrapyramidal side effects, for example anticholinergics (such as benztropine, biperiden, procyclidine, or trihexyphenidyl) and dopaminergics (such as amantadine); iii) antidepressants including serotonin reuptake inhibitors (such as citalopram, escitalopram, fluoxetine, paroxetine, dapoxetine or sertraline), dual serotonin/noradrenaline reuptake inhibitors (such as venlafaxine, duloxetine or milnacipran), noradrenaline reuptake inhibitors (such as reboxetine), tricyclic antidepressants (such as amitriptyline, clomipramine, imipramine, maprotiline, nortriptyline or trimipramine), monoamine oxidase inhibitors (such as isocarboxazide, moclobemide, phenelzine or tranylcypromine), and others (such as buprorion, mianserin, mirtazepine, nefazodone or trazodone); iv) anxiolytics including benzodiazepines such as alprazolam or lorazepam; and v) cognitive enhancers for example cholinesterase inhibitors (such as tacrine, donepezil, rivastigmine or galantamine).

When the compound of the invention or a pharmaceutically acceptable salt thereof is used in combination with other therapeutic agents, the compounds may be administered either sequentially or simultaneously by any convenient route.

The invention thus provides, in a further aspect, a combination comprising 1-(1-methylethyl)-4-{[4-(tetrahydro-2H-pyran-4-yloxy)phenyl]carbonyl}piperazine or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When the compound of the invention or a pharmaceutically acceptable salt thereof is used in combination with a second therapeutic agent active against the same disease state the dose of each compound may differ from that when the compound is used alone.

EXPERIMENTAL SECTION

The following Descriptions and Examples illustrate the compound of the invention, its hydrochloride salt, preparations thereof, and intermediates ("Descriptions") of use in the preparation thereof.

Description 1

Methyl 4-(tetrahydro-2H-pyran-4-yloxy)benzoate (D1)

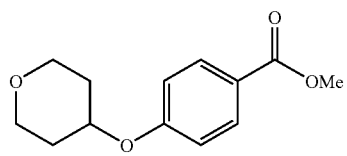

Method A

A stirred solution of methyl 4-hydroxybenzoate (1.49 g, 9.8 mmol, e.g. available from Aldrich), 4-hydroxytetrahydropyran (1 g, 9.8 mmol, e.g. available from Aldrich) and triphenylphosphine (3.85 g, 14.7 mmol) in tetrahydrofuran (60 ml) at room temperature was treated dropwise with diethyl azodicarboxylate (2.32 ml, 1.5 mole equivalents). The reaction was stirred overnight. The solvent was evaporated off, and the crude product was re-dissolved in ethyl acetate (50 ml), washed with 5% sodium carbonate solution (2×40 ml), water (3×40 ml), brine (40 ml), dried (magnesium sulfate) and evaporated. The crude product was loaded onto a silica column and was subjected to flash chromatography, eluting with a 10% to 30% gradient of ethyl acetate in light petroleum (40°-60° C.) to yield the title compound (2.12 g).

Method B

Diisopropyl azodicarboxylate (7.8 ml, 39.6 mmol, 2 mole equivalents) was added to a stirred solution of methyl 4-hydroxybenzoate (3.0 g, 19.7 mmol), 4-hydroxytetrahydropyran (2.8 ml, 28.2 mmol, ca. 1.4 mole equivalents) and triphenylphosphine (10.3 g, 39.3 mmol, 2 mole equivalents) in tetrahydrofuran (120 ml). The reaction mixture was stirred at room temperature for 68 hours. The solvent was then removed in vacuo and the crude residue was dissolved in ethyl acetate (100 ml). The organic solution was then washed with a saturated aqueous solution of sodium hydrogen carbonate (40 ml), water (40 ml) and brine (40 ml). The organic phase was dried (phase-separating column) and concentrated. The crude residue was purified by silica gel chromatography eluting with a gradient of from 0% to 30% ethyl acetate in hexane to yield the title compound as a pale yellow oil (3.14 g) ($^1$H NMR in CDCl$_3$ suggested the product to be contaminated with a substantial amount of diisopropyl azodicarboxylate residue).

Method C

Diisopropyl azodicarboxylate (2.89 ml, 14.68 mmol, 1.5 mole equivalents) was added to a stirred solution of methyl 4-hydroxybenzoate (1.49 g, 9.80 mmol, 1.0 mole equivalents), 4-hydroxytetrahydropyran (1.00 g, 9.79 mmol, 1.0 mole equivalents) and triphenylphosphine (3.85 g, 14.68 mmol, 1.5 mole equivalents) in tetrahydrofuran (60 ml) at 0° C. The reaction mixture was warmed to room temperature and stirred for 21 hours. 4-Hydroxytetrahydropyran (0.3 ml), triphenylphosphine (1.11 g) and diisopropyl azodicarboxylate (0.9 ml) were added sequentially to the reaction mixture at room temperature and stirring was continued for 2 hours. The solvent was removed in vacuo and the residue was dissolved in ethyl acetate (50 ml). The organic phase was washed with a saturated aqueous solution of sodium hydrogen carbonate (30 ml), water (30 ml) and brine (30 ml). The organic phase was dried (phase-separating column) and concentrated. The crude residue was purified by silica gel chromatography eluting with a gradient of from 0% to 30% ethyl acetate in hexane to yield the title compound as a pale yellow oil (2.19 g) (contaminated with trace amount of diisopropyl azodicarboxylate residue).

Method D

To a stirred solution of methyl 4-hydroxybenzoate (30 g, 197 mmol, 1.0 mole equivalents), tetrahydro-4-pyranol (24 ml, 251 mmol, 1.3 mole equivalents) and triphenylphosphine (78 g, 297 mmol, 1.5 mole equivalents) in tetrahydrofuran (600 ml) at room temperature, was added diisopropyl azodicarboxylate (58 ml, 298 mmol, 1.5 mole equivalents) over a period of 15 minutes. The reaction mixture was stirred for 24 hours at room temperature. Another portion of diisopropyl azodicarboxylate (5 ml) and tetrahydro-4-pyranol (2 ml) was added and the reaction mixture was stirred for another 2 hours at room temperature. The reaction mixture was then quenched by the addition of a saturated aqueous solution of sodium hydrogen carbonate (500 ml) and ethyl acetate (500 ml). The organic phase was washed with water (2×250 ml), dried (magnesium sulfate), and was then concentrated in vacuo to give the crude product, methyl 4-(tetrahydro-2H-pyran-4-yloxy)benzoate, as a thick yellow oil (182 g).

Description 2

4-(Tetrahydro-2H-pyran-4-yloxy)benzoic acid (D2)

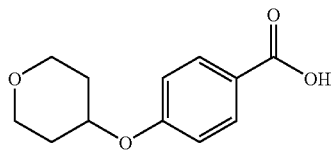

Method A

A stirred solution of methyl 4-(tetrahydro-2H-pyran-4-yloxy)benzoate (2.12 g; prepared as described in Description 1 Method A) in methanol (20 ml) at room temperature was treated with 1 M sodium hydroxide solution (17.9 ml, about 2 mole equivalents). The reaction mixture was refluxed for 4 hours and then cooled to room temperature. The methanol was evaporated off, and the aqueous mixture was washed with dichloromethane (3×10 ml) and then acidified to pH 2 with concentrated hydrochloric acid. The aqueous layer was extracted with ether (100 ml) and the ether solution was washed with water (3×50 ml), brine (50 ml), dried (magnesium sulfate) and evaporated to yield the title compound (1.27 g, contains ca. 15% of 4-hydroxybenzoic acid by NMR).

Alternatively, after the reaction is cooled to room temperature, the methanol is evaporated off, the aqueous mixture is washed with dichloromethane (3×10 ml) and then is acidified to pH 2 with concentrated hydrochloric acid, and then the product is filtered off directly.

Method B

To a stirred solution of methyl 4-(tetrahydro-2H-pyran-4-yloxy)benzoate (3.14 g, prepared as described in Description 1 Method B) in methanol (28 ml), was added a 1.0 M aqueous solution of sodium hydroxide (28 ml, 28 mmol). The reaction mixture was heated at 95° C. for 18 hours and was then cooled to room temperature. The methanol was removed in vacuo and the remaining aqueous phase was washed with dichloromethane (2×30 ml). The aqueous layer was then acidified to pH 2 using a 1.0 M aqueous solution of HCl. The resulting white precipitate was filtered off and dried (vacuum oven at 40° C. for 3 hours) to yield the title compound (1.52 g).

Method C

To a solution of methyl 4-(tetrahydro-2H-pyran-4-yloxy)benzoate (2.19 g, prepared as described in Description 1 Method C) in methanol (20 ml) at room temperature, was added a 1.0 M aqueous solution of sodium hydroxide (19 ml, 19 mmol). The reaction mixture was then heated at reflux for 15 hours. The reaction mixture was then cooled to room temperature and the methanol was removed in vacuo. The resulting aqueous phase was washed with dichloromethane (2×15 ml) and was then acidified to pH 2 using a 1.0 M aqueous solution of HCl. The resulting white precipitate was filtered off and dried (vacuum oven at 40° C. for 2 hours) to yield the title compound (1.32 g).

Method D

To a stirred solution of crude methyl 4-(tetrahydro-2H-pyran-4-yloxy)benzoate (182 g, prepared as described in Description 1 Method D) in methanol (800 ml), was added 1.0 M aqueous solution of sodium hydroxide (900 ml, 900 mmol). The reaction mixture was heated at 50° C. for 4 hours and was then cooled to room temperature. Methanol was removed in vacuo and the remaining aqueous phase was washed with ethyl acetate (2×400 ml). The aqueous phase was then acidified with 2.5 M aqueous HCl. The resultant white solid was filtered off to give the title compound (36.5 g).

Description 3

4-(Tetrahydro-2H-pyran-4-yloxy)benzoic acid (D3)

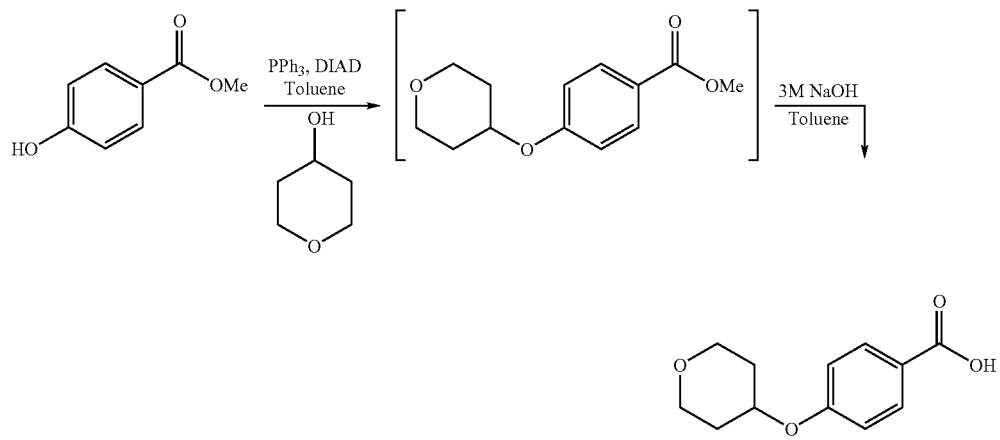

Short Summary Process Description

All weights, volumes ("vol") and equivalents are relative to methyl 4-hydroxybenzoate.

A solution of methyl 4-hydroxybenzoate (1 wt, 1 mole equivalent), triphenyl phosphine (2.6 wt, 1.5 mole equivalents), 4-hydroxytetrahydropyran (0.75 vol, 1.2 mole equivalents) in toluene (3.5 vol) under nitrogen is heated to 55° C. and diisopropyl azodicarboxylate (1.95 vol, 1.5 mole equivalents) is added dropwise over 60 minutes, maintaining the contents at 60±2° C. Following the addition, the reaction is stirred for 30 minutes, and then cooled to 0-5° C. The batch is then seeded with pre-prepared triphenylphosphine oxide-diisopropyl hydrazinedicarboxylate adduct, and then allowed to stir for a further 1 hour before filtering. The wet cake is washed with toluene (2×1 vol), and the combined mother liquors are transferred into a clean vessel. The toluene solution is washed with 2M sodium hydroxide solution (5 vol) at 0-5° C., and then 3M sodium hydroxide solution (5 vol) is added and the reaction is heated to 80° C. The reaction is stirred for at least 2.5 hours, until HPLC shows no starting material. The mixture is then cooled to 50° C. and toluene (5 vol) and water (5 vol) are added. The layers are allowed to separate, and the aqueous layer is washed with toluene (10 vol) and then acidified to pH1 with 2.5M HCl solution (7.5 vol). The resultant slurry is filtered and the wet cake is washed with water (2×2 vol). The title product is dried at about 50° C. in a vacuum oven with a nitrogen bleed to constant probe temperature.

Detailed Process Description
1. Added methyl 4-hydroxybenzoate (1 wt, 482.3 g, available from Fluka) to Vessel 1.
2. Added 4-hydroxytetrahydropyran (0.75 vol, 362 mL, 1.2 mole equivalents, available from Sigma-Aldrich) to Vessel 1.
3. Added triphenyl phosphine (2.6 wt, 1253 g, 1.5 mole equivalents) to Vessel 1.
4. Purged Vessel 1 with Nitrogen.
5. Added toluene (3.5 vol, 1690 mL) to Vessel 1.
6. Heated contents to 55° C. with stirring.
7. Added diisopropyl azodicarboxylate (DIAD, 1.95 vol, 940 mL, 1.5 mole equivalents, available from Aldrich) to Vessel 1 via a peristaltic pump over 2 hours maintaining the contents temperature at 60±2° C.
8. Stirred contents of Vessel 1 at 60±2° C. for 50 min.
9. Sampled reaction mixture for HPLC analysis.
10. Cooled contents of Vessel 1 to 0-5° C.
11. Seeded batch with triphenylphosphine oxide-diisopropyl hydrazinedicarboxylate adduct (0.001 wt, 0.482 g)
12. Stirred contents of Vessel 1 for 81 min.
13. Filtered off biproduct over 5 min on a PTFE minifilter fitted with Whatman No. 113 wet strengthened filter paper (rough side up). Used 20 L Buchner flask as receiver.
14. Washed wet cake with toluene (2×ca. 1 vol, 2×490 mL) and sucked cake free of solvent.
15. Combined filtrate and cake washes were transferred to Vessel 2 via PTFE suck-up line.
16. Cooled Vessel 2 contents to 0-5° C.
17. Added 2M sodium hydroxide solution (5 vol, 2400 mL) to Vessel 2.
18. Stirred contents of Vessel 2 at 0-5° C. for 5 min before allowing the layers to settle.
19. Ran the lower aqueous layer into a labelled Schott bottle.
20. Added 3M sodium hydroxide solution (5 vol, 2410 mL) to Vessel 2.
21. Heated contents to 80° C., and stirred for 2 hours 45 min.
22. Monitored reaction by HPLC until hydrolysis is complete.
23. Cooled contents of Vessel 2 to 50° C., and then added toluene (5 vol, 2410 mL) to Vessel 2.
24. Added water (5 vol, 2410 mL) to Vessel 2.
25. Stirred contents at 50±5° C. for 5 min before allowing the layers to settle.
26. Ran the lower aqueous layer into a labelled Schott bottle for retention.
27. Ran the upper organic layer into a labelled Schott bottle for disposal.
28. Recharged aqueous layer from labelled Schott bottle to Vessel 2.
29. Added toluene (ca. 10 vol, 4900 mL) to Vessel 2.
30. Stirred contents at 50±5° C. for 5 min before allowing the layers to settle.
31. Ran the lower aqueous layer into a labelled Schott bottle for retention.
32. Ran the upper organic layer into a labelled Schott bottle for disposal.
33. Recharged aqueous layer to Vessel 2.
34. Added 2.5M aqueous hydrochloric acid (7.5 vol, 3620 mL) via peristaltic pump until pH1 is achieved.
35. Stirred the resulting slurry for 15 min.
36. Filtered off product on a PTFE mini filter fitted with Whatman 113 wet strengthened filter paper (rough side up). 10 min filtration time.
37. Washed filter cake with water (2×2 vol, 970 mL).
38. Dried the solid product in polythene lined steel trays covered with a muslin cloth, under vacuum and a nitrogen bleed, at 50° C. overnight and at 75° C. for a further 3 days.
39. Title product was obtained as an off-white solid (568.9 g).

Analytical Data

1H NMR (400 MHz, DMSO-$d_6$) delta ppm 1.55-1.64 (m, 2 H) 1.95-2.03 (m, 2 H) 3.49 (ddd, J=11.74, 9.41, 2.57 Hz, 2 H) 3.85 (ddd, J=11.80, 4.34, 4.16 Hz, 2 H) 4.69 (ddd, J=8.56, 4.65, 4.40 Hz, 1 H) 7.03-7.09 (m, 2 H) 7.84-7.90 (m, 2 H), and 12.31 (br-s, 1H).

In an alternative to the above process, in step 37, the filter cake can be washed with toluene, instead of water, before the 50-75° C. vacuum drying of step 38.

Example 1

1-(1-Methylethyl)-4-{[4-(tetrahydro-2H-pyran-4-yloxy)phenyl]carbonyl}piperazine hydrochloride (E1)

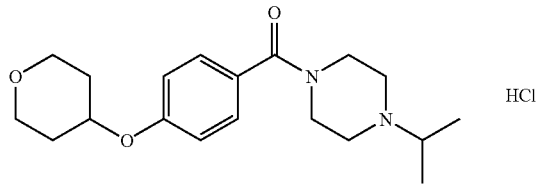

Method A

A solution of 4-(tetrahydro-2H-pyran-4-yloxy)benzoic acid (200 mg; prepared as described in Description 2 Method A) in dichloromethane (10 ml) at room temperature was treated with oxalyl chloride (0.16 ml, about 2 mole equivalents) and 1 drop of 10% N,N-dimethylformamide in dichloromethane. After 30 minutes, the solvent was evaporated off and the product was re-evaporated from dichloromethane (×2). The acid chloride product in dichloromethane was added to a stirred mixture of diethylaminomethylpolystyrene (844 mg, 3.2 mmol/g, 2.7 mmol, about 3 mole equivalents) and 1-isopropyl piperazine (115 mg, 0.90 mmol, e.g. available from Aldrich) in dichloromethane (10 ml) at room temperature. After 30 minutes, the mixture was loaded directly onto a silica flash column and eluted with a gradient of from 2% to 6% methanol (containing 10% 0.88 ammonia) in dichloromethane. The product-containing fractions were evaporated. The product was redissolved in dichloromethane and treated with excess 4M HCl in dioxane. The solvent was evaporated and the product was crystallised with acetone, filtered off, washed with acetone and dried to yield the title compound (247 mg).

1H NMR ($D_6$-DMSO, 250 MHz) δ10.9 to 11.0 (1H, br), 7.43 (2H, d, J=8.7 Hz), 7.04 (2H, d, J=8.7 Hz), 4.65 (1H, m), 4.18 (2H, br), 3.90-3.81 (2H, m), 3.57-3.41 (7H, m), 3.12-3.00 (2H, m), 2.02-1.95 (2H, m), 1.66-1.52 (2H, m), 1.28 (6H, d, J=6.6 Hz); MS (electrospray): m/z (M+H)$^+$333; $C_{19}H_{28}N_2O_3$ requires 332.

Method B

To a stirred solution of 4-(tetrahydro-2H-pyran-4-yloxy)benzoic acid (2.56 g, 11.5 mmol; which may be prepared as described in Description 2 Method B and/or Method C) in N,N-dimethylformamide (40 ml) at room temperature, was added 1-(3-dimethylaminopropyl)-3-ethylcarbodiimide hydrochloride (3.32 g, 17.3 mmol). The reaction mixture was stirred for 15 minutes, followed by the addition of 1-isopropyl piperazine (2.50 ml, 17.5 mmol). The resultant mixture was stirred for 20 hours. Dichloromethane (10 ml) was added to the reaction mixture and the solvent was removed in vacuo. The pale yellow oil residue was purified by silica gel chromatography, eluting with a gradient of from 0% to 10% of (2N ammonia/methanol) in dichloromethane, to yield the free base as a pale yellow oil (1.80 g) (LCMS (basic): m/z (M+H)$^+$ 333). The free base was dissolved in dichloromethane (20 ml), followed by the addition of 4.0 M HCl solution in dioxane (5 ml). The solvent was then removed in vacuo to yield the corresponding hydrochloride salt, 1-(1-methylethyl)-4-{[4-(tetrahydro-2H-pyran-4-yloxy)phenyl]carbonyl}piperazine hydrochloride, as an off-white solid (1.81 g); LCMS (basic): m/z (M+H)$^+$333.

Method C

To a stirred solution of 4-(tetrahydro-2H-pyran-4-yloxy)benzoic acid (0.205 g, 0.92 mmol; which may be prepared as described in Description 2 Method C) in N,N-dimethylformamide (3.5 ml) was added 1-(3-dimethylaminopropyl)-3-ethylcarbodiimide hydrochloride (0.268 g, 1.39 mmol). The reaction mixture was stirred for 15 minutes at room temperature, followed by the addition of 1-isopropyl piperazine (0.20 ml, 1.4 mmol). The resultant mixture was stirred for 66 hours at room temperature. Dichloromethane (5 ml) was added to the reaction mixture and the solvent was removed in vacuo. The pale yellow crude residue was purified by silica gel chromatography, eluting with a gradient of from 0% to 10% of (2M ammonia/methanol) in dichloromethane, to yield the free base as a pale yellow oil (204 mg) (LCMS (basic): m/z (M+H)$^+$333). The free base was dissolved in dichloromethane (5 ml), followed by the addition of 4.0 M HCl solution in dioxane (1 ml). The solvent was then removed in vacuo to yield the corresponding hydrochloride salt, 1-(1-methylethyl)-4-{[4-(tetrahydro-2H-pyran-4-yloxy)phenyl]carbonyl}piperazine hydrochloride, as an off-white solid (0.196 g); LCMS (basic): m/z (M+H)$^+$333.

Method D

To a stirred solution of 4-(tetrahydro-2H-pyran-4-yloxy)benzoic acid (36.5 g, 164 mmol, which may be prepared as described in Description 2 Method D), 1-(3-dimethylaminopropyl)-3-ethylcarbodiimide hydrochloride (38 g, 198 mmol), 1-hydroxybenzotriazole (31 g, 203 mmol) in N,N-dimethylformamide (500 ml) at room temperature, was added 1-isopropylpiperazine (26 ml, 182 mmol). The reaction mixture was stirred at room temperature for 1.5 hours and was then quenched by the addition of a saturated aqueous solution of sodium hydrogen carbonate (500 ml) and ethyl acetate (1 litre). The aqueous layer was extracted with ethyl acetate (400 ml) and the combined organic extracts were washed with water (2×400 ml). The solvent was removed in vacuo and the residue was taken up in dichloromethane (150 ml), followed by the addition of a 1.0 M HCl solution in diethyl ether (200 ml). The resultant white solid was then separated by filtration and was washed with dichloromethane to give the corresponding hydrochloride salt. Recrystallisation of this material from ethanol gave the title compound, 1-(1-methylethyl)-4-{[4-(tetrahydro-2H-pyran-4-yloxy)phenyl]carbonyl}piperazine hydrochloride, as a solid (32 g).

Example 2

Crystalline Form 1 of 1-(1-methylethyl)-4-{[4-(tetrahydro-2H-pyran-4-yloxy)phenyl]carbonyl}piperazine hydrochloride

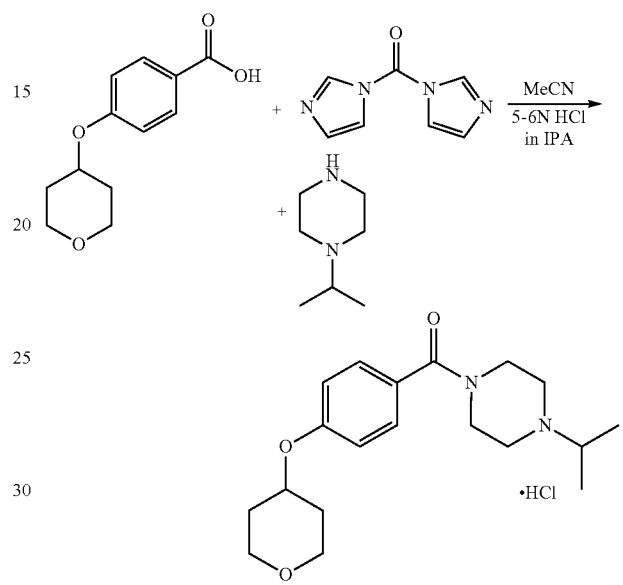

Short Summary Process Description

All weights, volumes ("vol") and equivalents are with respect to 4-(tetrahydro-2H-pyran-4-yloxy)benzoic acid.

4-(Tetrahydro-2H-pyran-4-yloxy)benzoic acid (1 wt, e.g. which may be as prepared in Description 3) and carbonyl diimidazole (CD) (0.8 wt, 1.1 mole equivalents) are charged to a 20 L vessel. Acetonitrile (12 volumes) is then added, and the suspension/slurry is warmed to 30° C. and stirred for about 2 to 2.25 hours. N-isopropylpiperazine (1-isopropylpiperazine, 0.66 wt, 1.15 mole equivalents) is added in one charge and the resulting hazy solution is heated to 50° C. over about 15-30 minutes and then stirred for about 2 to 2.25 hours. The reaction is monitored by HPLC. Following completion of the reaction, the mixture is cooled to 20° C. and any insoluble matter (e.g. any inorganics carried over in the 4-(tetrahydro-2H-pyran-4-yloxy)benzoic acid) is removed by filtration. The clarified solution is transferred to a 10 L vessel in portions and is concentrated by distillation under reduced pressure to approximately 3 volumes to remove acetonitrile (e.g. using 50° C. jacket temperature and 200 mbar pressure reducing to 100 mbar pressure). Following the distillation, propan-2-ol (6 volumes) is added and the solution is concentrated further by distillation under reduced pressure to 5 volumes. After further propan-2-ol (8 volumes) is added, the solution is heated to 70° C. with stirring and 5-6N HCl in isopropanol (0.9 volumes) is added over at least 10 minutes. Crystallisation generally commences during the addition. Following the addition the resulting slurry is ramp-cooled to 20° C. over 1.5 hours. The product is filtered and the cake is washed with isopropanol (3 volumes). The solvent is sucked free from the cake for at least 2 hours. The product is dried in a vacuum oven at 50° C. to constant probe temperature over at least 22 hours to give the title product.

Detailed Process Description
1. Added 4-(tetrahydro-2H-pyran-4-yloxy)benzoic acid (1 wt, 1000.0 g) to Vessel 1 (20 L).
2. Added carbonyl diimidazole (CD) (0.8 wt, 1.1 mole equivalents, 800.0 g) (obtained from Fluorochem) to Vessel 1.
3. Added acetonitrile (12 vol, 12 L) to Vessel 1 and started stirrer (gas evolution observed).
4. Heated contents of Vessel 1 cautiously to 30° C. and then stirred for 2 hours 10 minutes.
5. Added N-isopropylpiperazine (1-isopropylpiperazine) (obtained from Fluorochem) (0.66 wt, 1.15 mole equivalents, 666.4 g) to Vessel 1.
6. Heated contents of Vessel 1 cautiously to 50° C., over about 15-20 minutes, and then stirred for 2 hours 15 minutes.
7. Sampled the mixture for HPLC (quench onto butylamine and reaction deemed complete if ratio of product:butylamide is >50:1).
8. Cooled contents of Vessel 1 to 20° C.
9. Transferred the solution to Vessel 2 via a 5 micron Dominic filter to remove insoluble matter.
10. Rinsed Vessel 1 with acetonitrile (0.2 vol, 200 mL) and used as a line wash into Vessel 2.
11. Concentrated the contents of Vessel 2 to 3.0 volumes via distillation under reduced pressure. Started with 50° C. jacket temperature and 200 mbar vacuum, and reduce pressure gradually to 100 mbar.
12. Vessel 1 was rinsed with water and boiled out with methanol to clean.
13. Added propan-2-ol (6 volumes, 6 L) to Vessel 2.
14. Concentrated the contents of Vessel 2 to 5 volumes via distillation under reduced pressure.
15. Added propan-2-ol (8 volumes, 8 L) to Vessel 2.
16. Transferred reaction mixture to Vessel 1 for crystallisation.
17. Heat the contents of Vessel 1 to 70° C. with stirring.
18. Added 5-6N hydrochloric acid in propan-2-ol (0.9 volumes, 900 mL) to Vessel 1 via peristaltic pump fitted with silicone tubing over at least 10 mins.
19. Ramp-cooled the contents of Vessel 1 to 20° C. over 1.5 hours.
20. Filtered off product on a PTFE mini filter 9 fitted with Whatman No. 113 wet strengthened filter paper (rough side up).
21. Washed the filter cake with propan-2ol (3 volumes, 3 L) and sucked product free of solvent.
22. Dried the solid product in polythene lined steel trays covered with a muslin cloth, to a constant probe temperature, at 50° C. under vacuum for about 22 hours to give the title compound as a solid (1515.1 g).

From analysis, the crystalline Form 1 of 1-(1-methylethyl)-4-{[4-(tetrahydro-2H-pyran-4-yloxy)phenyl]carbonyl}piperazine hydrochloride produced by Example 2 is believed not to be an entirely pure crystal form, and is believed to contain very approximately 20% of crystalline Form 2. Analyses of the crystalline Form 1 product produced by Example 2 include the following:

X-Ray Powder Diffraction (XRPD)

XRPD data were acquired on a PANalytical X'Pert Pro powder diffractometer, equipped with an X'Celerator detector. The acquisition conditions were: radiation: Cu Kα (copper K-alpha), generator tension: 40 kV, generator current: 45 mA, start angle: 2.0° 2θ (two-theta), end angle: 40.0° 2θ, step size: 0.0167° 2θ (two-theta). The time per step was 31.750 s. The sample was prepared by mounting a few milligrams of sample on a Si wafer (zero background) plates, resulting in a thin layer of powder.

Some characteristic peak positions and calculated d-spacings for the crystalline Form 1 product produced by Example 2 are summarised in the following table (note: these are not the only peaks seen). These were calculated from the raw data using Highscore software.

| XRPD - Crystalline Form 1 | |
|---|---|
| 2θ/° | d-spacing/Å (Ångstroms) |
| 6.4 | 13.9 |
| 12.7 | 7.0 |
| 15.4 | 5.7 |
| 15.7 | 5.6 |
| 17.1 | 5.2 |
| 19.1 | 4.7 |
| 19.7 | 4.5 |
| 21.9 | 4.1 |
| 25.5 | 3.5 |
| 27.0 | 3.3 |
| 28.2 | 3.2 |

Figure 3:
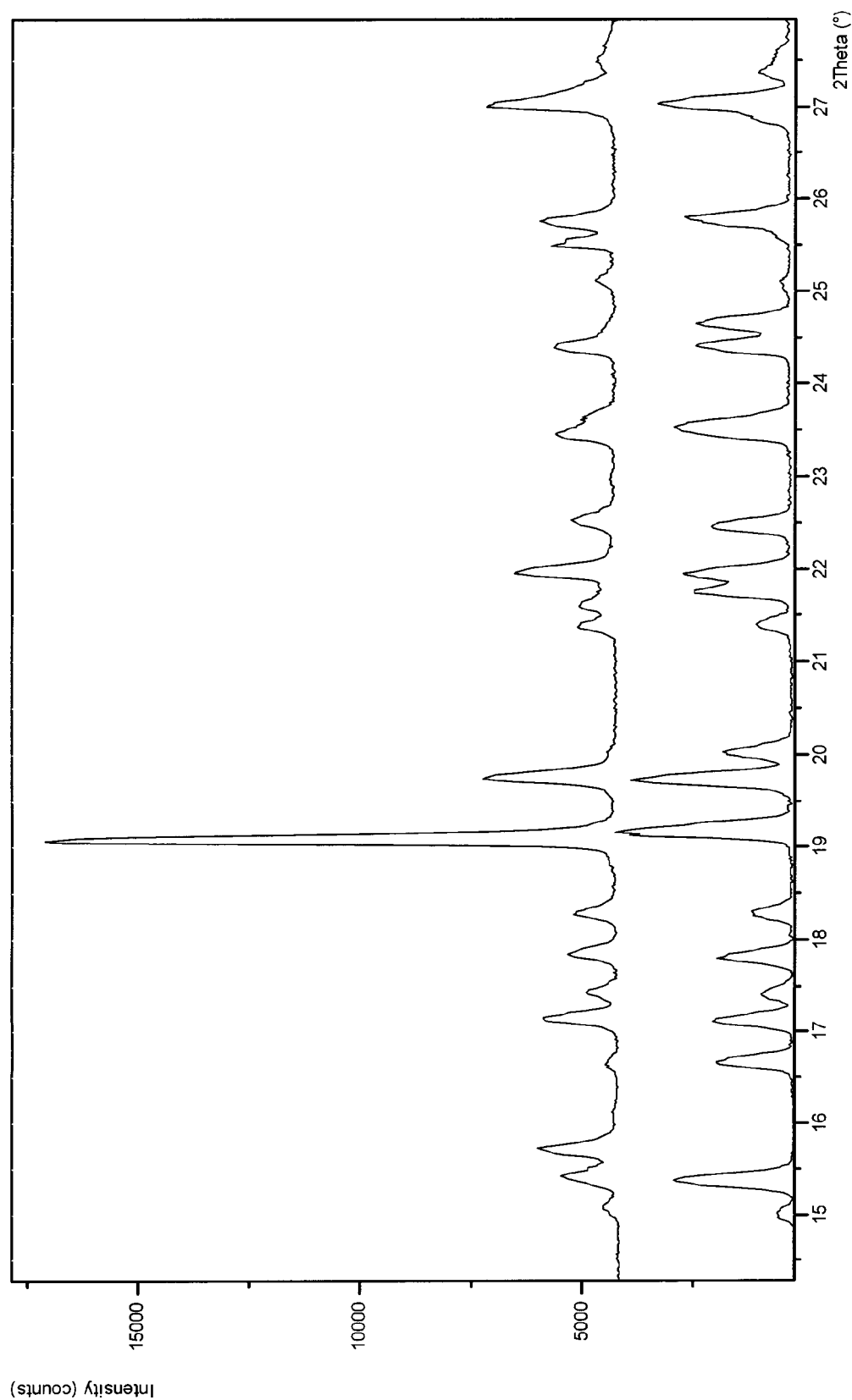
FIG. 3 is an overlay of a portion of the XRPD spectra for crystalline Form 1 (top) and crystalline Form 2 (bottom) of 1-(1-methylethyl)-4-{[4-(tetrahydro-2H-pyran-4-yloxy) phenyl]carbonyl}piperazine hydrochloride.

The XRPD spectrum for crystalline Form 1 as prepared by Example 2 is shown in FIG. 1. An XRPD overlay spectrum is shown in FIG. 3, comparing the XRPD peaks of crystalline Form 1 from Example 2 (top) to those of crystalline Form 2 from Example 3 (bottom), for comparison purposes. The crystalline Form 1 XRPD peaks at 15.7° 2θ and 25.5° 2θ appear to be characteristic for crystalline Form 1 in that these peaks do not appear to be present in the XRPD spectrum of crystalline Form 2.

FT-IR (FT-Infrared) Spectrum

FT-IR spectrum was acquired over 64 scans at 4 cm$^{-1}$ resolution using a Nicolet Avatar 360 FT-IR spectrometer, fitted with a Diamond/ZnSe ATR Accessory.

Figure 4:
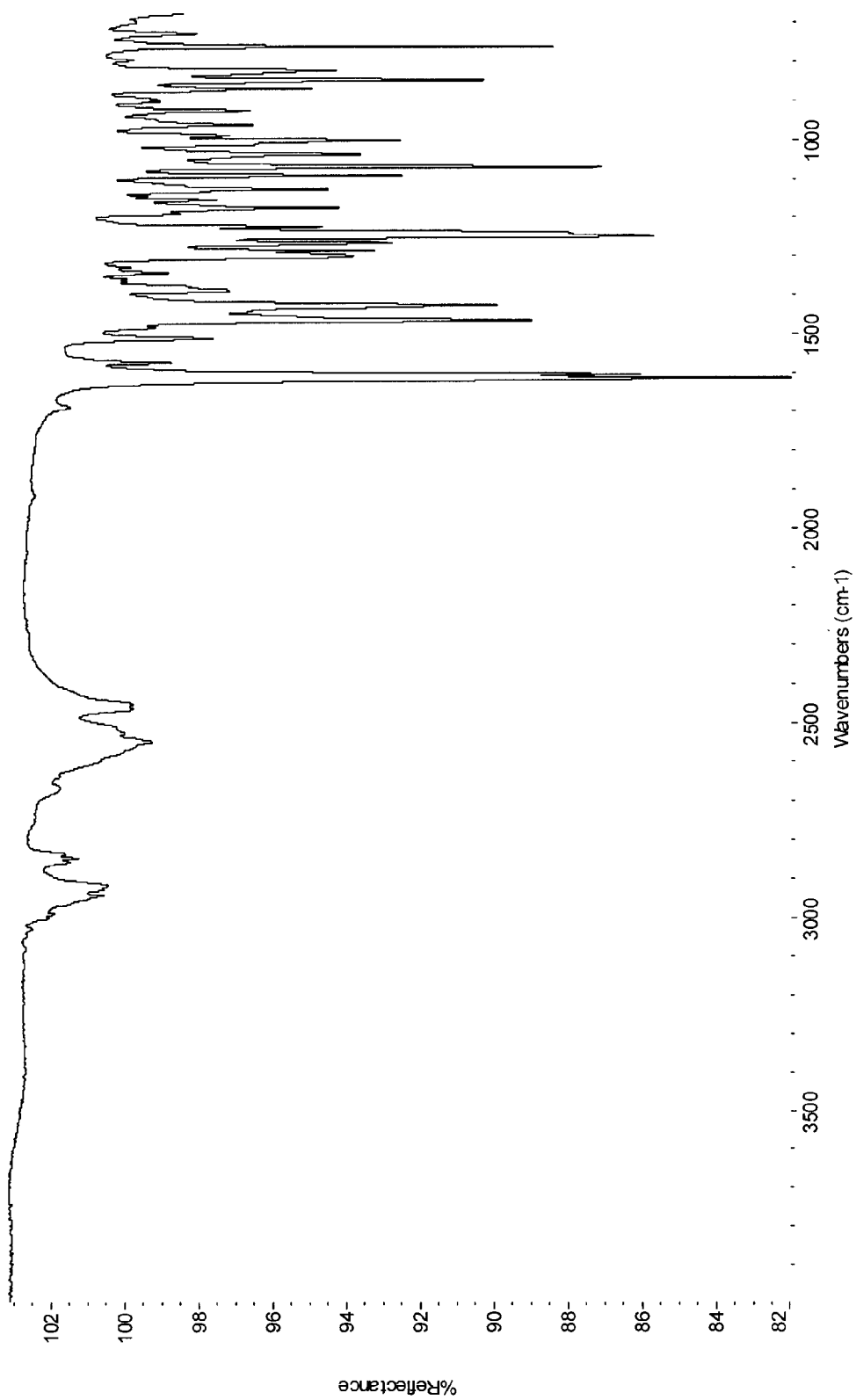
FIG. 4 is a Fourier-Transform Infrared (FT-IR) spectrum for crystalline Form 1 of 1-(1-methylethyl)-4-{[4-(tetrahydro-2H-pyran-4-yloxy)phenyl]carbonyl}piperazine hydrochloride, showing the spectral region from 4000 to 675 cm$^{-1}$.
Figure 8:
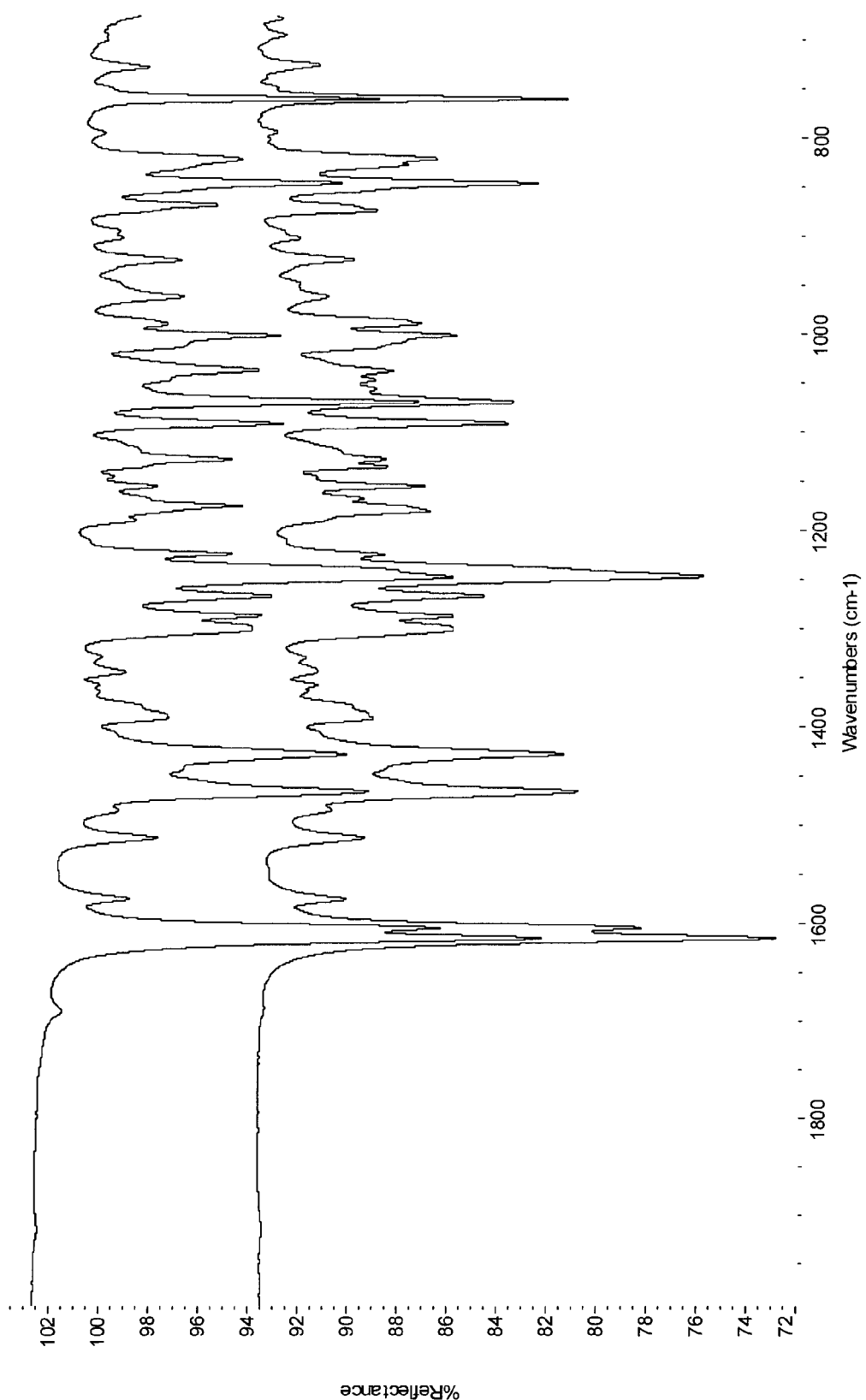
FIG. 8 is an overlay of the FT-IR spectra for crystalline Form 1 (top) and crystalline Form 2 (bottom) of 1-(1-methylethyl)-4-{[4-(tetrahydro-2H-pyran-4-yloxy)phenyl]carbonyl}piperazine hydrochloride, showing the spectral region from 2000 to 675 cm$^{-1}$.

The FT-IR spectrum for crystalline Form 1 as prepared by Example 2 is shown in FIGS. 4 and 5, showing the spectral regions from 4000 to 675 cm$^{-1}$ and from 2000 to 675 cm$^{-1}$ respectively. An FT-IR overlay spectrum, for comparison purposes, comparing these peaks of crystalline Form 1 from Example 2 to those of crystalline Form 2 from Example 3, is shown in FIG. 8, showing the spectral regions from 2000 to 675 cm$^{-1}$.

Solid-State NMR Spectrum

A solid-state NMR spectrum was obtained at a frequency of 90.55 MHz for $^{13}$C observation using a 4-mm Bruker HFX MAS (magic-angle spinning) probe at a temperature of 296K, and a spinning speed of 8 kHz. Data were acquired using a cross polarisation sequence with side-band suppression. Several scans were acquired, with a relaxation delay of 10 seconds.

Chemical shifts for the resonances observed for crystalline Form 1 as prepared by Example 2 are listed below (in ppm): 18.5±0.3, 30.4±0.3, 31.8±0.3, 37.6±0.3, 45.8±0.3, 49.4±0.3, 52.3±0.3, 59.2±0.3, 63.6±0.3, 68.4±0.3, 110.3±0.3, 118.8±0.3, 128.4±0.3, 131.2±0.3, 133.9±0.3, 159.1±0.3, and 167.6 ppm.

Additional resonances were also observed at 19.5±0.3, 71.1±0.3, 109.5±0.3 and 119.6±0.3 ppm, and are thought to correspond to crystalline Form 2 as an impurity.

Figure 9:
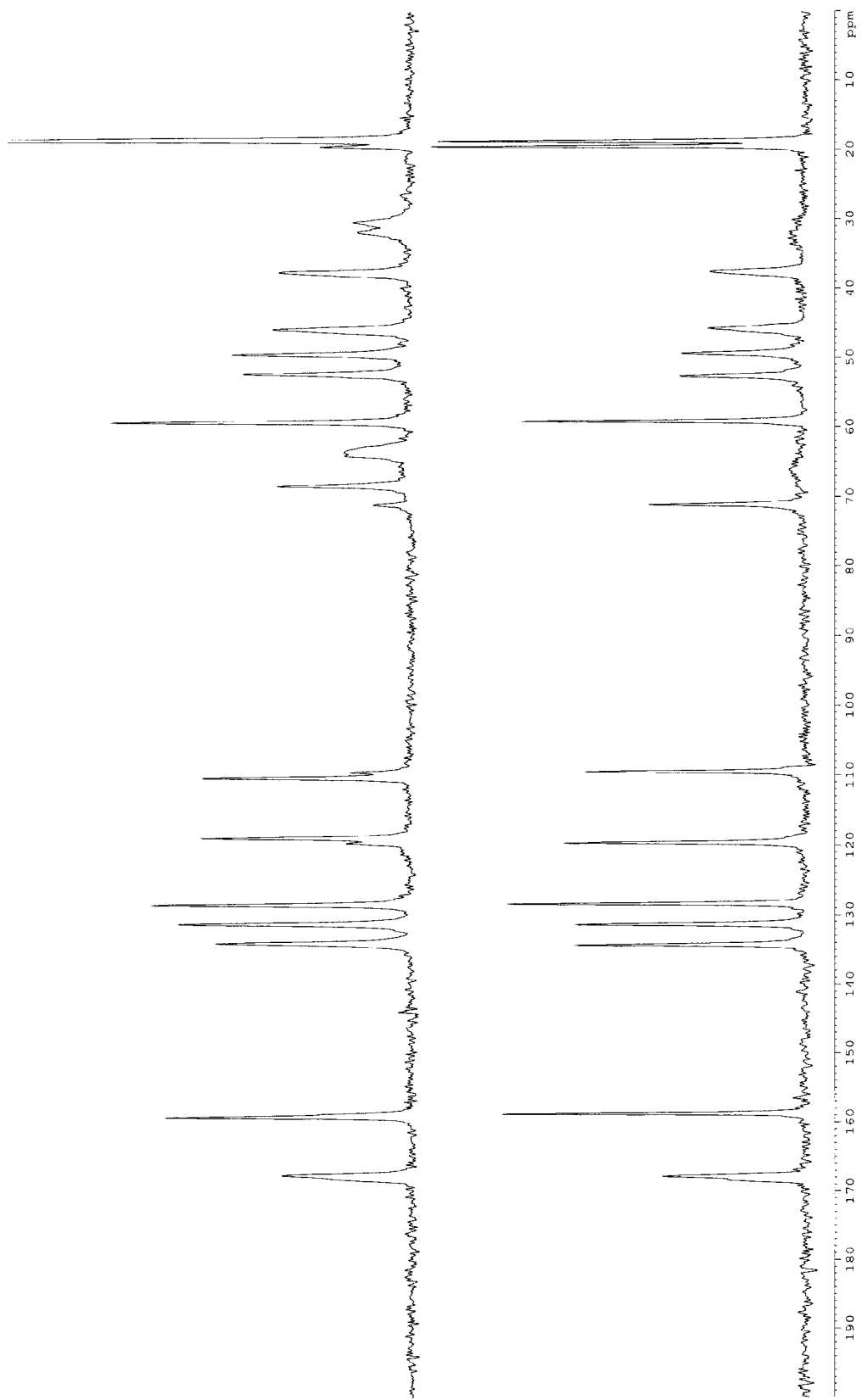
FIG. 9. is an overlay of the $^{13}$C solid-state nuclear magnetic resonance (solid-state NMR) spectra, in ppm, of crystalline Form 1 (top) and crystalline Form 2 (bottom) of 1-(1-methylethyl)-4-{[4-(tetrahydro-2H-pyran-4-yloxy)phenyl]carbonyl}piperazine hydrochloride.

The solid-state NMR spectrum for crystalline Form 1 as prepared by Example 2, as a comparison overlay with that of crystalline Form 2, is illustrated in FIG. 9.

Example 3

Crystalline Form 2 of 1-(1-methylethyl)-4-{[4-(tetrahydro-2H-pyran-4-yloxy)phenyl]carbonyl}piperazine hydrochloride

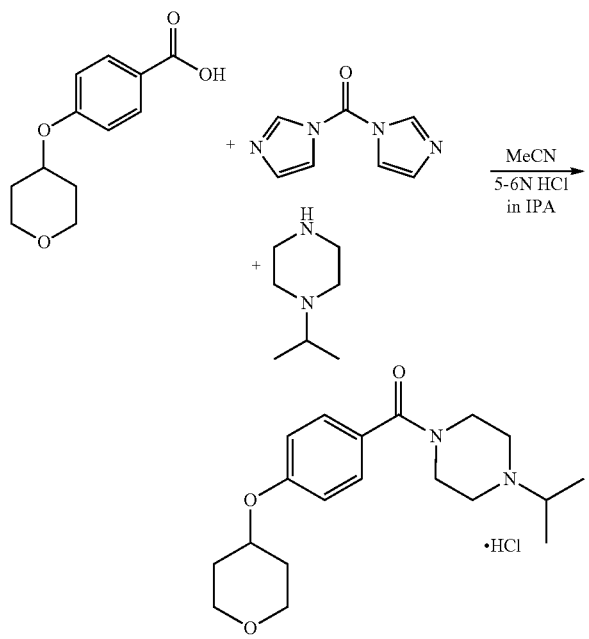

4-(Tetrahydro-2H-pyran-4-yloxy)benzoic acid (1 wt, 20 g; e.g. may be prepared as described in Description 3) was suspended in acetonitrile (80 mL). A solution of carbonyl diimidazole (CD) (0.8 wt, 16 g, 1.1 mole equivalents) in acetonitrile (80 mL), which had been pre-warmed to 35-40° C., was added in a single charge to the suspension at ambient temperature. Acetonitrile line wash (20 mL, 1 volume) was also added. The reaction mixture was heated under nitrogen at 60° C. for 1 hour. N-isopropylpiperazine (1-isopropylpiperazine, 0.66 wt, 13.33 g, obtained from Fluorochem ACl) was added to the reaction mixture, and heating was continued for 2 hours. The mixture was concentrated to approx 2.5 volumes (50 mL) via vacuum distillation to give a thick mobile oil. Propan-2-ol (240 mL, 12 volumes) was then added, and the mixture was concentrated by distillation under reduced pressure (100 mbar) to remove 2 volumes (40 mL). The mixture was heated to 70° C. with stirring. 5-6N hydrochloric acid in Propan-2-ol (20 mL, 1 volume) was added to the mixture over 10 min. No crystallisation occurred until all of the acid had been added. The reaction mixture was maintained at 70° C. overnight. The mixture was cooled and the slurry was filtered. The filtered solid was dried under air suction on the filter over 1 to 1.5 hours. The title product was obtained as a slightly pink solid (25 g).

Analyses of the crystalline Form 2 product produced by Example 3 include the following:

X-Ray Powder Diffraction (XRPD)

XRPD data were acquired on a PANalytical X'Pert Pro powder diffractometer, equipped with an X'Celerator detector. The acquisition conditions were: radiation: Cu Kα (copper K-alpha), generator tension: 40 kV, generator current: 45 mA, start angle: 2.0° 2θ (two-theta), end angle: 40.0° 2θ, step size: 0.0167° 2θ (two-theta). The time per step was 31.750 s. The sample was prepared by mounting a few milligrams of sample on a Si wafer (zero background) plates, resulting in a thin layer of powder.

Some characteristic peak positions and calculated d-spacings for the crystalline Form 2 product produced by Example 3 are summarised in the following table (note: these are not the only peaks seen). These were calculated from the raw data using Highscore software.

| XRPD - Crystalline Form 2 | |
|---|---|
| 2θ/° | d-spacing/Å (Ångstroms) |
| 6.4 | 13.8 |
| 12.8 | 6.9 |
| 15.4 | 5.8 |
| 19.2 | 4.6 |
| 19.7 | 4.5 |
| 20.0 | 4.4 |
| 21.8 | 4.1 |
| 21.9 | 4.1 |
| 23.5 | 3.8 |
| 24.65 (rounds to 24.7) | 3.6 |
| 25.8 | 3.5 |
| 27.0 | 3.3 |

The XRPD spectrum for crystalline Form 2 as prepared by Example 3 is shown in FIG. 2. An XRPD overlay spectrum is shown in FIG. 3, comparing the XRPD peaks of crystalline Form 2 from Example 3 (bottom) to those of crystalline Form 1 from Example 2 (top), for comparison purposes. The crystalline Form 2 XRPD peaks at 20.0° 2θ and 24.65° (or 24.7°) 2θ appear to be characteristic for crystalline Form 2 in that these peaks do not appear to be significantly present in the XRPD spectrum of crystalline Form 1.

FT-IR (FT-infrared) Spectrum

FT-IR spectrum was acquired over 64 scans at 4 cm$^{-1}$ resolution using a Nicolet Avatar 360 FT-IR spectrometer, fitted with a Diamond/ZnSe ATR Accessory.

Figure 6:
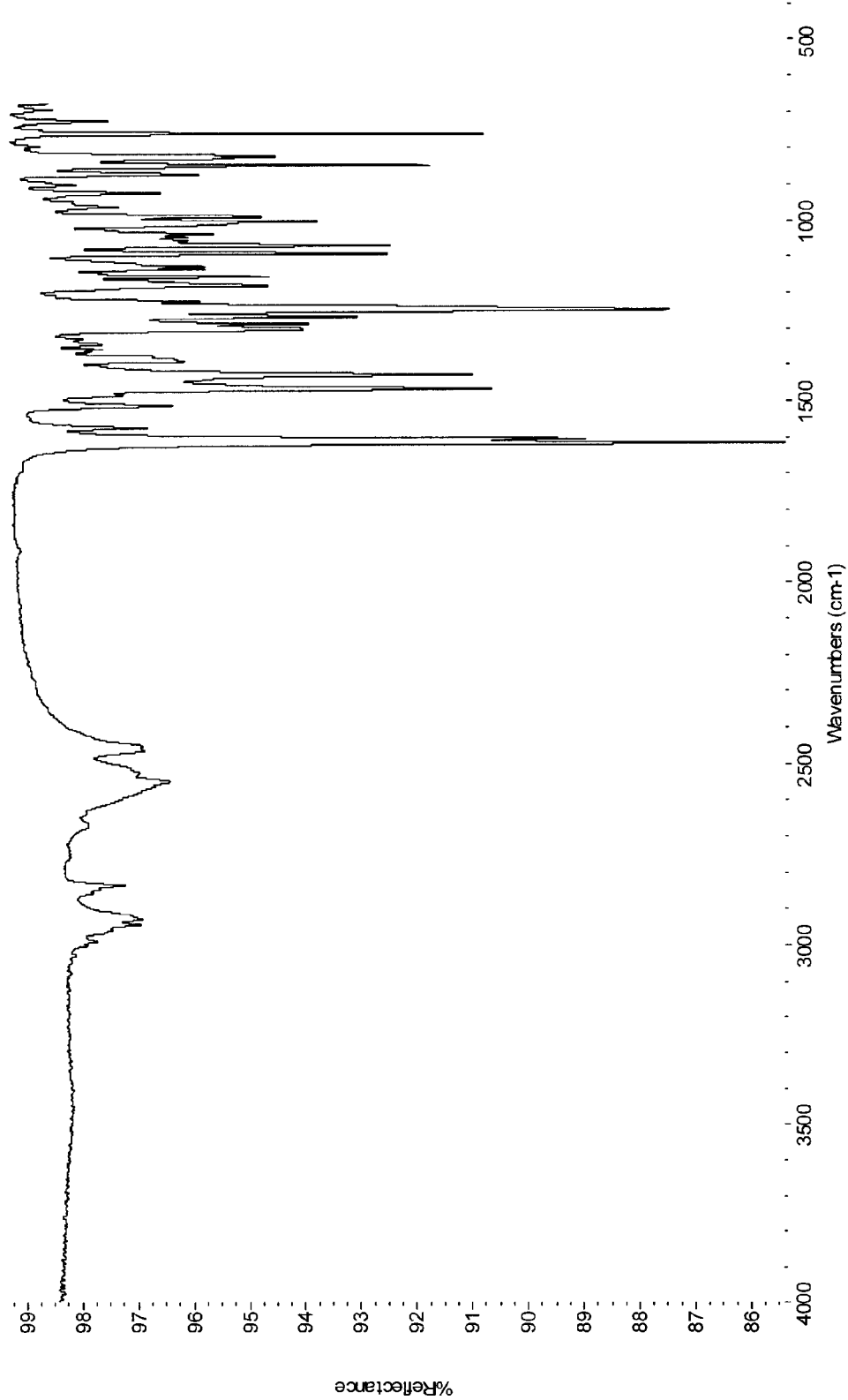
FIG. 6 is a Fourier-Transform Infrared (FT-IR) spectrum for crystalline Form 2 of 1-(1-methylethyl)-4-{[4-(tetrahydro-2H-pyran-4-yloxy)phenyl]carbonyl}piperazine hydrochloride, showing the spectral region from 4000 to 675 cm$^{-1}$.

The FT-IR spectrum for crystalline Form 2 as prepared by Example 3 is shown in FIGS. 6 and 7, showing the spectral regions from 4000 to 675 cm$^{-1}$ and from 2000 to 675 cm$^{-1}$ respectively. An FT-IR overlay spectrum comparing these Form 2 peaks from Example 3 to those of crystalline Form 1 from Example 2 is shown in FIG. 8, for comparison purposes, showing the spectral regions from 2000 to 675 cm$^{-1}$.

Solid-State NMR Spectrum

A solid-state NMR spectrum was obtained at a frequency of 90.55 MHz for $^{13}$C observation using a 4-mm Bruker HFX MAS (magic-angle spinning) probe at a temperature of 296K, and a spinning speed of 8 kHz. Data were acquired using a cross polarisation sequence with side-band suppression. Several scans were acquired, with a relaxation delay of 10 seconds.

Chemical shifts for the resonances observed for crystalline Form 2 as prepared by Example 3 are listed below (in ppm): 18.8±0.3, 19.5±0.3, 32.4±0.3, 37.5±0.3, 45.7±0.3, 49.3±0.3, 52.7±0.3, 59.1±0.3, 66.3±0.3, 71.1±0.3, 109.4±0.3, 119.6±0.3, 128.4±0.3, 131.3±0.3, 134.3±0.3, 158.7±0.3, and 167.8±0.3 ppm.

The solid-state NMR spectrum for crystalline Form 2 as prepared by Example 3, as a comparison overlay with that of crystalline Form 1 from Example 2, is illustrated in FIG. 9.

Example 4

1-(1-Methylethyl)-4-{[4-(tetrahydro-2H-pyran-4-yloxy)phenyl]carbonyl}piperazine hydrochloride

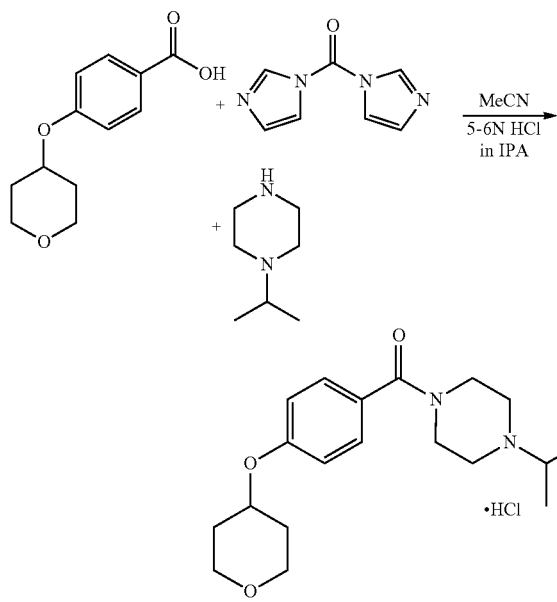

All weights, volumes and equivalents are with respect to 4-(tetrahydro-2H-pyran-4-yloxy)benzoic acid.

4-(Tetrahydro-2H-pyran-4-yloxy)benzoic acid (10 g, 1 wt, 1 vol, 1 mole equivalent) is added portion-wise (take care, gas evolution) over 10 minutes to a stirred solution of carbonyl diimidazole (CDI, 8.0 g, 0.8 wt, 1.1 mole equivalents) in acetonitrile (100 mL, 10 vol) under nitrogen at about 65° C. (jacket temperature at 70° C.). Acetonitrile (1.5 volumes, 15 mL) is used as line wash for the container of the 4-(tetrahydro-2H-pyran-4-yloxy)benzoic acid, and the funnel is used for the addition of the reagent. The resulting suspension/slurry is stirred at about 65° C. for at least ca. 2 hours (e.g. ca. 2-2.5 hours) before being sampled.

Reaction progress is monitored by HPLC: the sample is prepared by quenching a drop of the reaction mixture into 1 mL of 5% butylamine solution in acetonitrile; this allows determination of residual 4-(tetrahydro-2H-pyran-4-yloxy) benzoic acid by derivatisation of the activated acid-imidazolide to the corresponding butylamide. This is generally recorded for information only since slurry inhomogeneity can give rise to inconsistent results (typically<2% residual 4-(tetrahydro-2H-pyran-4-yloxy)benzoic acid is satisfactory at this stage).

Subsequently 1-isopropylpiperazine (0.667 wt, 6.67 g, 1.15 mole equivalents) is added in one portion at about 65° C., followed by a line wash with acetonitrile (0.5 vol, 5 mL). The resulting hazy solution is kept stirred at about 65° C. for at least ca. 2 hours (e.g. ca. 2-2.5 hours) before being sampled. Reaction progress is monitored by HPLC, using the method stated above.

The reaction is then allowed to cool and insoluble matter is removed by filtration. The clarified solution is then concentrated by vacuum distillation to 2.5 to 3 volumes and 5% water in isopropanol (5 volumes, 50 mL) is added at ambient temperature. The solution is then heated to about 65° C. and 5-6N HCl in isopropanol (0.9 volumes) is added in one charge. Crystallisation can commence shortly after the addition. The resulting slurry is aged at 65° C. for 1.5 hours. The slurry is then cooled to 55° C. over ca. 20 min and kept at 55° C. for 1.5 hours, is then cooled to 45° C. over ca. 20 min and kept at 45° C. for 1.5 hours, and is then allowed to cool to ambient temperature and the solid is filtered off (1 hour in total); the total cooling time is therefore about 4.5 to 4.75 hours.

The solid 1-(1-Methylethyl)-4-{[4-(tetrahydro-2H-pyran-4-yloxy)phenyl]carbonyl}piperazine hydrochloride, isolated by filtration, is washed with 4 volumes of isopropanol and is dried under vacuum at 50° C., for example overnight.

The above-described process is currently believed to produce crystalline Form 2 of 1-(1-methylethyl)-4-{[4-(tetrahydro-2H-pyran-4-yloxy)phenyl]carbonyl}piperazine hydrochloride.

Example 5

Recrystallisation of 1-(1-methylethyl)-4-{[4-(tetrahydro-2H-pyran-4-yloxy)phenyl]carbonyl}piperazine hydrochloride

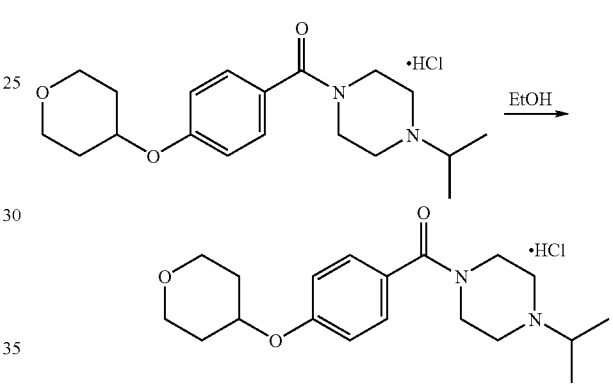

Short Process Description

All weights, volumes ("vol") and equivalents are relative to 1-(1-methylethyl)-4-{[4-(tetrahydro-2H-pyran-4-yloxy)phenyl]carbonyl}piperazine hydrochloride.

A suspension of 1-(1-methylethyl)-4-{[4-(tetrahydro-2H-pyran-4-yloxy)phenyl]carbonyl}piperazine hydrochloride (1 wt, e.g. may be prepared as described in Example 1 Method D) in ethanol (50 vol) is heated to reflux and stirred until a solution has formed. This solution is cooled to 65±3° C. and clarified. A line wash of hot ethanol (3 vol) is added the solution is cooled to 58±3° C. A seed of 1-(1-methylethyl)-4-{[4-(tetrahydro-2H-pyran-4-yloxy)phenyl]carbonyl}piperazine hydrochloride (0.01 wt) is added and the resulting suspension is stirred at 58±3° C. for 30 min. The suspension is then cooled to 0±3° C. over 2 hours before being aged at this temperature for 1 hour. The solid is then filtered off under vacuum and washed with cold ethanol (3 vol). The product is the dried in vacuo at 40° C. until constant probe temperature.

Detailed Process Description

1. Add 1-(1-methylethyl)-4-{[4-(tetrahydro-2H-pyran-4-yloxy)phenyl]carbonyl}piperazine hydrochloride (1 wt, 140 g, e.g. may be prepared as described in Example 1 Method D) to Reactor 1.
2. Purge reactor with Nitrogen.
3. Add ethanol (50 vol, 7100 mL).
4. Heat to reflux and stir until a solution formed.
5. This solution is cooled to 65±3° C.
6. Contents of Reactor 1 are transferred to Reactor 2 via a peristaltic pump fitted with silicone tubing and a 5 micron in-line filter.

7. Add ethanol to Reactor 1 (3 vol, 420 mL) and heat to 65±3° C.
8. Contents of Reactor 1 are transferred to Reactor 2 as per step 6.
9. The solution is cooled to 58±3° C.
10. A seed of 1-(1-methylethyl)-4-{[4-(tetrahydro-2H-pyran-4-yloxy)phenyl]carbonyl}piperazine hydrochloride (0.01 wt) is added and the resulting suspension is stirred at 58±3° C. for 30 min.
11. The suspension is then cooled to 0±3° C. over 2 hours before being aged at this temperature for 1 hour.
12. The solid is then filtered off under vacuum and washed with cold ethanol (3 vol).
13. The product is the dried in vacuo at 40° C. until constant probe temperature.
14. The product is generally obtained as a white solid.

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pcDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 µg ml$^{-1}$. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 µg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 µg ml$^{-1}$ Zeocin™

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 µm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 µg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of homogenisation buffer (50 mM N-2-hydroxyethylpiperazine-N'-2-ethanesulfonic acid (HEPES), 1 mM ethylenediamine tetra-acetic acid (EDTA), pH 7.4 with KOH containing 10e-4M leupeptin (acetyl-leucyl-leucyl-arginal; Sigma L2884) and 25 g/ml bacitracin (Sigma B0125)) supplemented with 1 mM phenylmethylsulfonyl fluoride (PMSF) and 2×10e-6M pepstain A (Sigma). The cells are then homogenised by 2×15 second bursts in a 1 litre glass Waring blender, followed by centrifugation at 500 g for 20 minutes. The supernatant is then spun at 48,000 g for 30 minutes. The pellet is resuspended in homogenisation buffer (4× the volume of the original cell pellet) by vortexing for 5 seconds, and then being forced by syringe through a 0.6 mm internal diameter needle. At this point the preparation is aliquoted into polypropylene tubes and stored at −80° C.

(iii) Generation of Histamine H1 Cell Line

The human H1 receptor was cloned generally using known procedures described in the literature [Biochem. Biophys. Res. Commun. 1994, 201(2), 894]. Chinese hamster ovary cells stably expressing the human H1 receptor were generated generally according to known procedures described in the literature [Br. J. Pharmacol. 1996, 117(6), 1071].

The compound of the invention or a pharmaceutically acceptable salt thereof may be tested for in vitro biological activity in accordance with the following assays:

(I) Histamine H3 Functional Antagonist Assay

For each compound being assayed, in a solid white 384 well plate, is added:—

(a) 0.5 µl (0.5 ul) of test compound diluted to the required concentration in DMSO (or 0.5 µl (0.5 ul) DMSO as a control);
(b) 30 µl (30 ul) bead/membrane/GDP mix prepared by mixing Wheat Germ Agglutinin Polystyrene LeadSeeker® (WGA PS LS) scintillation proximity assay (SPA) beads with membrane (prepared for example in accordance with the methodology described above) and 10 µM (10 uM) final concentration of guanosine 5' diphosphate (GDP), and diluting in assay buffer (20 mM N-2-Hydroxyethylpiperazine-N'-2-ethanesulfonic acid (HEPES)+100 mM NaCl+10 mM MgCl$_2$, pH7.4 NaOH) to give a final volume of 30 µl (30 ul) which contains 5 µg (5 ug) protein and 0.25 mg bead per well, and incubating at room temperature for 60 minutes on a roller;
(c) 15 µl (15 ul) of 0.38 nM [$^{35}$S]-GTPγS ([$^{35}$S]-GTP-gamma-S) (Amersham; Radioactivity concentration=37 MBq/ml; Specific activity=1160 Ci/mmol), histamine (at a concentration that results in the final assay concentration of histamine being EC$_{80}$) The plate is sealed and after 2-6 hours, the plate is centrifuged for 5 min at 1500 rpm and counted on a Viewlux counter using a 613/55 filter for 5 min/plate. Data is analysed using a 4-parameter logistical equation. Basal activity used as minimum, i.e. wherein the histamine H3 antagonist iodophenpropit (30 uM, 0.5 ul) has been added to the well.

(II) Histamine H1 Functional Antagonist Assay

Adherent Chinese Hamster Ovary (CHO) cells stably expressing the recombinant human H$_1$ receptor were maintained in culture at 37° C. under 5% CO$_2$ in Alpha Minimum Essential Medium without ribonucleosides (Gibco Invitrogen) supplemented with 10% dialysed foetal calf serum and 200 mM Glutamine. These cells, expressing the human H1 receptor, were snap frozen and stored ready for assay.

24 or 72 hours prior to assay the cells were seeded into black walled clear-base 384-well plates at a density of 12,000 or 4 000 cells per well (respectively) and cultured at 37° C. under 5% $CO_2$. Cell seeding densities result in a confluent monolayer of cells at a time point of approximately 24 hours for 12 00 cells or 72 hours for 4 000 cells. Media was aspirated off and the cells were then incubated with HBSS medium ($CaCl_2.2H_2O$ 1.26 mM, Glucose 5.55 mM, KCl 5.36 mM, $MgSO_4$ (anhyd.) 0.81 mM, NaCl 136.89 mM, $KH_2PO_4$ (anhyd.) 0.41 mM, HEPES 20 mM, $NaHCO_3$ 4.16 mM) containing the cytoplasmic calcium indicator, Fluo-4 in the acetyl-methyl form (4 mM), 2.5 mM Probenecid and 250 uM Brilliant Black (Molecular Devices) at 37° C. for 60 min. The loaded cells were then incubated with test compound for 30 min at 37° C. The plates were then placed into a FLIPR (Molecular Devices, UK) for testing in antagonist mode, where a pre-determined concentration of Histamine (approximately 4×EC50) was added while cell fluorescence ($\lambda$ex 488 nm, $\lambda$em 540 nm) was monitored.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

Results of H3 and H1 Functional Antagonist Assays 1-(1-Methylethyl)-4-{[4-(tetrahydro-2H-pyran-4-yloxy)phenyl]carbonyl}piperazine hydrochloride (e.g. Example E1) was tested in the histamine H3 functional antagonism assay. The result is expressed as a functional $pK_i$ ($fpK_i$) value. A functional $pK_i$ is the negative logarithm of the antagonist equilibrium dissociation constant as determined in the H3 functional antagonist assay using membrane prepared from cultured H3 cells. The result given is an average of a number of experiments. 1-(1-Methylethyl)-4-{[4-(tetrahydro-2H-pyran-4-yloxy)phenyl]carbonyl}piperazine hydrochloride (e.g. Example E1) exhibited antagonism with a $fpK_i$ of approximately 7.6 (as the mean of 27 experiments), with a range of $fpK_i$ observed of from 6.9 to 8.2.

1-(1-Methylethyl)-4-{[4-(tetrahydro-2H-pyran-4-yloxy)phenyl]carbonyl}piperazine hydrochloride (e.g. Example E1) was tested in the histamine H1 functional antagonist assay or a similar H1 functional antagonist assay. Again, the result is expressed as a functional $pK_i$ ($fpK_i$) value and is an average of a number of experiments. 1-(1-Methylethyl)-4-{[4-(tetrahydro-2H-pyran-4-yloxy)phenyl]carbonyl}piperazine hydrochloride (e.g. Example E1) exhibited antagonism approximately <5.6 $fpK_i$.

Rat Ex Vivo Binding Studies—Rat Brain Histamine H3 Receptor Occupancy

Ex vivo binding studies were carried out to determine brain histamine H3 receptor occupancy in rats at certain time points after oral administration of a test compound.

Adult male rats (Lister hooded 200-250 g, Charles River, UK) received vehicle (1% w/v aqueous methylcellulose) (control) or the test compound (10 mg/kg) by oral gavage (n=3 per group) and were sacrificed 1 or 4 hours following oral dosing. The 1 hour and 4 hour studies were not necessarily done on the same day. Terminal blood samples were collected and brains rapidly removed. Cerebral cortex tissue was dissected from half of each brain for ex vivo binding; the other half brain can be used for pharmacokinetic analysis of brain concentrations of each compound. All dissected tissue samples were snap-frozen in liquid nitrogen, and stored at −80° C. until use. The tissues were rapidly thawed and homogenised in approximately 30 volumes of ice cold assay reaction buffer. The assay reaction buffer contained 50 mM Tris-HCl (made up using Trizma pre-set crystals pH 7.7@25° C., Sigma cat. No. T8068-250G) and 5 mM EDTA, with a final buffer pH of 7.2 to 7.8, usually about 7.4. The crude homogenate (600-800 μg/well) was then used to measure H3 receptor binding using [$^3$H]-R-α-methylhistamine as radioligand. Assays measuring total binding of [$^3$H]-R-α-methylhistamine consisted of 50 μl assay reaction buffer, 400 μl of homogenate (corresponding to 600-800 μg/well) and 50 μl of 2 nM R(−)α-Methyl[imidazole-2,5(n)-$^3$H]histamine dihydrochloride ([$^3$H]-R-α-methylhistamine; specific activity, 24 Ci mmol$^{-1}$, Amersham Biosciences, catalogue no. TRK1017). Incubations with [$^3$H]-R-α-methylhistamine were for 45 min at 30° C. Non-specific binding of [$^3$H]-R-α-methylhistamine was determined in parallel using the same assay except that 50 μl of 10 μM imetit (an H3 receptor agonist, e.g. available from Tocris) was used instead of the 50 μl of assay reaction buffer. The experiments were terminated by rapid filtration through Whatman GF/B filters (pre-soaked in 0.3% v/v polyethyleneimine (PEI)), and then the filters were washed through with 4×5 ml of ice cold harvesting buffer. The harvesting buffer contained 50 mM Tris-HCl (from Trizma pre-set crystals pH 7.7@25° C.) and 5 mM $MgCl_2$, with a final buffer pH of 7.2 to 7.8, usually about 7.4. Filters were dried and added to vials each containing 4 ml Ultima Gold MV scintillation fluid (Hewlett Packard) and radioactivity determined by liquid scintillation spectrometry using a Packard Tri-Carb 2500TR liquid scintillation counter.

Specific binding of [$^3$H]-R-α-methylhistamine to the H3 receptor was determined by the subtraction of the value obtained for non-specific binding from the value obtained for total binding.

Protein concentrations were determined using the Bradford assay method (Bio-Rad Protein Assay Dye Reagent Concentrate, catalogue no. 500-0006; from Bio-Rad Laboratories GmbH, Heidemannstrasse 164, 80939 Muenchen, Germany; or from Bio-Rad, York, UK) with bovine serum albumin as a standard. Specific radioactivity in the samples was corrected for protein (i.e. per microgram of protein).

The specific binding of [$^3$H]-R-α-methylhistamine to the H3 receptor is expressed as a mean (n=3 rats)±SEM (standard error of the mean), as a percentage of vehicle-treated control animals. Data is also expressed as inhibition of [$^3$H]-R-α-methylhistamine specific binding to the H3 receptor, as a surrogate measure for H3 receptor occupancy by the test compound, calculated as 100% minus the % mean specific binding of [$^3$H]-R-α-methylhistamine to the H3 receptor.

Results of Rat Ex Vivo Binding Studies

For 1-(1-methylethyl)-4-{[4-(tetrahydro-2H-pyran-4-yloxy)phenyl]carbonyl}piperazine hydrochloride

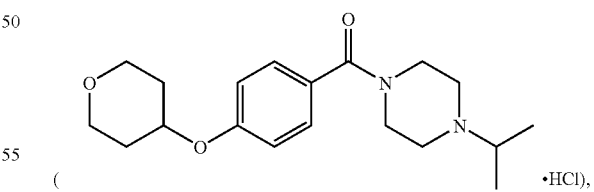

within the present invention, dosed orally to rats (n=3) at 10 mg/kg, and with the rats sacrificed 1 hour following oral dosing, the specific binding of [$^3$H]-R-α-methylhistamine to the H3 receptor was determined to be 40%±2% (% of control). Hence, inhibition of [$^3$H]-R-α-methylhistamine specific binding to the H3 receptor was about 60%, as a surrogate measure for rat brain H3 receptor occupancy by the test compound at 1 hour following oral 10 mg/kg dosing.

For 1-(1-methylethyl)-4-{[4-(tetrahydro-2H-pyran-4-yloxy)phenyl]carbonyl}piperazine hydrochloride, within the present invention, dosed orally to rats (n=3) at 10 mg/kg, and with the rats sacrificed 4 hours following oral dosing, the specific binding of [$^3$H]-R-α-methylhistamine to the H3 receptor was determined to be 84%±6% (% of control). Hence, inhibition of [$^3$H]-R-α-methylhistamine specific binding to the H3 receptor was about 16%, as a surrogate measure for rat brain H3 receptor occupancy by the test compound at 4 hours following oral 10 mg/kg dosing.

For 1-(isopropyl)-4-{[4-(tetrahydro-2H-pyran-4-yloxy) phenyl]carbonyl}hexahydro-1H-1,4-diazepine hydrochloride

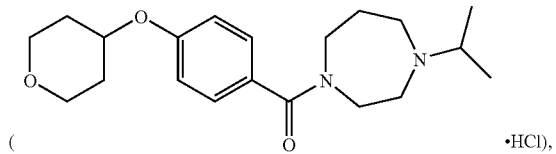

a comparator compound, dosed orally to rats (n=3) at 10 mg/kg, and with the rats sacrificed 1 hour following oral dosing, the specific binding of [$^3$H]-R-α-methylhistamine to the H3 receptor was determined to be 40%±4% (% of control). Hence, inhibition of [$^3$H]-R-α-methylhistamine specific binding to the H3 receptor was about 60%, as a surrogate measure for rat brain H3 receptor occupancy by the test compound at 1 hour following oral 10 mg/kg dosing.

For 1-(isopropyl)-4-{[4-(tetrahydro-2H-pyran-4-yloxy) phenyl]carbonyl}hexahydro-1H-1,4-diazepine hydrochloride, a comparator compound, dosed orally to rats (n=3) at 10 mg/kg, and with the rats sacrificed 4 hours following oral dosing, the specific binding of [$^3$H]-R-α-methylhistamine to the H3 receptor was determined to be 88%±6% (% of control). Hence, inhibition of [$^3$H]-R-α-methylhistamine specific binding to the H3 receptor was about 12%, as a surrogate measure for rat brain H3 receptor occupancy by the test compound at 4 hours following oral 10 mg/kg dosing.

Histamine H3 Receptor Antagonist "Pig-Pet" Studies, Using Positron Emission Tomography (PET) in the Yorkshire-Landrace Pig: Pig Brain H3 Receptor Occupancy Profiles Over Time These studies, and results arising therefrom, are illustrated in part by the attached FIGS. 10, 11, 12, 13 and 14, already briefly described.

Theory of Positron Emission Tomography (PET)

PET is a nuclear imaging technique that enables the measurement of the four-dimensional (three space, one time) distribution of a radiopharmaceutical in the living body. A bioactive molecule (which binds to the receptor of interest, in the present case the histamine H3 receptor) is modified by exchanging one of its atoms by a positron emitting nuclei (e.g. $^{15}$O, $^{11}$C, $^{18}$F, etc). The radioactive molecule (radiopharmaceutical) is then intravenously injected into the subject. In the theory, a positron-emitting atom undergoes radioactive decay by releasing a positron from its nucleus. Generally after several interactions with the surroundings the positron loses kinetic energy and interacts with an electron by annihilation. The annihilation results in two high energy photons (2×511 keV) emitted at 180° to each other. The high energy photon-pair generated by the positron-electron annihilation, emitted at 180°, can be detected externally. A ring of crystal detectors in the PET scanner senses the presence of two photons generated simultaneously and records data for the two detectors pair that sensed the two photons, enabling localization of the activity. This is generally done millions of times during the course of a PET scan. 3D images are sub-sequentially generated using tomographic reconstruction techniques. The nature of PET is intrinsically quantitative therefore the three-dimensional distribution of the radiopharmaceutical can be expressed in units of Bq/ml or nM using the specific activity (SA) of the radiopharmaceutical.

Measuring In Vivo Receptor Occupancy with PET

Figure 10:
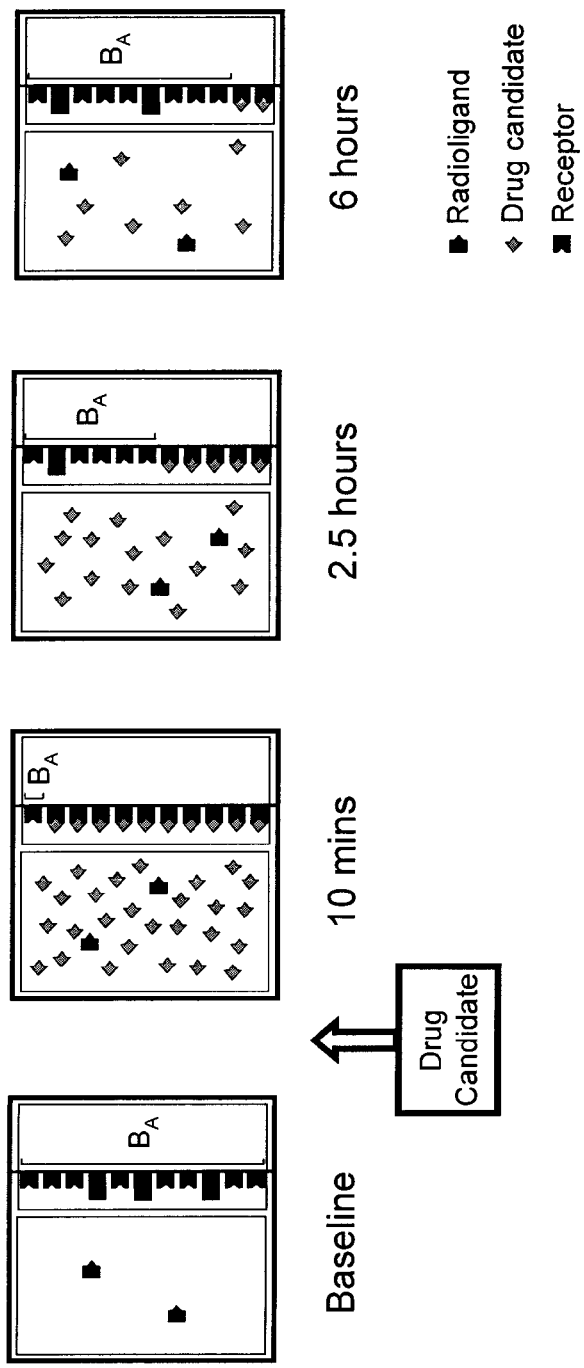
FIG. 10 is a scheme showing how the receptor occupancy of a test compound ("drug candidate") can be measured in vivo by the reduction in radioligand specific binding to receptors. $B_A$ is the concentration of available receptor sites. Notice how $B_A$ changes between baseline, and 10 min, 2.5 hours, and 6 hours after administration of the test compound, as a consequence of the presence of different concentrations of the drug candidate in tissue.

Receptor occupancy of a non-radiolabelled test compound ("drug candidate") can be measured indirectly by measuring the reduction in specific binding of the radioligand as a consequence of competitive binding (FIG. 10). As FIG. 10 shows, the occupancy of the drug candidate can be measured indirectly by the reduction in radioligand specific binding to receptors. $B_A$ is the concentration of available receptors sites. Notice how $B_A$ changes between baseline, and 10 min, 2.5 hours, and 6 hours after administration of the test compound, as a consequence of the presence of different concentrations of the drug candidate in tissue.

A baseline scan is performed where a small mass of the radioligand (in the pg range such that the self-occupancy of the radioligand is minimal, <10%) is administered to the subject. Using regional time activity curves from a target and a reference region (area devoid of specific binding sites) and a mathematical model it is possible to estimate the binding potential, $BP_{ND}$, which is proportional to the concentration of available receptor $B_A$ of each target region. Following the baseline scan the unlabeled drug candidate is administered to the subject and sub-sequent scans are acquired at time points of interest and binding potentials are estimated. The drug candidate occupancy at different time points is calculated as the percentage change of the binding potential measurements with respect to baseline (J. Passchier, A. Gee, A. Willemsen, W. Vaalburg, and A. van Waarde, "Measuring drug-related receptor occupancy with positron emission tomography," *Methods*, 2002, vol. 27, pp. 278-286).

Preclinical Pet Studies in the Yorkshire-Landrace Pig

The H3 receptor occupancy (RO) time course of:
1-(1-methylethyl)-4-{[4-(tetrahydro-2H-pyran-4-yloxy) phenyl]carbonyl}piperazine hydrochloride ("salt A", within the present invention), and
1-(isopropyl)-4-{[4-(tetrahydro-2H-pyran-4-yloxy)phenyl] carbonyl}hexahydro-1H-1,4-diazepine hydrochloride ("salt B", a comparator compound)
were measured in the Yorkshire-Landrace pig using the selective H3 receptor antagonist [$^{11}$C]GSK189254 and PET.

[$^{11}$C]GSK189254 is [$^{11}$C—N-methyl]-6-(3-cyclobutyl-2, 3,4,5-tetrahydro-1H-benzo[d]azepin-7-yloxy)-nicotinamide, the structure of which is

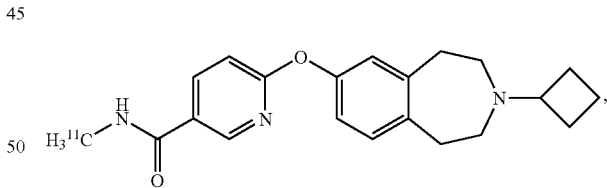

and/or a pharmaceutically acceptable salt thereof. See page 5 line 8 to page 6 line 11 of WO 2006/072596 A1 (Glaxo Group Limited), Example 1 (Compound A) therein, for the preparation of [$^{11}$C]GSK189254 by the reaction of 6-(3-cyclobutyl-2,3,4,5-tetrahydro-1H-benzo[d]azepin-7-yloxy)-nicotinamide with [$^{11}$C]methyl iodide at 130° C. in dimethylsulfoxide in the presence of tetrabutylammonium fluoride, followed by HPLC purification. See e.g. page 7 line 32 to page 9 line 2 of WO 2006/072596 A1 for the use of [$^{11}$C]GSK189254 in (pig) PET imaging studies.

Pig-PET Studies Using 1-(1-methylethyl)-4-{[4-(tetrahydro-2H-pyran-4-yloxy)phenyl]carbonyl}piperazine hydrochloride ("salt A")

Figure 11:
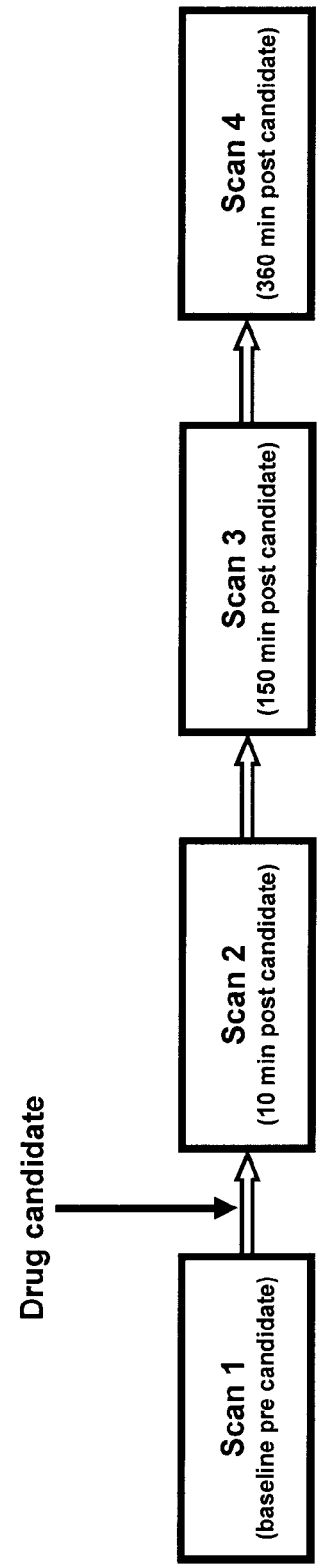
FIG. 11 is a scheme showing the pig-PET protocol to measure the H3 receptor occupancy of 1-(1-methylethyl)-4-{[4-(tetrahydro-2H-pyran-4-yloxy)phenyl]carbonyl}piperazine hydrochloride ("salt A", within the present invention), and 1-(isopropyl)-4-{[4-(tetrahydro-2H-pyran-4-yloxy)phenyl]carbonyl}hexahydro-1H-1,4-diazepine hydrochloride ("salt B", a comparator compound).

Yorkshire-Landrace pigs (n=3, pig weight about 38±1 kg) underwent four PET scans in the same day, as shown in the pig-PET protocol illustrated in FIG. 11, under anaesthesia (ketamine-midazolam induction+isofluorane maintenance).

The radioligand [$^{11}$C]GSK189254 was synthesized immediately before each PET scan. The crude [$^{11}$C]GSK189254-containing reaction product was subject to HPLC purification performed using a reverse phase C$_{18}$ column (Waters, X-terra® RP18, 19×100 mm, 5 mm) at 10 mL/min flow rate with a mobile phase consisting of 17% of acetonitrile in a 0.1 N aqueous buffer solution of ammonium formate at pH 4. The [$^{11}$C]GSK189254-containing product fraction collected was concentrated in vacuo to remove the acetonitrile and reformulated in 0.9% aqueous sodium chloride solution.

For each PET scan, the radioligand [$^{11}$C]GSK189254, in the above-mentioned vehicle which was effectively a mixture of aqueous ammonium formate buffer and saline, was administered intravenously (i.v.) over about 1 minute as a bolus. Less than 2 micrograms total mass of [$^{11}$C]GSK189254 was injected, with a mean total dose injected of less than 53 ng/kg for a pig weight of about 38±1 kg. The amount of radioactivity injected into each pig via [$^{11}$C]GSK189254 was generally about 250 to about 400 MBq (ideally about 300 MBq). The volume of [$^{11}$C]GSK189254+vehicle injected per pig depends on the yield obtained from the last HPLC purification, but generally ranged from about 2 to about 11 ml.

Blood and tissue activity concentration data were recorded for 90 minutes.

Following the baseline scan, unlabelled 1-(1-methylethyl)-4-{[4-(tetrahydro-2H-pyran-4-yloxy)phenyl]carbonyl}piperazine hydrochloride ("salt A", 50 µg/kg, 50 micrograms/kg) (1 ml in an aqueous saline vehicle) was administered intravenously by manual injection in a bolus fashion over approximately 1 minute. The subsequent PET acquisitions were initiated at 10, 150, and 360 minutes post administration of salt A. The arterial blood samples were assayed for [$^{11}$C]GSK189254 plasma activity and metabolites and 1-(1-methylethyl)-4-{[4-(tetrahydro-2H-pyran-4-yloxy)phenyl]carbonyl}piperazine plasma concentrations.

Pig-PET Studies Using 1-(isopropyl)-4-{[4-(tetrahydro-2H-pyran-4-yloxy)phenyl]carbonyl}hexahydro-1H-1,4-diazepine hydrochloride ("salt B")

Substantially the same experimental procedure was repeated using 1-(isopropyl)-4-{[4-(tetrahydro-2H-pyran-4-yloxy)phenyl]carbonyl}hexahydro-1H-1,4-diazepine hydrochloride ("salt B", 50 µg/kg, 50 micrograms/kg in a vehicle) in Yorkshire-Landrace pigs (n=3, pig weight about 38±1 kg).

Binding Potential and Occupancy Measurements

PET images were aligned to a stereotaxic atlas and regional time activity curves were obtained for the target regions of interest (frontal cortex, hippocampus, putamen, caudate, diencephalon, medial thalamus, lateral thalamus, vermis, pons, mesencephalon, and medulla oblongata). The simplified reference tissue model (SRTM) (A. A. Lammertsma and S. P. Hume, "Simplified reference tissue model for PET receptor studies," *Neuroimage*, 1996, vol. 4, pp. 153-158) was fitted to each regional time activity curve using the cerebellum as the reference region:

$$C_t(t) = R_1 C_r(t) + \left(k_2 - \frac{R_1 k_2}{1 + BP_{ND}}\right) C_r(t) \otimes e^{\frac{k_2 t}{1 + BP_{ND}}}$$

where $C_t(t)$ is the activity concentration in the target region, $C_r(t)$ is the activity concentration in the reference region (cerebellum), $R_1$ is the ratio of influx ($K_1$) between the target and reference region, $k_2$ is the tissue-plasma efflux rate constant in the target region, and $BP_{ND}$ is the binding potential of the target region. Moreover the binding potential can be defined as $$BP_{ND} = f_{ND} \frac{B_A}{K_d}$$

where $f_{ND}$ is the radioligand free fraction in tissue, $B_A$ is the available concentration of binding sites, and $K_d$ is the equilibrium dissociation constant of the radioligand-receptor complex.

Receptor occupancy can be calculated as the percentage change in $BP_{ND}$ between the baseline and post drug scan (J. Passchier, A. Gee, A. Willemsen, W. Vaalburg, and A. van Waarde, "Measuring drug-related receptor occupancy with positron emission tomography," *Methods*, 2002, vol. 27, pp. 278-286):

$$Occ = \left(\frac{BP_{ND}^{baseline} - BP_{ND}^{drug}}{BP_{ND}^{baseline}}\right) \times 100$$

In the case of [$^{11}$C]GSK189254 the cerebellum is not a true reference region as there exists a small specific signal in this region. This can be corrected using a population estimate of the cerebellum binding potential ($BP_{ND}^{ref}$) and the equation $$Occ^{corrected} = Occ \cdot \left(\frac{1 + BP_{ND}^{ref}}{1 + BP_{ND}^{ref} Occ}\right)$$

Modelling the Occupancy Profile

The temporal occupancy profile at 10, 150, and 360 minutes (Occ(t)) post administration of the drug candidate and the plasma concentration of the drug candidate ($C_p(t)$) measured throughout the PET whole scan were used to derive PK/RO (pharmacokinetic/receptor occupancy) model parameter estimates ($f_p$, $k_{on}$, and $k_{off}$) from an indirect model ($k_{on}$-$k_{off}$ limited model)

$$\frac{dOcc(t)}{dt} = f_p k_{on}(1 - Occ(t))C_p(t) - k_{off} Occ(t)$$

wherein $k_{on}$ and $k_{off}$ are respectively the rate constants defining the speed that the test compound attaches or de-attaches to or from the H3 receptor, and $f_p$ is the protein-free fraction in plasma of the test compound (here, salt A or salt B).

This model assumes that the rate limiting step is the receptor-ligand association and dissociation ($k_{on}$, $k_{off}$) whilst the plasma-tissue exchange is rapid enough to be considered in instantaneous equilibrium.

Results of pig-PET Studies

Figure 12:
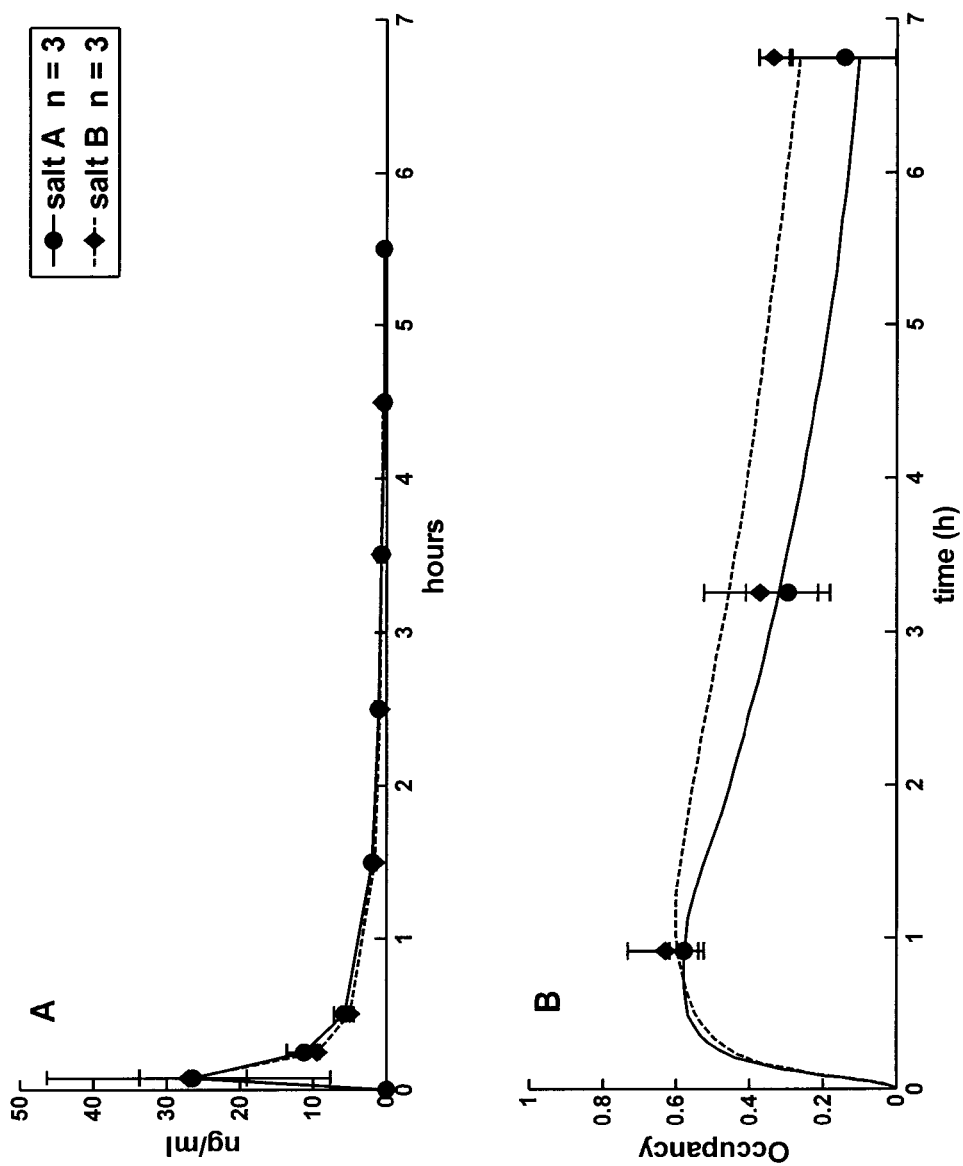
FIG. 12, graph A, is a graph showing the average (mean) plasma concentration over time of 1-(1-methylethyl)-4-{[4-(tetrahydro-2H-pyran-4-yloxy)phenyl]carbonyl}piperazine hydrochloride ("salt A", within the present invention, filled circles) and 1-(isopropyl)-4-{[4-(tetrahydro-2H-pyran-4-yloxy)phenyl]carbonyl}hexahydro-1H-1,4-diazepine hydrochloride ("salt B", a comparator compound, filled diamonds), following 50 micrograms/kg intravenous administration to pigs.

FIG. 12, graph A, shows the average (mean) plasma concentration over time of 1-(1-methylethyl)-4-{[4-(tetrahydro-2H-pyran-4-yloxy)phenyl]carbonyl}piperazine hydrochloride ("salt A", within the present invention, filled circles) and 1-(isopropyl)-4-{[4-(tetrahydro-2H-pyran-4-yloxy)phenyl]carbonyl}hexahydro-1H-1,4-diazepine hydrochloride ("salt B", a comparator compound, filled diamonds).

FIG. 12, graph B, shows the average (mean) measured H3 receptor occupancy time course at three time points; and the $k_{on}$-$k_{off}$ limited model fitted to it for "salt A" within the present invention (measurements as filled circles, and model fit as solid line), and for "salt B" a comparator compound (measurements as filled diamonds, and model fit as dashed line).

FIG. 13, parts A and B, are graphs showing the data from FIG. 12 for salt A alone such as to show the average (mean) plasma concentration over time and average (mean) H3 receptor occupancy time course respectively for "salt A". FIG. 13, parts C and D, are graphs showing the data from FIG. 12 for salt B alone such as to show the average (mean) plasma concentration over time and average (mean) H3 receptor occupancy time course respectively for "salt B".

Figure 14:
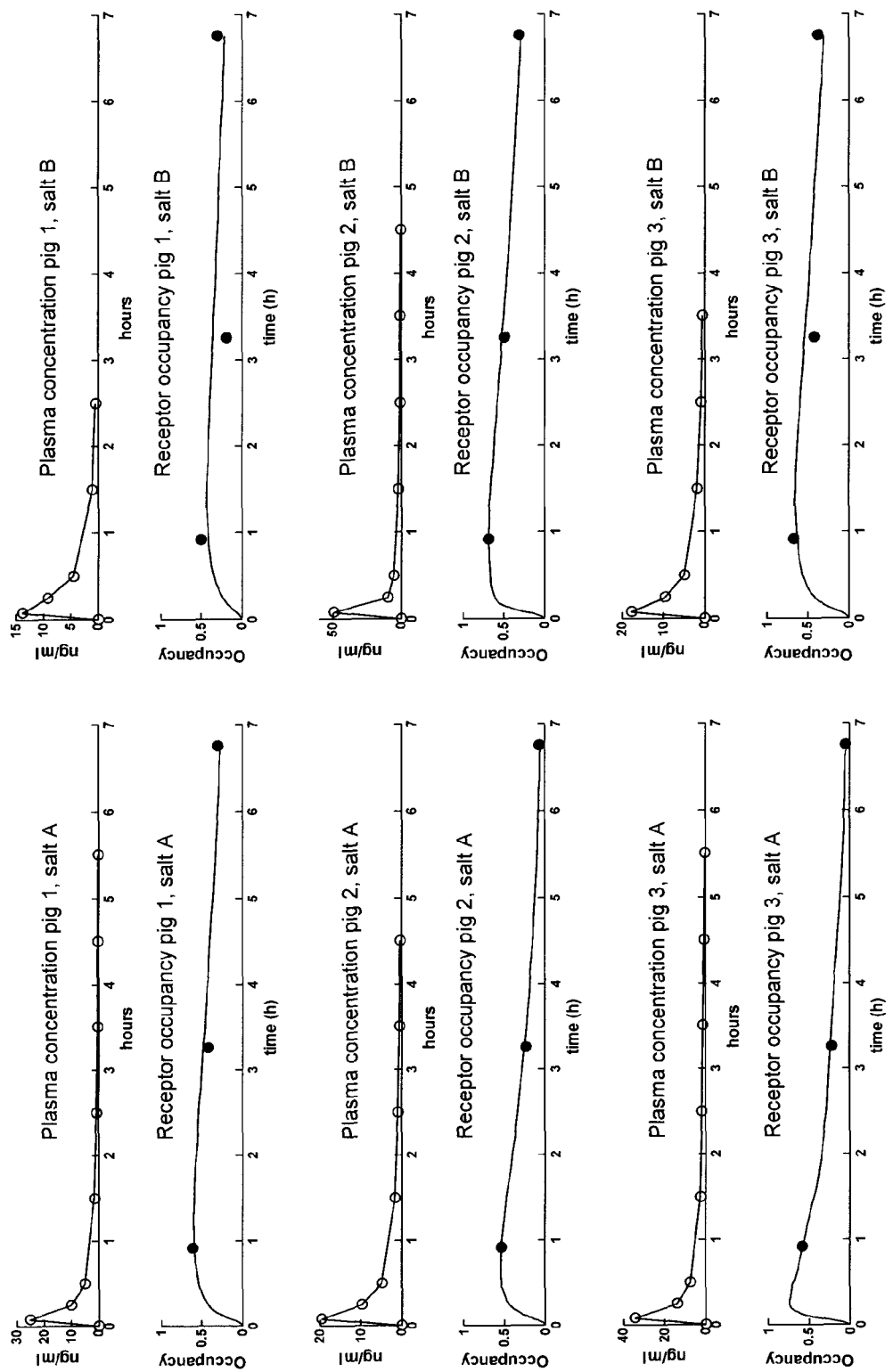
FIG. 14 is a series of graphs showing individual plasma concentration and H3 receptor occupancy time courses, for each individual pig studied, which are the data which generated the mean measurements shown in FIGS. 12 and 13, for 1-(1-methylethyl)-4-{[4-(tetrahydro-2H-pyran-4-yloxy)phenyl]carbonyl}piperazine hydrochloride ("salt A", within the present invention, left hand graphs, n=3), and for 1-(isopropyl)-4-{[4-(tetrahydro-2H-pyran-4-yloxy)phenyl]carbonyl}hexahydro-1H-1,4-diazepine hydrochloride ("salt B", a comparator compound, right hand graphs, n=3).

FIG. 14 shows separated individual plasma concentration and H3 receptor occupancy time courses, for each individual pig studied, for 1-(1-methylethyl)-4-{[4-(tetrahydro-2H-pyran-4-yloxy)phenyl]carbonyl}piperazine hydrochloride ("salt A", within the present invention, left hand graphs, n=3), and for 1-(isopropyl)-4-{[4-(tetrahydro-2H-pyran-4-yloxy)phenyl]carbonyl}hexahydro-1H-1,4-diazepine hydrochloride ("salt B", a comparator compound, right hand graphs, n=3).

Table 1 shows the estimated parameters $k_{on}$, $k_{off}$, $K_d$ ($k_{off}/k_{on}$), and the plasma clearance for each individual study (i.e. for each individual pig). The last row in Table 1 ("average model") shows the estimated parameters derived from the average plasma data and average occupancy (FIGS. 12, 13); it can be noticed that these "average model" parameters appear to be in general agreement with the average parameters ("mean") estimated individually for each scan (second row from the bottom).

TABLE 1

Estimated model parameters for each individual study (each individual pig) and the parameters derived from average data.

| | Salt A | | | | Salt B | | | |
| --- | --- | --- | --- | --- | --- | --- | --- | --- |
| | $k_{on}$ (min$^{-1}$) | $k_{off}$ (min$^{-1}$) | $K_d$ (ng/ml) | Plasma clearance (L/hr) | $k_{on}$ (min$^{-1}$) | $k_{off}$ (min$^{-1}$) | $K_d$ (ng/ml) | Plasma clearance (L/hr) |
| pig 1 | 0.0023 | 0.0038 | 1.65 | 2.9 | 0.0017 | 0.0033 | 1.94 | 3.6 |
| pig 2 | 0.0033 | 0.0114 | 3.45 | 3.0 | 0.0024 | 0.0042 | 1.75 | 1.8 |
| pig 3 | 0.0058 | 0.0286 | 4.93 | 1.8 | 0.0031 | 0.0039 | 1.25 | 2.8 |
| mean | 0.0038 | 0.0146 | 3.35 | 2.5 | 0.0024 | 0.0038 | 1.65 | 2.8 |
| average model | 0.0027 | 0.0091 | 3.37 | 2.3 | 0.0025 | 0.0045 | 1.80 | 2.9 |

Table 2 shows the measured H3 receptor occupancy at three time points, in each the three individual studies performed (in each of the three individual pigs studied), for each test compound, salt A and salt B.

TABLE 2

Measured H3 receptor occupancy (and mean occupancy ± standard deviation), at 10 minutes, 2.5 hours and 6 hours post administration of the test compound, in the three individual pigs, for each test compound, salt A and salt B.

| | Salt A occupancy @ | | | Salt B occupancy @ | | |
| --- | --- | --- | --- | --- | --- | --- |
| | 10 min | 2.5 h | 6 h | 10 min | 2.5 h | 6 h |
| pig 1 | 61% | 43% | 30% | 51% | 19% | 30% |
| pig 2 | 54% | 24% | 7% | 69% | 49% | 32% |
| pig 3 | 58% | 22% | 5% | 68% | 43% | 38% |
| Mean | 58% ± 4% | 30% ± 11% | 14% ± 14% | 63% ± 10% | 37% ± 16% | 33% ± 4% |

Conclusion of pig-PET Studies

The preliminary measurements obtained in the Yorkshire-Landrace pig (n=3) by PET and [$^{11}$C]GSK189254 appear to indicate a generally faster reduction in pig brain H3 receptor occupancy of 1-(1-methylethyl)-4-{[4-(tetrahydro-2H-pyran-4-yloxy)phenyl]carbonyl}piperazine hydrochloride ("salt A", within the present invention), as compared to 1-(isopropyl)-4-{[4-(tetrahydro-2H-pyran-4-yloxy)phenyl]carbonyl}hexahydro-1H-1,4-diazepine hydrochloride ("salt B", a comparator compound), under the conditions tested (i.e. after 50 micrograms/kg of intravenous administration of the test compound to the pigs, and under the other stated conditions).

The apparently faster reduction in pig brain H3 receptor occupancy for salt A, within the present invention, compared to comparator salt B, is seen in studies 2 and 3 (i.e. pigs 2 and 3) tested with salt A, but apparently not in study 1 (i.e. pig 1) tested with salt A, as illustrated in Table 2 above.

Toxicity Study 1: Toxicity of 1-(1-methylethyl)-4-{[4-(tetrahydro-2H-pyran-4-yloxy)phenyl]carbonyl}piperazine hydrochloride in a 7-Day, Oral Repeat-Dose Study in Male Sprague Dawley Rats Design of Toxicity Study 1

The objective of this study was to determine the toxicity of 1-(1-methylethyl)-4-{[4-(tetrahydro-2H-pyran-4-yloxy)phenyl]carbonyl}piperazine hydrochloride, and the toxicokinetics of 1-(1-methylethyl)-4-{[4-(tetrahydro-2H-pyran-4-yloxy)phenyl]-carbonyl}piperazine hydrochloride (measured as the free base), in a 7-day, oral repeat-dose study in male Sprague Dawley rats.

1-(1-Methylethyl)-4-{[4-(tetrahydro-2H-pyran-4-yloxy)phenyl]carbonyl}piperazine hydrochloride was formulated as a suspension in 1% (w/v) aqueous methylcellulose and administered to male rats (four per group), at doses of 0 (vehicle, control), 30, 100 or 300 mg/kg/day for 7 days by oral gavage, at a dose volume of 10 mL/kg. Three male rats were added at each non-zero dose level for toxicokinetic evaluation. All doses and concentrations, including analyte concentration in plasma, are expressed in terms of the parent "free base" compound.

The following endpoints/parameters were evaluated for toxicology animals: clinical observations, body weights, food consumption measurements, selected haematology and selected clinical chemistry results, liver weights, selected macroscopic and microscopic observations, and selected hepatic gene expression analysis. Toxicokinetic evaluation (serial profiling) was performed on samples collected from satellite animals on Days 1 and 7. For male rats dosed at 30 or 100 mg/kg/day, histopathology observations carried out were on kidneys, mesentery and mandibular lymph node only. For male rats dosed at 0 mg/kg/day (control) and 300 mg/kg/day, histopathology observations carried out were on adrenals, brain, heart, kidneys, liver, lung, mandibular lymph node, mesentery, stomach, testes, and thymus (except that mandibular lymph node observations were for 0 mg/kg/day dosed rats only).

Summary of main results of Toxicity Study 1

Reduced body weight gain (ca. 0.38×control) and food consumption (ca. 0.80×pretreatment) were observed in male rats at doses of 300 mg/kg/day.

Increased body weight gain (ca. 1.43×mean control) was seen in male rats at 100 mg/kg/day.

A periarterial inflammatory cell infiltrate, minimal in severity, was noted in the hilar region of the kidneys of all four male rats treated with doses of 300 mg/kg/day, and was unilateral (2 of 4 rats) or bilateral (2 of 4 rats). This finding was not noted in mesenteric arteries, or any other of the arteries which were examined, and its significance is unclear.

The kidneys of male rats dosed at 0 (vehicle), 30 and 100 mg/kg/day were examined; no kidney hilar periarterial inflammatory cell infiltrate was found at these doses.

Cholesterol concentrations were slightly reduced (ca. 0.65×mean control) in male rats at 300 mg/kg/day.

Rubbing chin on cage floor, accompanied by chewing movements, was noted at all non-zero doses in male rats, predominantly at 300 mg/kg/day.

Certain other observations in male rats were noted at 300 mg/kg/day or at 100 and 300 mg/kg/day doses, but were generally sporadic, transient and predominantly slight.

In male Sprague Dawley rats, oral-repeat-dosing for 7 days of 30 or 100 mg/kg/day of 1-(1-methylethyl)-4-{[4-(tetrahydro-2H-pyran-4-yloxy)phenyl]carbonyl}piperazine hydrochloride (measured as the free base) appears to be well tolerated. In male Sprague Dawley rats, oral-repeat-dosing for 7 days of 300 mg/kg/day of this salt (measured as the free base) appears to be moderately well tolerated.

Toxicity Study 2: Toxicity of 1-(1-methylethyl)-4-{[4-(tetrahydro-2H-pyran-4-yloxy)phenyl]carbonyl}piperazine hydrochloride in a 7-Day, Oral, Dose Range-Finding Study in Sprague Dawley Rats 1-(1-Methylethyl)-4-{[4-(tetrahydro-2H-pyran-4-yloxy) phenyl]carbonyl}piperazine hydrochloride, formulated as a suspension in 1% (w/v) aqueous methylcellulose, was administered to groups of Sprague Dawley rats at a dose volume of 10 mL/kg as follows (all doses and concentrations are expressed in terms of the parent "free base" compound):

administered to male rats (4 per group) at doses of 0 (vehicle, control) or 600 mg/kg/day once daily for up to 7 days by oral gavage (only 2 days at 600 mg/kg/day);

administered to female rats (4 per group) at doses of 0 (vehicle, control) or 300 or 600 mg/kg/day once daily for up to 7 days by oral gavage (only 2 days at 600 mg/kg/day).

Three male rats and three female rats were added at 600 mg/kg/day and 3 female rats were added at 300 mg/kg/day for toxicokinetic evaluation.

The following endpoints/parameters were evaluated for toxicology animals: clinical observations, body weights, food consumption, selected haematology, selected clinical chemistry, liver weights, and selected macroscopic and microscopic observations. Toxicokinetic evaluation was performed on samples collected on Day 1 (300 and 600 mg/kg/day dosing) and Day 7 (300 mg/kg/day dosing only).

The dose of 600 mg/kg/day was not tolerated in either male or female Sprague Dawley rats.

For the dose of 300 mg/kg/day in female rats:

clinical signs included chewing movements, rubbing chin on the cage floor, and certain other clinical signs;

certain haematology and other clinical chemistry parameters were increased;

urea and cholesterol concentrations were decreased (urea ca. 0.81×control or mean control, and cholesterol ca. 0.52×control or mean control); and liver weight was increased (ca. 1.24×control or mean control), although there appeared to be no related macroscopic or microscopic observations.

Glandular dilation of the fundic region of the stomach, of minimal severity, was observed in most female rats given doses of 300 mg/kg/day. This change was also present in two controls (one male and one female) and its significance is unclear at this stage.

In female Sprague Dawley rats, oral-repeat-dosing for 7 days of 300 mg/kg/day of 1-(1-methylethyl)-4-{[4-(tetrahydro-2H-pyran-4-yloxy)phenyl]carbonyl}piperazine hydrochloride (measured as the free base) appears to be moderately well tolerated.

Preliminary conclusions from Toxicity Studies 1 and 2

1-(1-Methylethyl)-4-{[4-(tetrahydro-2H-pyran-4-yloxy) phenyl]carbonyl}piperazine hydrochloride appears to be well tolerated or moderately well tolerated in male and female Sprague Dawley rats after 7 days of oral-repeat-dosing at doses of up to 300 mg/kg/day (measured as the free base).

The invention claimed is:

1. A compound which is 1-(1-methylethyl)-4-{[4-(tetrahydro-2H-pyran-4-yloxy)phenyl]carbonyl}piperazine, having the following structure:

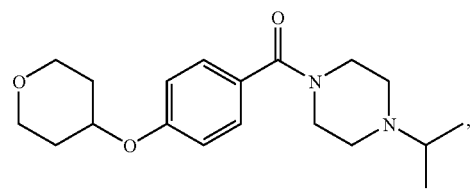

or a pharmaceutically acceptable salt thereof.

2. The salt as claimed in claim 1, which is 1-(1-methylethyl)-4-{[4-(tetrahydro-2H-pyran-4-yloxy)phenyl] carbonyl}piperazine hydrochloride.

3. A pharmaceutical composition which comprises the compound or salt as claimed in claim 1, and a pharmaceutically acceptable carrier or excipient.

4. A pharmaceutical composition, which is for oral administration, and which comprises the salt as claimed in claim 2, and a pharmaceutically acceptable carrier or excipient.

* * * * *